(12) United States Patent
Pasteris et al.

(10) Patent No.: US 8,420,673 B2
(45) Date of Patent: *Apr. 16, 2013

(54) FUNGICIDAL AMIDES

(75) Inventors: Robert James Pasteris, Newark, DE (US); George Philip Lahm, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 351 days.

This patent is subject to a terminal disclaimer.

(21) Appl. No.: 12/521,156

(22) PCT Filed: Jan. 18, 2008

(86) PCT No.: PCT/US2008/000786
§ 371 (c)(1),
(2), (4) Date: Jun. 25, 2009

(87) PCT Pub. No.: WO2008/091580
PCT Pub. Date: Jul. 31, 2008

(65) Prior Publication Data
US 2010/0004288 A1    Jan. 7, 2010

Related U.S. Application Data

(60) Provisional application No. 60/897,792, filed on Jan. 25, 2007.

(51) Int. Cl.
*A61K 31/4535* (2006.01)
*C07D 407/02* (2006.01)

(52) U.S. Cl.
USPC .................................. 514/326; 546/269.7

(58) Field of Classification Search .............. 514/326; 546/269.7
See application file for complete search history.

(56) References Cited

U.S. PATENT DOCUMENTS

2006/0069102 A1   3/2006   LeBan et al.

FOREIGN PATENT DOCUMENTS

| WO | 02/059086   | 8/2002  |
|----|-------------|---------|
| WO | 2004/058751 | 7/2004  |
| WO | 2005/003128 | 1/2005  |
| WO | 2005/116653 | 12/2005 |
| WO | 2007/014290 | 2/2007  |
| WO | 2008/013622 | 1/2008  |
| WO | 2008/013925 | 1/2008  |

OTHER PUBLICATIONS

Search Report on EP 08 724 674.0-2101 of Jan. 18, 2008.*
U.S. Appl. No. 11/988,359, filed Jan. 4, 2008, which claims priority to International Application No. PCT/US06/29175, filed Jul. 26, 2006, and U.S. Appl. No. 60/702,579, filed Jul. 26, 2005.
U.S. Appl. No. 12/303,256, filed Dec. 3, 2008, which claims priority to International Appln. No. PCT/US07/16875, filed Jul. 27, 2007, U.S. Appl. No. 60/833,824, filed Jul. 27, 2006 and U.S. Appl. No. 60/897,173, filed Jan. 24, 2007.
U.S. Appl. No. 12/679,361, filed Mar. 22, 2010, which claims priority to International Appln. No. PCT/US08/80850, filed Oct. 23, 2008, U.S. Appl. No. 61/000,002, filed Oct. 23, 2007 and U.S. Appl. No. 61/062,400, filed Jan. 25, 2008.
U.S. Appl. No. 12/811,126, filed Jun. 29, 2010, which claims priority to International Appln. No. PCT/US09/31618, filed Jan. 22, 2009, and U.S. Appl. No. 61/062,367, filed Jan. 25, 2008.
U.S. Appl. No. 12/863,875, filed Jul. 21, 2010, which claims priority to International Appln. No. PCT/US09/31686, filed Jan. 22, 2009, and U.S. Appl. No. 61/062,395, filed Jan. 25, 2008.
U.S. Appl. No. 13/127,809, filed May 5, 2011, which claims priority to International Appln. No. PCT/US09/66318, filed Dec. 2, 2009, and U.S. Appl. No. 61/119,137, filed Dec. 2, 2008.
U.S. Appl. No. 13/265,138, filed Oct. 19, 2011, which claims priority to International Appln. No. PCT/US10/31546, filed Apr. 19, 2010, U.S. Appl. No. 61/171,573, filed Apr. 22, 2009, and U.S. Appl. No. 61,311,512, filed Mar. 8, 2010.
International Appln. No. PCT/US11/20473, filed Jan. 7, 2011, which claims priority from U.S. Appl. No. 61/293,095, filed Jan. 7, 2010 and U.S. Appl. No. 61/350,535, filed Jun. 2, 2010.
International Appln. No. PCT/US11/32599, filed Apr. 15, 2011, which claims priority from U.S. Appl. No. 61/346,606, filed May 20, 2010 and U.S. Appl. No. 61/366,602, filed Jul. 22, 2010.
International Appln. No. PCT/US11/64324, filed Dec. 12, 2011, which claims priority from U.S. Appl. No. 61/424,228, filed Dec. 17, 2010.

* cited by examiner

*Primary Examiner* — Taofiq A Solola

(57) ABSTRACT

Disclosed are compounds of Formula 1, including all geometric and stereoisomers, N-oxides, and salts thereof,

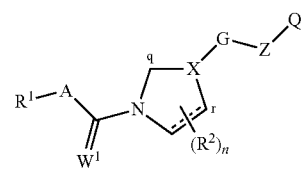

1 wherein
$R^1$, $R^2$, A, G, $W^1$, Q, X, Z, and n are as defined in the disclosure.
Also disclosed are compositions containing the compounds of Formula 1 and methods for controlling plant disease caused by a fungal pathogen comprising applying an effective amount of a compound or a composition of the invention.

22 Claims, No Drawings

FUNGICIDAL AMIDES

FIELD OF THE INVENTION

This invention relates to certain carboxamides, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

World Patent Publication WO 05/003128 discloses thiazolylpiperidine derivatives of Formula i as MTP (Microsomal Triglyceride transfer Protein) inhibitors.

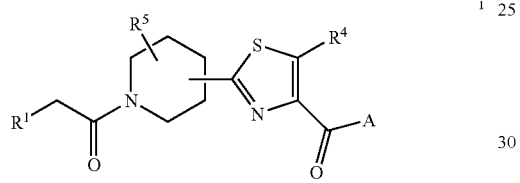

wherein
A is a radical selected from the radicals a1 and a2 below

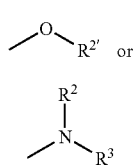

and $R^1$, $R^2$, $R^{2'}$, $R^3$, $R^4$ and $R^5$ are as defined in the disclosure.

World Patent Publication WO 04/058751 discloses piperidinyl-thiazole carboxamide derivatives for altering vascular tone.

SUMMARY OF THE INVENTION

This invention is directed to compounds of Formula 1 including all geometric and stereoisomers, N-oxides, and salts thereof, agricultural compositions containing them and their use as fungicides:

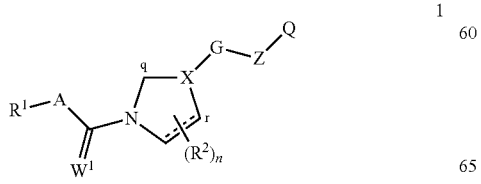

wherein
$R^1$ is an optionally substituted phenyl or 5- or 6-membered heteroaromatic ring;
A is $NR^{18}$ or $C_1$-$C_3$ alkylene optionally substituted with 1-3 substituents independently selected from $R^{17}$;
$W^1$ is O or S;
X is a radical selected from

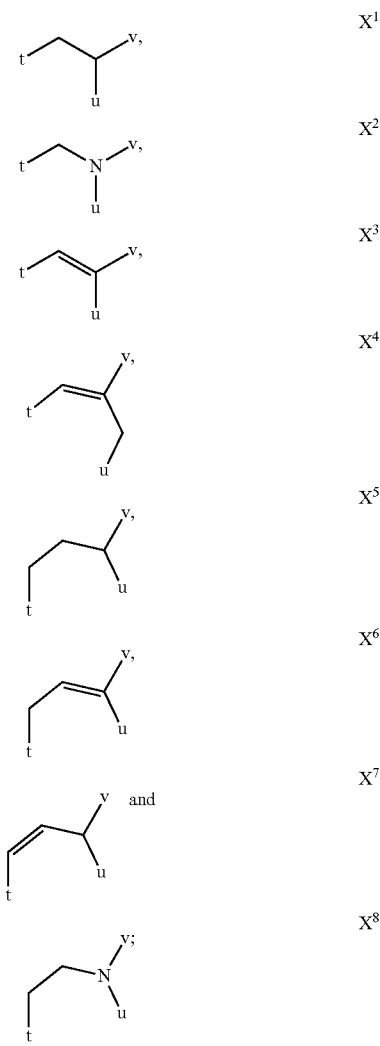

wherein the bond of X which is identified with "t" is connected to the carbon atom identified with "q" of Formula 1, the bond which is identified with "u" is connected to the carbon atom identified with "r" of Formula 1, and the bond which is identified with "v" is connected to G;
each $R^2$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy;
n is 0, 1 or 2; or
two $R^2$ are taken together as $C_1$-$C_3$ alkylene or $C_2$-$C_3$ alkenylene to form a bridged bicyclic ring system; or
two $R^2$ attached to adjacent ring carbon atoms joined by a double bond are taken together as —CH=CH—CH=CH— optionally substituted with 1-3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

G is an optionally substituted 5-membered heteroaromatic ring or 5-membered saturated or partially saturated heterocyclic ring;

Z is C=$W^2$ or $C_1$-$C_3$ alkylene optionally substituted with 1-3 substituents independently selected from $R^{19}$;

$W^2$ is O or S;

Q is —N$Q^aQ^b$;

$Q^a$ is H, —CHO, $C_1$-$C_3$ alkyl, $C_2$-$C_3$ alkenyl, $C_2$-$C_3$ alkynyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_3$ haloalkyl, $C_2$-$C_3$ haloalkenyl, cyano, hydroxy, $C_1$-$C_3$ alkoxy, $C_2$-$C_3$ alkoxyalkyl, $C_1$-$C_3$ hydroxyalkyl, $C_2$-$C_3$ alkylcarbonyl, $C_2$-$C_3$ alkoxycarbonyl, $C_2$-$C_3$ alkylaminocarbonyl or $C_3$-$C_5$ dialkylaminocarbonyl;

$Q^b$ is an optionally substituted 8- to 11-membered saturated or partially saturated bicyclic ring system or an optionally substituted 10- to 15-membered partially saturated tricyclic ring system, each ring system optionally containing 1 to 3 heteroatoms selected from up to 1 O, up to 1 S and up to 3 N, and optionally including 1-3 ring members selected from the group consisting of C(=O), C(=S), S(O), or S(O)$_2$; or $Q^b$ is C$R^5R^6R^{15}$; or $Q^a$ and $Q^b$ are taken together with the nitrogen atom to which they are bonded to form an optionally substituted 5- to 7-membered saturated or partially saturated heterocyclic ring;

$R^5$ is H, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, cyano, nitro, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^6$ is an optionally substituted phenyl, benzyl, naphthalenyl, $C_3$-$C_6$ cycloalkyl, $C_3$-$C_6$ cycloalkenyl or 5- or 6-membered heteroaromatic ring; and $R^{15}$ is H, $C_1$-$C_4$ alkyl, $C_2$-$C_4$ alkenyl, $C_2$-$C_4$ alkynyl, $C_3$-$C_4$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_4$ haloalkyl, $C_2$-$C_4$ haloalkenyl, $C_2$-$C_4$ haloalkynyl, $C_3$-$C_4$ halocycloalkyl or $C_2$-$C_4$ alkoxyalkyl; or $Q^a$ and $R^5$ are taken together with the atoms connecting them to form an optionally substituted 5- to 7-membered ring containing as ring members 2 to 7 carbon atoms and optionally 1 to 3 heteroatoms selected from up to 1 O, up to 1 S and up to 2 N; or $Q^a$ and $R^6$ are taken together with the atoms connecting them to form an optionally substituted 5- to 7-membered ring containing as ring members 2 to 7 carbon atoms and optionally 1 to 3 heteroatoms selected from up to 1 O, up to 1 S and up to 2 N; or $R^5$ and $R^{15}$ are taken together with the carbon atom to which they are bonded to form an optionally substituted 5- to 7-membered ring containing as ring members 2 to 7 carbon atoms and, optionally 1 to 3 heteroatoms selected from up to 1 O, up to 1 S and up to 1 N; or $R^5$ and $R^6$ are taken together with the carbon atom to which they are bonded to form an optionally substituted 5- to 7-membered ring containing as ring members 2 to 7 carbon atoms and, optionally 1 to 3 heteroatoms selected from up to 1 O, up to 1 S and up to 1 N;

$R^{17}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

$R^{18}$ is H, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkoxyalkoxy, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl; and $R^{19}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

provided that:

(a) when X is $X^2$, $X^3$, $X^4$, $X^6$ or $X^8$, then G is not linked to X via a heteroatom of the G ring; and (b) when Z is C=$W^2$, then A is other than NH or $CH_2$.

More particularly, this invention pertains to a compound of Formula 1, including all geometric and stereoisomers, an N-oxide or a salt thereof.

This invention also relates to a fungicidal composition comprising a fungicidally effective amount of a compound of Formula 1 and at least one additional component selected from the group consisting of surfactants, solid diluents or liquid diluents.

This invention also relates to a fungicidal composition comprising a mixture of a compound of Formula 1 and at least one other fungicide.

This invention further relates to a method for controlling plant diseases caused by fungal plant pathogens comprising applying to the plant or portion thereof, or to the plant seed or seedling, a fungicidally effective amount of a compound of the invention (i.e. as a composition described herein).

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and Both A and B are true (or present).

Also, use of "a" or "an" are employed to describe elements and components of the invention. This is done merely for convenience and to give a general sense of the invention. This description should be read to include one or at least one and the singular also includes the plural unless it is obvious that it is meant otherwise.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$ and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. "Alkynylene" denotes a straight-chain or branched alkynediyl containing one triple bond. Examples of "alkynylene" include $C\equiv C$, $CH_2C\equiv C$, $C\equiv CCH_2$ and the different butynylene isomers. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$ "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$ "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Alkylamino", "dialkylamino", "alkenylthio", "alkenylsulfinyl", "alkenylsulfonyl", "alkynylthio", "alkynylsulfinyl", "alkynylsulfonyl", and the like, are defined analogously to the above examples. "Trialkylsilyl" includes three branched and/or straight-chain alkyl radicals attached to and linked through a silicon atom such as trimethylsilyl, triethylsilyl and t-butyl-dimethylsilyl.

As is generally understood, the term "ring member" refers to an atom or other moiety (e.g., $C(=O)$, $C(=S)$, $S(O)$ or $S(O)_2$) forming the backbone of a ring or ring system.

"Aromatic" refers to a ring wherein each of the ring atoms is essentially in the same plane and has a p-orbital perpendicular to the ring plane, and in which (4n+2) π electrons, where n is a positive integer, are associated with the ring to comply with Hückel's rule. The term "aromatic ring system" denotes a carbocyclic or heterocyclic ring system in which at least one ring of the ring system is aromatic. The term "aromatic carbocyclic ring system" denotes a carbocyclic ring system in which at least one ring of the ring system is aromatic. The term "aromatic heterocyclic ring system" denotes a heterocyclic ring system in which at least one ring of the ring system is aromatic. As is generally understood, the term "saturated ring" denotes a ring in which no ring member is bonded to an adjacent ring member through a double bond. Analogously, the term "saturated ring system" denotes a ring system in which no ring member is bonded to an adjacent ring member through a double bond. In regards to degree of saturation, a "partially saturated ring" (alternatively described as a "partially unsaturated ring") is intermediate between a saturated ring and a fully unsaturated ring (which may be aromatic). Therefore the term "partially saturated ring" (which may be carbocyclic or heterocyclic unless otherwise stated) denotes a ring comprising at least one ring member bonded to an adjacent ring member through a double bond and also comprising at least one ring member bonded to an adjacent ring member through a single bond that conceptually could be replaced by a double bond to form a less saturated ring. Analogously, the term "partially saturated bicyclic ring system" denotes a bicyclic ring system (which may be carbocyclic or heterocyclic unless otherwise stated) comprising at least one ring member bonded to an adjacent ring member through a double bond and also comprising at least one ring member bonded to an adjacent ring member through a single bond that conceptually could be replaced by a double bond to form a less saturated ring system. Examples of "partially saturated bicyclic ring system" include tetrahydronaphthalene, tetrahydroquinoline and tetrahydroisoquinoline. The term "partially saturated tricyclic ring system" denotes a tricyclic ring system (which may be carbocyclic or heterocyclic unless otherwise stated) comprising at least one ring member bonded to an adjacent ring member through a double bond and also comprising at least one ring member bonded to an adjacent ring member through a single bond that conceptually could be replaced by a double bond to form a less saturated ring system. In a partially saturated bicyclic ring system, one component ring may be aromatic, and in a partially saturated tricyclic ring system, one or two component rings may be aromatic, provided that in a nonaromatic ring component at least one ring member is bonded to an adjacent ring member through a single bond that conceptually could be replaced by a double bond to form a less saturated ring system.

As is generally understood, the term "bicyclic ring system" denotes a ring system containing two rings that share two or more common atoms. If the common atoms are adjacent (i.e. there is a bond between the bridgehead carbons), the bicyclic ring system is a "fused bicyclic ring system". If the common atoms are not adjacent (i.e. there is no bond between the bridgehead carbons), the ring system is a "bridged bicyclic ring system". Present Embodiment 50 depicts a variety of illustrative fused bicyclic and tricyclic ring systems as the $Q^b$ component of Q. However, $Q^b$ can also be a bridged bicyclic or tricyclic ring system.

Definitions of substituents may allow rings, bicyclic ring systems, and tricyclic systems to be components of more extensive ring systems. For example, Q-59 depicted in Embodiment 50 is formed from Q being $-NQ^aQ^b$ where $Q^b$ is $CR^5R^6R^{15}$ and $R^6$ is an optionally substituted phenyl ring. A substituent on the $R^6$ phenyl ring is taken together with $Q^a$ and the atoms connecting $Q^a$ and $R^6$ to form the six-membered ring containing the nitrogen atom. Another substituent on the $R^6$ phenyl ring is taken together with $R^5$ and the carbon atom to which $R^5$ and $R^6$ are bonded to form the five-membered ring optionally substituted with substituents selected from $R^8$.

The terms "carbocyclic ring", "carbocycle" or "carbocyclic ring system" denote a ring or ring system wherein the atoms forming the ring backbone are selected only from carbon. "Cycloalkyl" includes, for example, cyclopropyl, cyclobutyl, cyclopentyl, and cyclohexyl. Unless otherwise indicated, a carbocyclic ring can be a saturated, partially saturated, or fully unsaturated ring. When a fully unsaturated carbocyclic ring satisfies Hückel's rule, then said ring is also called an "aromatic ring". A carbocyclic ring that does not satisfy Hückel's rule is described as a "nonaromatic carbocyclic ring".

The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially saturated, or fully unsaturated ring. When a fully unsaturated heterocyclic ring satisfies Hückel's rule, then said ring is also called a "heteroaromatic ring" or "aromatic heterocyclic ring". A heterocyclic ring that does not satisfy Hückel's rule is described as a "nonaromatic heterocyclic ring". The term "saturated heterocyclic ring" denotes a heterocyclic ring in which no ring member is bonded to an adjacent ring member through a double bond. The term "partially saturated heterocyclic ring" denotes a heterocyclic ring comprising at least one ring member bonded to an adjacent ring member through a double bond and also comprising at least one ring member bonded to an adjacent ring member through a single bond that conceptually could be replaced by a double bond to form a less saturated heterocyclic ring. Unless otherwise indicated, heterocyclic rings and ring systems can be attached through any available carbon or nitrogen by replacement of a hydrogen on said carbon or nitrogen. In the above recitations, when a compound of Formula 1 is comprised of one or more heterocyclic rings, all substituents are attached to these rings through any available carbon or nitrogen by replacement of a hydrogen on said carbon or nitrogen.

One skilled in the art will appreciate that not all nitrogen-containing heterocycles can form N-oxides since the nitrogen requires an available lone pair of electrons for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "halocycloalkyl", "haloalkoxy", "haloalkylthio", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The total number of carbon atoms in a substituent group is indicated by the "$C_i$-$C_j$" prefix where i and j are numbers from 1 to 10. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. $C_2$ alkylaminoalkyl designates $CH_3NHCH_2$—; $C_3$ alkylaminoalkyl designates, for example, $CH_3(CH_3NH)CH$—, $CH_3NHCH_2CH_2$— or $CH_3CH_2NHCH_2$—; and Examples of "alkylcarbonyl" include $C(O)CH_3$, $C(O)CH_2CH_2CH_3$ and $C(O)CH(CH_3)_2$. Examples of "alkoxycarbonyl" include $CH_3C(=O)$, $CH_3CH_2C(=O)$, $CH_3CH_2CH_2C(=O)$, $(CH_3)_2CHOC(=O)$ and the different butoxy- or pentoxycarbonyl isomers. Examples of "alkylaminocarbonyl" include $CH_3NHC(=O)$—, $CH_3CH_2NHC(=O)$—, $CH_3CH_2CH_2NHC(=O)$—, $(CH_3)_2CHNHC(=O)$— and the different butylamino- or pentylaminocarbonyl isomers. Examples of "dialkylaminocarbonyl" include $(CH_3)_2NC(=O)$—, $(CH_3CH_2)_2NC(=O)$—, $CH_3CH_2(CH_3)NC(=O)$—, $(CH_3)_2CHN(CH_3)C(=O)$— and $CH_3CH_2CH_2(CH_3)NC(=O)$—.

The dotted line in Formula 1 represents that the bond indicated can be a single bond or double bond.

When a compound is substituted with a substituent bearing a subscript that indicates the number of said substituents can vary, when the number of said substituents is greater than 1, said substituents are independently selected from the group of defined substituents. Further, when the subscript indicates a range, e.g. $(R)_{i-j}$, then the number of substituents may be selected from the integers between i and j inclusive. Also, one skilled in the art recognizes that the number of available points of attachment places a limit on the number of substituents possible that may be lower than the broad definition; for example, the subscript "k" in U-16, U-17, U-18, U-19, U-32, U-33 and U-35 shown in Embodiment 14 cannot be greater than 1.

When a group contains a substituent which can be hydrogen, for example $Q^a$, $R^5$, $R^{15}$, $R^{17}$ $R^{18}$ or $R^{19}$, then, when this substituent is taken as hydrogen, it is recognized that this is equivalent to said group being unsubstituted. When a variable group is shown to be optionally attached to a position, for example $(R^2)_n$ wherein n may be 0, then hydrogen may be at the position even if not recited in the variable group definition. When a position on a group is said to be "not substituted" or "unsubstituted", then hydrogen atoms are attached to take up any free valency. The term "optionally substituted" in connection with groups listed for $R^1$, $R^2$, $R^5$, $R^6$, $R^{15}$, $R^{16}$, $R^{16a}$, G, $Q^a$ and $Q^b$ refers to groups that are unsubstituted or have at least 1 non-hydrogen substituent. These groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

As noted above, $R^1$ is an optionally substituted phenyl or 5- or 6-membered heteroaromatic ring; G is an optionally substituted 5-membered heteroaromatic ring or 5-membered saturated or partially saturated heterocyclic ring; $Q^a$ and $Q^b$ are taken together with the nitrogen atom to which they are bonded to form an optionally substituted 5- to 7-membered saturated or partially saturated heterocyclic ring; and $R^6$ is an optionally substituted phenyl, benzyl, naphthalenyl, $C_3$-$C_6$ cycloalkyl, $C_3$-$C_6$ cycloalkenyl or 5- or 6-membered heteroaromatic ring; and Q-2 through Q-85 are optionally substituted. The term "substituted" in connection with these $R^1$, G, $R^6$, $Q^a$ and $Q^b$ groups refers to groups that have at least one non-hydrogen substituent that does not extinguish the fungicidal activity. Since these groups are optionally substituted, they need not have any non-hydrogen substituents.

Naming of substituents in the present disclosure uses recognized terminology providing conciseness in precisely conveying to those skilled in the art the chemical structure. For example, as is used in nomenclature, the prefix "per" indicates "completely", and "perhydro" means that the referenced heteroaromatic ring or ring system (e.g., quinoline, isoquinoline) has been completely hydrogenated, so that it is fully saturated. Also, ending a heterocyclic substituent name with the letter "o" (e.g., "piperidino", "pyrrolidino", "isoquinolino", "isoindolo") means that the heterocyclic substituent is bonded to the remainder of the molecule through the nitrogen atom of the heterocycle. For sake of conciseness, locant descriptors may be omitted; "pyrazol-1-yl" means "1H-pyrazol-1-yl" according to the Chemical Abstracts system of nomenclature. The term "pyridyl" is synonymous with "pyridinyl". The order of listing substituents may be different from the Chemical Abstracts system if the difference does not affect the meaning.

A. Examples of compounds of Formula 1 include compounds wherein $R^1$ is a phenyl or 5- or 6-membered heteroaromatic ring, optionally substituted with 1 to 2 substituents independently selected from $R^4$;

each $R^4$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;

each $R^3$ is independently $C_1$-$C_3$ alkyl, $C_1$-$C_3$ haloalkyl or halogen;

$R^{11}$ is $C_1$-$C_3$ alkyl; and

Q is a radical selected from Q-1 through Q-85 as described in connection with Embodiment 50 described hereinafter.

B. Of note are compounds of Paragraph A above wherein $R^1$ is one of U-1 through U-50 as described in connection with Embodiment 14 described hereinafter; G is one of G-1 through G-55 as described in connection with Embodiment 36 described hereinafter; each $R^{3a}$ is independently H, $C_1$-$C_3$ alkyl, $C_1$-$C_3$ haloalkyl or halogen (more particularly H, $C_1$-$C_3$ alkyl or halogen, and most particularly H or $C_1$-$C_3$ alkyl); $R^{11a}$ is H or $C_1$-$C_3$ alkyl; $R^6$ is one of H-1 through H-46 as described in connection with Embodiment 65 described hereinafter; and $R^{12}$ is H or $C_1$-$C_3$ alkyl. Of particular note among these compounds are compounds wherein each $R^4$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; $R^5$ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano or $C_2$-$C_4$ alkoxyalkyl; and each $R^7$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy or $C_2$-$C_4$ alkylcarbonyloxy; each $R^9$ is independently $C_1$-$C_3$ alkyl, cyclopropyl, $C_1$-$C_3$ haloalkyl, halocyclopropyl, halogen, hydroxy, $C_2$-$C_3$ alkylcarbonyloxy, $C_1$-$C_2$ alkoxy or $C_1$-$C_2$ haloalkoxy; $R^{10}$ is H or methyl; each $R^{16}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; or a phenyl or benzyl ring, optionally substituted with up to 3 substituents selected from $R^{13}$; $R^{16a}$ is H, $C_1$-$C_3$ alkyl, allyl, propargyl, cyclopropyl or $C_1$-$C_3$ haloalkyl; or a phenyl or benzyl ring, optionally substituted with up to 3 substituents selected from $R^{13}$; and each $R^{13}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; A is $NR^{18}$ or $C_1$-$C_2$ alkylene optionally substituted with $R^{17}$; $R^{17}$ is H, halogen, cyano, hydroxy, —CHO, $C_1$-$C_4$ alkyl, $C_2$-$C_4$ alkoxyalkyl, $C_2$-$C_4$ alkylcarbonyl or $C_2$-$C_5$ alkoxycarbonyl; and $R^{18}$ is H, cyano, hydroxy, —CHO, $C_1$-$C_4$ alkyl, $C_2$-$C_4$ alkoxyalkyl, $C_2$-$C_4$ alkylcarbonyl, $C_2$-$C_5$ alkoxycarbonyl or $C_1$-$C_4$ alkylsulfonyl; Z is C=$W^2$ or $C_1$-$C_2$ alkylene optionally substituted with $R^{19}$; and $R^{19}$ is H, halogen, cyano, hydroxy, —CHO, $C_1$-$C_4$ alkyl, $C_1$-$C_4$ haloalkyl, $C_2$-$C_4$ alkylcarbonyl or $C_2$-$C_5$ alkoxycarbonyl.

C. Examples of the compounds of the Paragraph B above include compounds wherein X is one of $X^1$, $X^2$ and $X^3$; and each $R^2$ is independently $C_1$-$C_2$ alkyl, $C_1$-$C_2$ haloalkyl, $C_1$-$C_2$ alkoxy, halogen, cyano or hydroxy; $Q^a$ is H or $CH_3$; and $R^{15}$ is H or $CH_3$; A is $NR^{18}$ or methylene optionally substituted with $R^{17}$; $R^{17}$ is H, halogen, cyano, —CHO, $C_1$-$C_2$ alkyl, $C_2$-$C_3$ alkoxyalkyl, $C_2$-$C_3$ alkylcarbonyl or $C_2$-$C_3$ alkoxycarbonyl; and $R^{18}$ is H, cyano, hydroxy, —CHO, $C_1$-$C_2$ alkyl, $C_2$-$C_3$ alkoxyalkyl, $C_2$-$C_3$ alkylcarbonyl or $C_2$-$C_3$ alkoxycarbonyl; Z is C=W² or methylene optionally substituted with R¹⁹; and R¹⁹ is H, halogen, cyano, $C_1$-$C_2$ alkyl or $C_1$-$C_2$ haloalkyl.

D. Examples of the compounds of the Paragraph C above include compounds wherein R¹ is one of U-1 through U-3, U-11, U-13, U-20, U-22, U-23, U-36, U-37 through U-39 and U-50; and each R⁴ is independently halogen, $C_1$-$C_3$ alkyl, $C_1$-$C_3$ haloalkyl, $C_1$-$C_2$ alkoxy or $C_1$-$C_2$ haloalkoxy. Also included are compounds wherein G is G-1, G-2, G-3, G-7, G-8, G-10, G-11, G-14, G-15, G-23, G-24, G-26, G-27, G-28, G-30, G-36, G-37, G-38 or G-49 through G-55; $R^{3a}$ is H, CH₃, Cl or Br; R¹¹ is CH₃ and R¹¹ is H or CH₃. Of note are compounds wherein G is G-1, G-2, G-7, G-8, G-14, G-15, G-23, G-24, G-26, G-27, G-36, G-37, G-38, G-49 or G-50 (including e.g., where G is unsubstituted); R¹⁷ is H, $C_1$-$C_2$ alkyl, $C_2$-$C_3$ alkylcarbonyl or $C_2$-$C_3$ alkoxycarbonyl; R¹⁸ is H, —CHO, $C_1$-$C_2$ alkyl, $C_2$-$C_3$ alkylcarbonyl or $C_2$-$C_3$ alkoxycarbonyl; and R¹⁹ is H, $C_1$-$C_2$ alkyl or $C_1$-$C_2$ haloalkyl.

E. Further examples of the compounds of Paragraph C include compounds wherein Q is Q-1, Q-2, Q-3, Q-4, Q-8, Q-9, Q-10, Q-12, Q-14, Q-22, Q-23, Q-24, Q-40, Q-41, Q-59, Q-62, Q-74 or Q-84; R⁵ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano or $C_2$-$C_4$ alkoxyalkyl; R⁶ is H-1, H-20, H-32, H-45 or H-46; each R⁷ is independently halogen, $C_1$-$C_3$ alkyl, $C_1$-$C_3$ haloalkyl, $C_1$-$C_2$ alkoxy or $C_1$-$C_2$ haloalkoxy; each R⁸ is independently $C_1$-$C_2$ alkyl, $C_1$-$C_2$ haloalkyl, $C_1$-$C_2$ alkoxy, $C_1$-$C_2$ haloalkoxy, $C_2$-$C_4$ alkylcarbonyloxy or hydroxy; and each R⁹ is independently halogen, hydroxy, OCH₃ or CH₃. Included are compounds wherein Q is Q-1, Q-2, Q-8, Q-14, Q-23, Q-41, Q-59 or Q-62; $Q^a$ is methyl; R⁵ is $C_1$-$C_4$ alkyl, $C_1$-$C_4$ haloalkyl, $C_2$-$C_4$ alkenyl, $C_2$-$C_4$ haloalkenyl or cyano; R⁶ is H-1 or H-45; R¹² is H or CH₃; each R⁷ is independently F, Cl, Br, OCH₃ or methyl; R¹⁵ is H; R⁸ is CH₃, OCH₃ or OH; and R¹⁰ is H or CH₃.

F. Additional examples of the compounds of Paragraph C include compounds wherein W¹ and W² are independently 0; $Q^a$ is CH₃; m, j, n and p are all independently 0 or 1; $R^{3a}$ is H; each R⁷ is independently F, Cl, Br, OCH₃ or methyl; each R⁸ is independently $C_1$-$C_2$ alkyl, $C_1$-$C_2$ alkoxy or hydroxy; and each R⁹ is independently F, Cl, Br, hydroxy, OCH₃ or CH₃. Included are compounds wherein R¹ is U-1 or U-50; each R⁴ is independently halogen, $C_1$-$C_3$ alkyl, $C_1$-$C_3$ haloalkyl or $C_1$-$C_2$ alkoxy; G is G-1, G-2, G-15, G-26, G-27, G-36, G-37 or G-38; Q is Q-1, Q-2, Q-8, Q-23 or Q-41; R⁵ is $C_1$-$C_4$ alkyl, $C_2$-$C_4$ alkenyl or cyano; R⁶ is H-45; and each R⁴ is independently connected to the 3- or 5-position of U-1, each R⁴ is independently connected to the 3- and 5-position of U-1, each R⁴ is independently connected to the 2- or 3-position of U-50, or each R⁴ is independently connected to the 2- and 5-position of U-50 (e.g., compounds where X is X¹ and G is G-1; X is X¹ and G is G-2; X is X¹ and G is G-15; X is X¹ and G is G-26; X is X¹ and G is G-36; X is X² and G is G-1; or X is X² and G is G-2). In the foregoing, "each R⁴ is independently connected to the 3- or 5-position of U-1" means k is 1 and R⁴ is connected to the 3- or 5-position of U-1, "each R⁴ is independently connected to the 3- and 5-position of U-1" means k is 2 and an independently selected R⁴ is connected to each of the 3- and 5-positions of U-1, "each R⁴ is independently connected to the 2- or 3-position of U-50" means k is 1 and R⁴ is connected to the 3- or 5-position of U-50, and "each R⁴ is independently connected to the 2- and 5-position of U-50" means k is 2 and an independently selected R⁴ is connected to each of the 2- and 5-positions of U-50.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds of Formula 1, N-oxides or salts thereof. The compounds of the invention may be present as a mixture of stereoisomers, individual stereoisomers, or as an optically active form. For example, when Q is Q-1, and R⁵, R⁶ and R¹⁵ of Q-1 in Formula 1 are different, then Formula 1 possesses a chiral center at the carbon atom to which they are commonly bonded. This invention comprises racemic mixtures. In addition, this invention includes compounds that are enriched compared to the racemic mixture in an enantiomer of Formula 1.

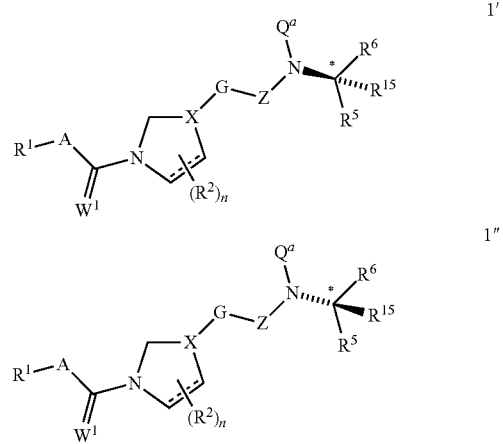

Included are the essentially pure enantiomers of compounds of Formula 1, for example, Formula 1' and Formula 1" wherein Q is Q-1.

When enantiomerically enriched, one enantiomer is present in greater amounts than the other, and the extent of enrichment can be defined by an expression of enantiomeric excess ("ee"), which is defined as (2x−1) 100%, where x is the mole fraction of the dominant enantiomer in the mixture (e.g., an ee of 20% corresponds to a 60:40 ratio of enantiomers).

For the compounds of Formula 1 where Q is Q-1 through Q-74, the more fungicidally active enantiomer is believed to be that wherein R¹⁵ is a hydrogen, the hydrogen atom attached to the carbon atom identified with an asterisk (*) is below the plane defined by the 3 non-hydrogen atoms attached to the carbon atom identified with the asterisk (*) as in Formula 1' (with the aromatic ring of Q-2 through Q-74 positioned with respect to the carbon atom identified with an asterisk (*) in a manner analogous to R⁶ in Q-1 in Formula 1'). For example when R⁵ is CH₃, R⁶ is phenyl and R¹⁵ is H, Formula 1' has the R configuration at the carbon atom to which R⁵, R⁶ and R¹⁵ are commonly bonded.

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, the substituents $R^4$, $R^5$, $R^7$, $R^8$, $R^9$, $R^{13}$, $R^{15}$, $R^{16}$, $R^{16a}$, $R^{17}$, $R^{18}$, $R^{19}$, $Q^a$, $Q^b$ and $X^1$ through $X^8$ may themselves contain chiral centers. This invention comprises racemic mixtures as well as enriched and essentially pure stereoconfigurations at these additional chiral centers.

Compounds of this invention can exist as one or more conformational isomers due to the amide bonds in the compounds of Formula 1 as known by one skilled in the art. This invention comprises mixtures of conformational isomers. In addition, this invention includes compounds that are enriched compared to the mixture of a conformer of Formula 1.

One skilled in the art recognizes that because in the environment and under physiological conditions salts of chemical compounds are in equilibrium with their corresponding non-salt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention include:

Embodiment 1

A compound of Formula 1 wherein A is $NR^{18}$.

Embodiment 1a

A compound of Embodiment 1 wherein $R^{18}$ is H, cyano, hydroxy, —CHO, $C_1$-$C_4$ alkyl, $C_2$-$C_4$ alkoxyalkyl, $C_2$-$C_4$ alkylcarbonyl, $C_2$-$C_5$ alkoxycarbonyl or $C_1$-$C_4$ alkylsulfonyl.

Embodiment 1b

A compound of Embodiment 1a wherein $R^{18}$ is H, cyano, hydroxy, —CHO, $C_1$-$C_2$ alkyl, $C_2$-$C_3$ alkoxyalkyl, $C_2$-$C_3$ alkylcarbonyl or $C_2$-$C_3$ alkoxycarbonyl.

Embodiment 1c

A compound of Embodiment 1b wherein $R^{18}$ is H, —CHO, $C_1$-$C_2$ alkyl, $C_2$-$C_3$ alkylcarbonyl or $C_2$-$C_3$ alkoxycarbonyl.

Embodiment 2

A compound of Formula 1 wherein A is $C_1$-$C_3$ alkylene optionally substituted with 1-3 substituents independently selected from $R^{17}$.

Embodiment 2a

A compound of Embodiment 2 wherein A is $C_1$-$C_2$ alkylene optionally substituted with $R^{17}$ and $R^{17}$ is H, halogen, cyano, hydroxy, —CHO, $C_1$-$C_4$ alkyl, $C_2$-$C_4$ alkoxyalkyl, $C_2$-$C_4$ alkylcarbonyl or $C_2$-$C_5$ alkoxycarbonyl.

Embodiment 2b

A compound of Embodiment 2a wherein A is methylene optionally substituted with $R^{17}$ and $R^{17}$ is H, halogen, cyano, —CHO, $C_1$-$C_2$ alkyl, $C_2$-$C_3$ alkoxyalkyl, $C_2$-$C_3$ alkylcarbonyl or $C_2$-$C_3$ alkoxycarbonyl.

Embodiment 2c

A compound of Embodiment 2b wherein $R^{17}$ is H, $C_1$-$C_2$ alkyl, $C_2$-$C_3$ alkylcarbonyl or $C_2$-$C_3$ alkoxycarbonyl.

Embodiment 3

A compound of Formula 1 wherein $W^1$ is O.

Embodiment 4

A compound of Formula 1 wherein $W^1$ is S.

Embodiment 5

A compound of Formula 1 wherein Z is $C{=}W^2$.

Embodiment 5a

A compound of Embodiment 5 wherein $W^2$ is O.

Embodiment 5b

A compound of Embodiment 5 wherein $W^2$ is S.

Embodiment 6

A compound of Formula 1 wherein Z is $C_1$-$C_3$ alkylene optionally substituted with 1-3 substituents independently selected from $R^{19}$.

Embodiment 6a

A compound of Embodiment 6 wherein Z is $C_1$-$C_2$ alkylene optionally substituted with $R^{19}$ and $R^{19}$ is H, halogen, cyano, hydroxy, —CHO, $C_1$-$C_4$ alkyl, $C_1$-$C_4$ haloalkyl, $C_2$-$C_4$ alkylcarbonyl or $C_2$-$C_5$ alkoxycarbonyl.

Embodiment 6b

A compound of Embodiment 6a wherein Z is methylene optionally substituted with $R^{19}$ and $R^{19}$ is H, halogen, cyano, $C_1$-$C_2$ alkyl or $C_1$-$C_2$ haloalkyl.

Embodiment 6c

A compound of Embodiment 6b wherein $R^{19}$ is H, $C_1$-$C_2$ alkyl or $C_1$-$C_2$ haloalkyl.

Embodiment 7

A compound of Formula 1 wherein $R^2$ is methyl.

Embodiment 8

A compound of Formula 1 wherein n is 0 or 1.

Embodiment 9

A compound of Embodiment 8 wherein n is 0.

Embodiment 10

A compound of Formula 1 wherein X is $X^1$, $X^2$ or $X^3$.

Embodiment 11

A compound of Embodiment 10 wherein X is $X^1$ or $X^2$ and each ring is saturated.

Embodiment 12

A compound of Embodiment 10 wherein X is $X^1$.

Embodiment 13

A compound of Embodiment 12 wherein X is $X^1$ and the ring is saturated.

Embodiment 14

A compound of Formula 1 wherein $R^1$ is one of U-1 through U-50;

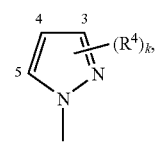
U-1

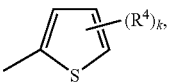
U-2

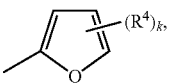
U-3

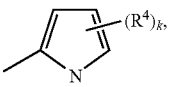
U-4

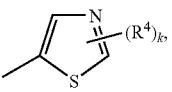
U-5

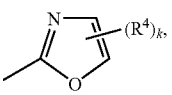
U-6

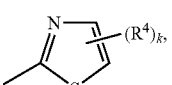
U-7

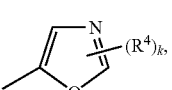
U-8

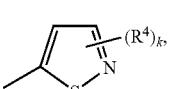
U-9

-continued

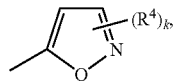
U-10

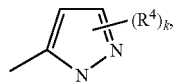
U-11

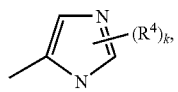
U-12

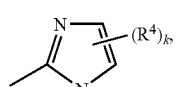
U-13

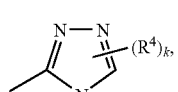
U-14

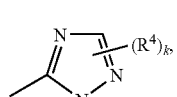
U-15

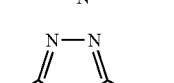
U-16

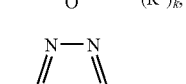
U-17

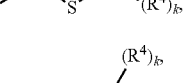
U-18

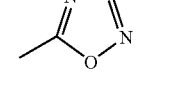
U-19

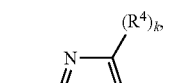
U-20

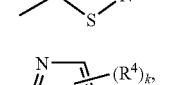
U-21

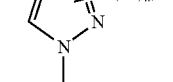
U-22

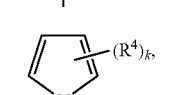
U-23

| | |
|---|---|
| 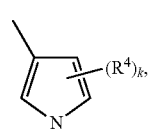 U-24 | 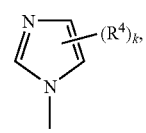 U-36 |
| 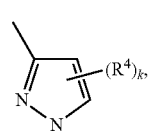 U-25 | 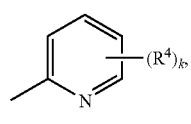 U-37 |
| 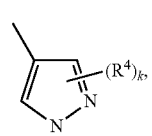 U-26 | 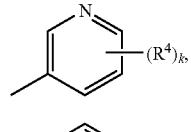 U-38 |
| 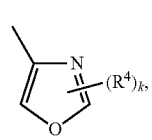 U-27 | 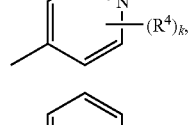 U-39 |
| 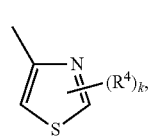 U-28 | 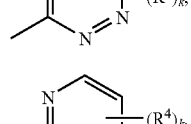 U-40 |
| 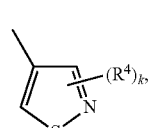 U-29 | 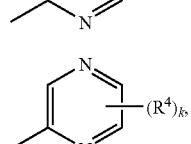 U-41 |
| 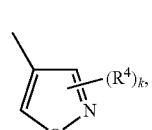 U-30 | 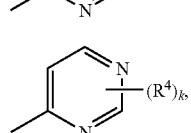 U-42 |
| 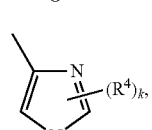 U-31 | 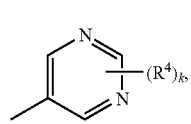 U-43 |
| 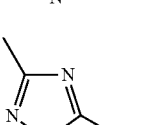 U-32 | 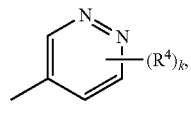 U-44 |
| 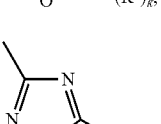 U-33 | 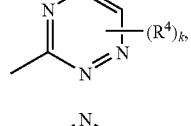 U-45 |
| 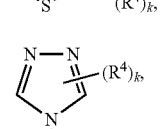 U-34 | 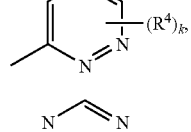 U-46 |
| 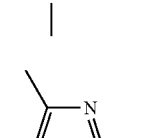 U-35 | 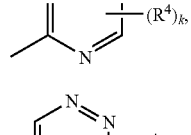 U-47 |

-continued

U-50

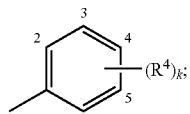

wherein k is 0, 1 or 2;

provided that when U is U-4, U-11 through U-15, U-24 through U-26, U-31 and U-35, and an $R^4$ radical is attached to a nitrogen atom of the ring, then said $R^4$ radical is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl or $C_2$-$C_4$ alkoxyalkyl.

Embodiment 15

A compound of Embodiment 14 wherein $R^1$ is selected from U-1 through U-5, U-8, U-11, U-13, U-15, U-20 through U-28, U-31, U-36 through U-39 and U-50.

Embodiment 16

A compound of Embodiment 15 wherein $R^1$ is selected from U-1 through U-3, U-5, U-8, U-13, U-20, U-22, U-23, U-25 through U-28, U-36 through U-39 and U-50.

Embodiment 17

A compound of Embodiment 16 wherein $R^1$ is selected from U-1 through U-3, U-13, U-20, U-22, U-23, U-36 through U-39 and U-50.

Embodiment 18

A compound of Embodiment 17 wherein $R^1$ is U-1 or U-50.

Embodiment 19

A compound of Embodiment 18 wherein $R^1$ is U-1.

Embodiment 19a

A compound of any one of Formula 1 and Embodiments 18 wherein X is $X^1$, $X^2$ or $X^3$; each $R^2$ is independently $C_1$-$C_3$ alkyl; G is an optionally substituted 5-membered heteroaromatic ring containing 1 to 3 heteroatoms selected from 0 to 1 O, 0 to 1 S and 0 to 3 N; $Q^a$ is $CH_3$; and $Q^b$ is radical selected from

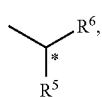
$Q^b$-1

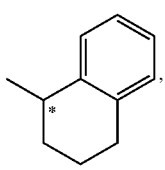
$Q^b$-2

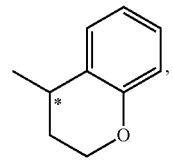
$Q^b$-3

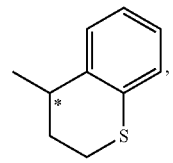
$Q^b$-4

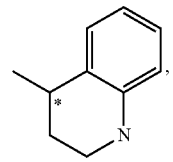
$Q^b$-5

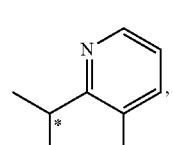
$Q^b$-6

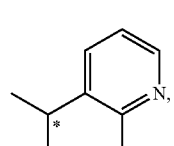
$Q^b$-7

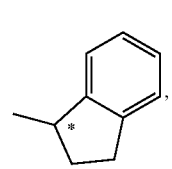
$Q^b$-8

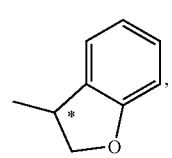
$Q^b$-9

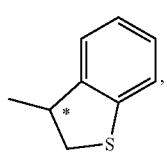
$Q^b$-10

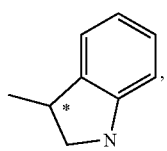
$Q^b$-11

-continued

Q$^b$-12
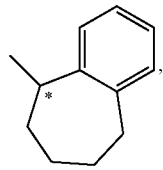

Q$^b$-13
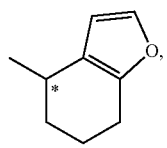

Q$^b$-14
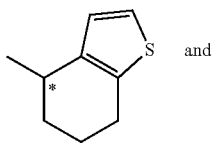  and

Q$^b$-15
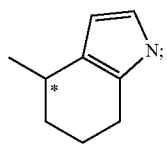;

wherein Q$^b$-2 through Q$^b$-15 are optionally substituted except at the carbon atom identified with an asterisk (*); R$^5$ is C$_1$-C$_6$ alkyl, C$_2$-C$_6$ alkenyl, C$_2$-C$_6$ alkynyl, C$_3$-C$_6$ cycloalkyl, C$_1$-C$_6$ haloalkyl, C$_2$-C$_6$ haloalkenyl, C$_2$-C$_6$ haloalkynyl, C$_3$-C$_6$ halocycloalkyl, cyano, nitro, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylaminocarbonyl, C$_3$-C$_8$ dialkylaminocarbonyl or C$_3$-C$_6$ trialkylsilyl; and R$^6$ is an optionally substituted phenyl, naphthalenyl or 5- or 6-membered heteroaromatic ring.

Embodiment 20

A compound of Embodiment 18 wherein R$^1$ is U-50.

Embodiment 21

A compound of Formula 1 wherein R$^1$ is a phenyl or 5- or 6-membered heteroaromatic ring, each optionally substituted with 1 to 2 substituents independently selected from R$^4$; and each R$^4$ is independently C$_1$-C$_3$ alkyl, C$_2$-C$_3$ alkenyl, C$_2$-C$_3$ alkynyl, cyclopropyl, C$_1$-C$_3$ haloalkyl, C$_2$-C$_3$ haloalkenyl, C$_2$-C$_3$ haloalkynyl, halocyclopropyl, halogen, cyano, nitro, C$_1$-C$_2$ alkoxy, C$_1$-C$_2$ haloalkoxy, C$_1$-C$_2$ alkylthio, C$_1$-C$_2$ haloalkylthio, C$_1$-C$_2$ alkoxyalkyl, C$_2$-C$_3$ alkylcarbonyl, C$_2$-C$_3$ alkoxycarbonyl, C$_2$-C$_3$ alkylaminocarbonyl or C$_3$-C$_4$ dialkylaminocarbonyl.

Embodiment 22

A compound of Embodiment 21 wherein each R$^4$ is independently C$_1$-C$_3$ alkyl, C$_2$-C$_3$ alkenyl, C$_2$-C$_3$ alkynyl, cyclopropyl, C$_1$-C$_3$ haloalkyl, C$_2$-C$_3$ haloalkenyl, C$_2$-C$_3$ haloalkynyl, halocyclopropyl, halogen, cyano, nitro, C$_1$-C$_2$ alkoxy or C$_1$-C$_2$ haloalkoxy.

Embodiment 23

A compound of Embodiment 22 wherein each R$^4$ is independently halogen, C$_1$-C$_3$ alkyl, C$_1$-C$_3$ haloalkyl, C$_1$-C$_2$ alkoxy or C$_1$-C$_2$ haloalkoxy.

Embodiment 24

A compound of Embodiment 23 wherein each R$^4$ is independently halogen, C$_1$-C$_2$ alkyl, C$_1$-C$_2$ haloalkyl or C$_1$-C$_2$ alkoxy.

Embodiment 25

A compound of Embodiment 24 wherein each R$^4$ is independently Cl, Br, I, methyl, ethyl, trifluoromethyl or methoxy.

Embodiment 26

A compound of Embodiment 25 wherein at least one R$^4$ is Cl.

Embodiment 27

A compound of Embodiment 25 wherein at least one R$^4$ is Br.

Embodiment 28

A compound of Embodiment 25 wherein at least one R$^4$ is methyl.

Embodiment 29

A compound of Embodiment 25 wherein at least one R$^4$ is ethyl.

Embodiment 30

A compound of Embodiment 25 wherein at least one R$^4$ is trifluoromethyl.

Embodiment 31

A compound of Embodiment 25 wherein at least one R$^4$ is methoxy.

Embodiment 32

A compound of Embodiment 19 wherein each R$^4$ is independently connected to the 3- or 5-position of U-1 (i.e. k is 1, and R$^4$ is connected to the 3- or 5-position of U-1).

Embodiment 32a

A compound of Embodiment 19a wherein each R$^4$ is independently connected to the 3- or 5-position of U-1 (i.e. k is 1, and R$^4$ is connected to the 3- or 5-position of U-1); and each R$^4$ is independently C$_1$-C$_6$ alkyl, C$_2$-C$_6$ alkenyl, C$_2$-C$_6$ alkynyl, C$_3$-C$_6$ cycloalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment 33

A compound of Embodiment 19 wherein each $R^4$ is independently connected to the 3- and 5-position of U-1 (i.e. k is 2, and an independently selected $R^4$ is connected to the 3- and 5-positions of U-1). Of note are compounds of Embodiment 33 which correspond to compounds of note for Embodiment 19 above where each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment 34

A compound of Embodiment 20 wherein each $R^4$ is independently connected to the 2- or 3-position of U-50 (i.e. k is 1, and $R^4$ is connected to the 2- or 3-position of U-50).

Embodiment 35

A compound of Embodiment 20 wherein each $R^4$ is independently connected to the 2- and 5-position of U-50 (i.e. k is 2, and an independently selected $R^4$ is connected to each of 2- and 5-positions of U-50).

Embodiment 36

A compound of Formula 1 wherein G is one of G-1 through G-55;

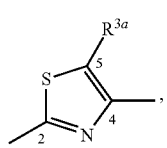
G-1

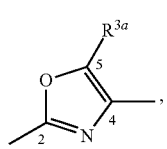
G-2

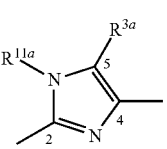
G-3

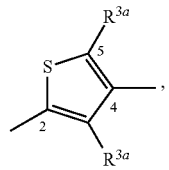
G-4

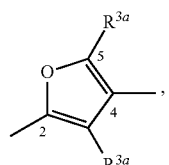
G-5

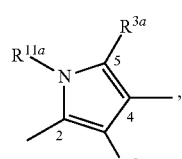
G-6

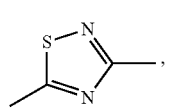
G-7

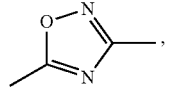
G-8

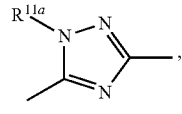
G-9

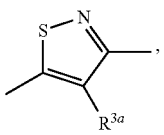
G-10

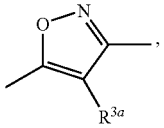
G-11

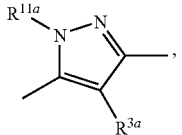
G-12

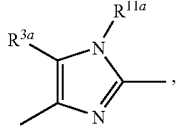
G-13

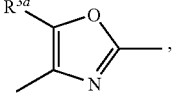
G-14

| | |
|---|---|
| G-15 | 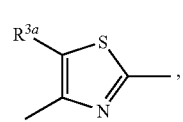 |
| G-16 | 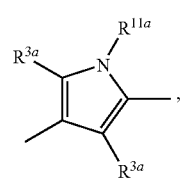 |
| G-17 | 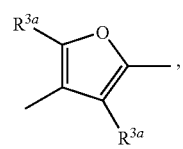 |
| G-18 | 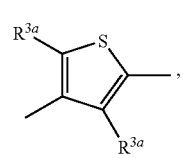 |
| G-19 | 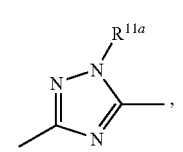 |
| G-20 | 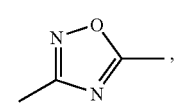 |
| G-21 | 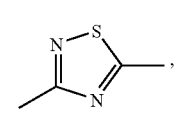 |
| G-22 | 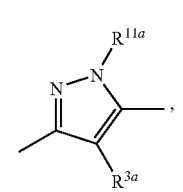 |
| G-23 | 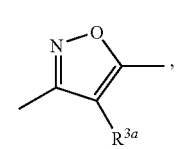 |
| G-24 | 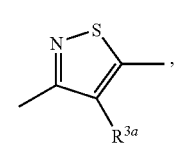 |
| G-25 | 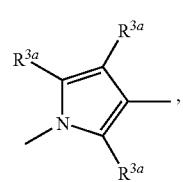 |
| G-26 | 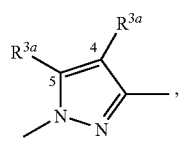 |
| G-27 | 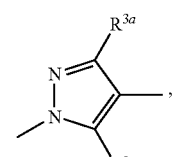 |
| G-28 | 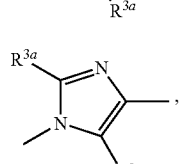 |
| G-29 | 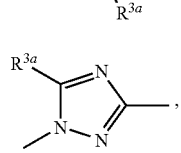 |
| G-30 | 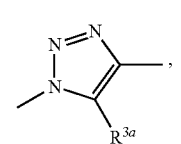 |
| G-31 | 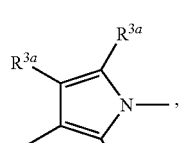 |
| G-32 | 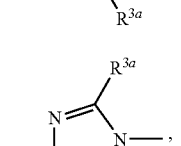 |
| G-33 | 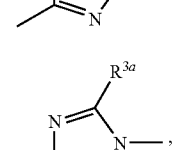 |
| G-34 | 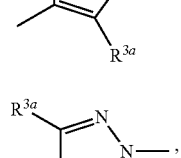 |
| G-35 | 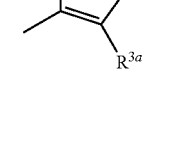 |

G-36 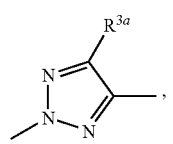

G-37 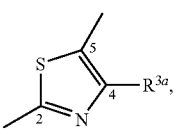

G-38 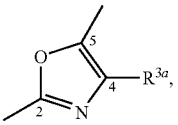

G-39 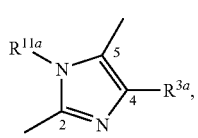

G-40 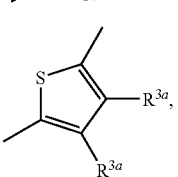

G-41 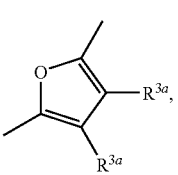

G-42 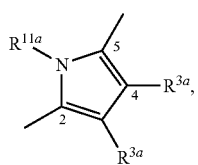

G-43 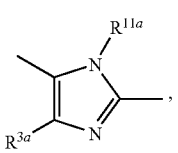

G-44 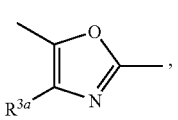

G-45 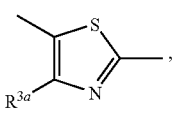

G-46 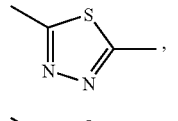

G-47 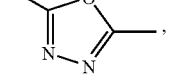

G-48 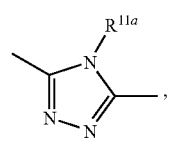

G-49 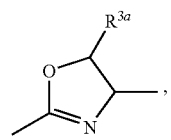

G-50 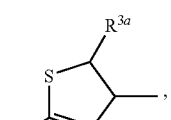

G-51 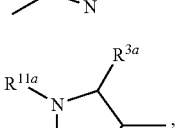

G-52 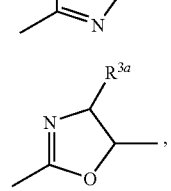

G-53 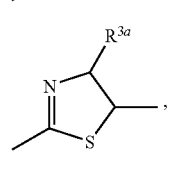

G-54 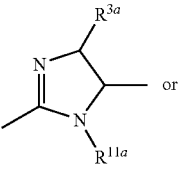 or

G-55 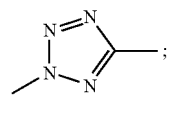;

wherein each $R^3$ is independently $C_1$-$C_3$ alkyl, $C_1$-$C_3$ haloalkyl or halogen; each $R^{3a}$ is independently selected from H or $R^3$; $R^{11}$ is $C_1$-$C_3$ alkyl; $R^{11a}$ is selected from H or $R^{11}$; and the bond projecting to the left is bonded to X, and bond projecting to the right is bonded to Z.

Embodiment 37

A compound of Embodiment 36 wherein G is selected from G-1 through G-3, G-7, G-8, G-10, G-11, G-14, G-15, G-23, G-24, G-26 through G-28, G-30, G-36 through G-38 and G-49 through G-55.

Embodiment 38

A compound of Embodiment 37 wherein G is selected from G-1, G-2, G-7, G-8, G-14, G-15, G-23, G-24, G-26, G-27, G-36 through G-38, G-49, G-50 and G-55.

Embodiment 39

A compound of Embodiment 38 wherein G is selected from G-1, G-2, G-15, G-26, G-27, G-36, G-37 and G-38.

Embodiment 40

A compound of Embodiment 39 wherein G is selected from G-1, G-2, G-15, G-26 and G-36.

Embodiment 41

A compound of Embodiment 36 wherein G is G-1. Of note are embodiments of these compounds within Embodiments 1 through 35, Embodiments 46 through 96, Embodiments A1 through A4, and Embodiments A6 through A13.

Embodiment 42

A compound of Embodiment 36 wherein G is G-2. Of note are embodiments of these compounds within Embodiments 1 through 35, Embodiments 46 through 96, Embodiments A1 through A4, and Embodiments A6 through A13.

Embodiment 43

A compound of Embodiment 36 wherein G is G-15. Of note are embodiments of these compounds within Embodiments 1 through 35, Embodiments 46 through 96, Embodiments A1 through A4, and Embodiments A6 through A13.

Embodiment 44

A compound of Embodiment 36 wherein G is G-26. Of note are embodiments of these compounds within Embodiments 1 through 35, Embodiments 46 through 96, Embodiments A1 through A4, and Embodiments A6 through A13.

Embodiment 45

A compound of Embodiment 36 wherein G is G-36. Of note are embodiments of these compounds within Embodiments 1 through 35, Embodiments 46 through 96, Embodiments A1 through A4, and Embodiments A6 through A13.

Embodiment 46

A compound of Formula 1 wherein G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members; each $R^{11}$ is independently $C_1$-$C_3$ alkyl; each $R^3$ is independently $C_1$-$C_3$ alkyl or halogen.

Embodiment 47

A compound of Embodiment 46 wherein $R^3$ is methyl.

Embodiment 48

A compound of any one of Embodiments 36 through 45 wherein G is unsubstituted.

Embodiment 49

A compound of Embodiment 36 wherein $R^{3a}$ is H and $R^{11a}$ is H or methyl.

Embodiment 50

A compound of Formula 1 wherein Q is selected from Q-1 through Q-85;

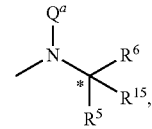
Q-1

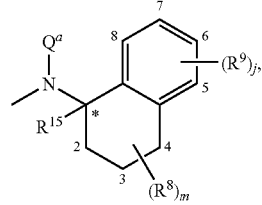
Q-2

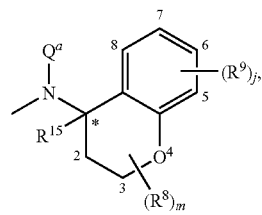
Q-3

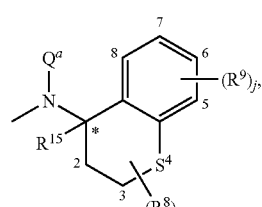
Q-4

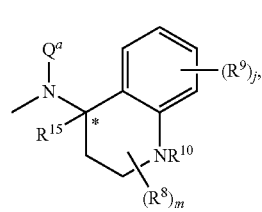
Q-5

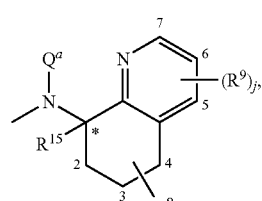
Q-6

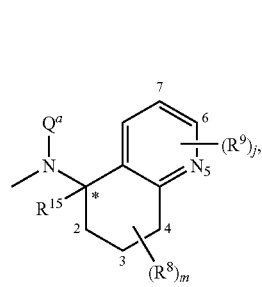
Q-7

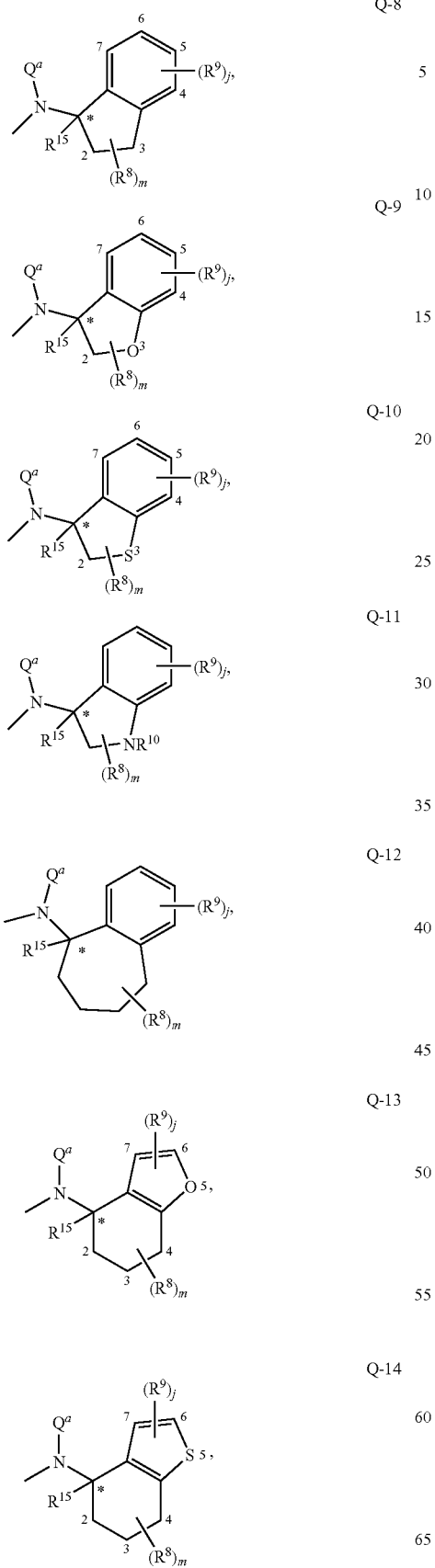
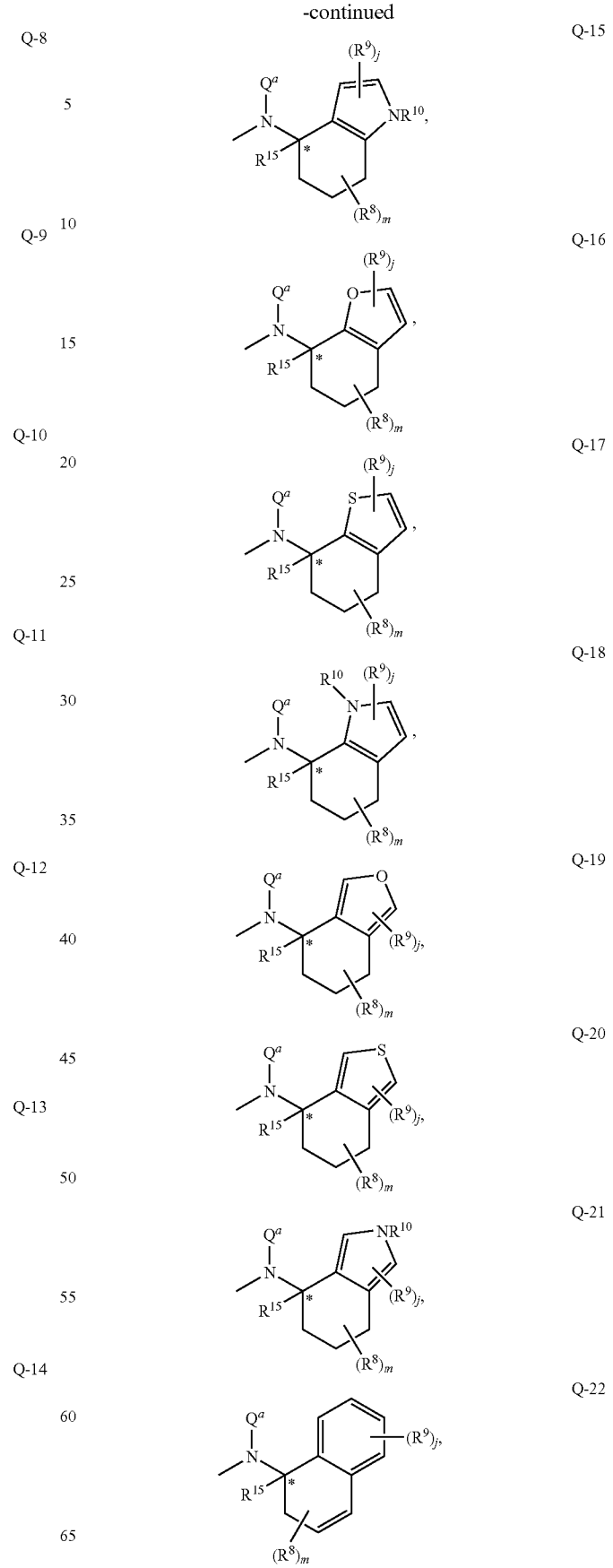

-continued
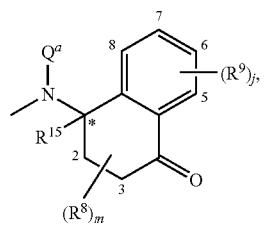 Q-23
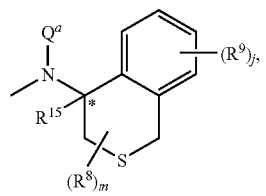 Q-24
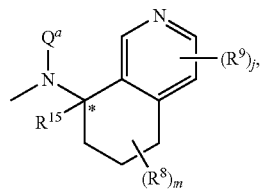 Q-25
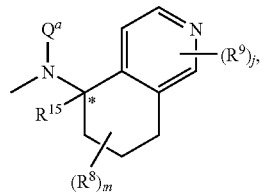 Q-26
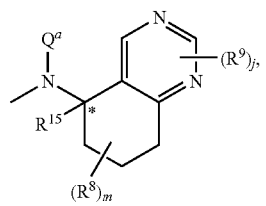 Q-27
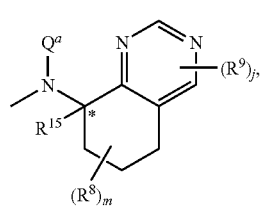 Q-28
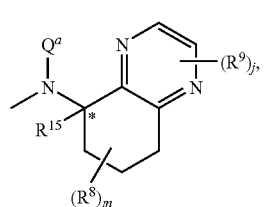 Q-29
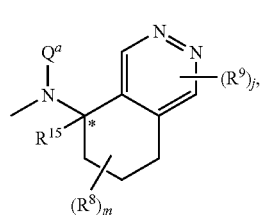 Q-30
-continued
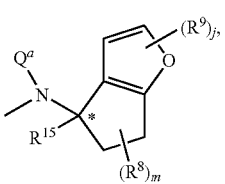 Q-31
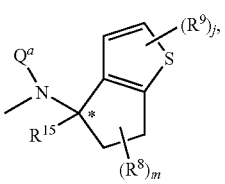 Q-32
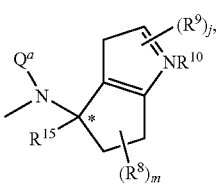 Q-33
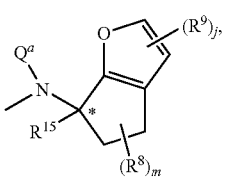 Q-34
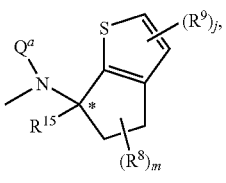 Q-35
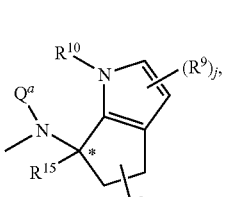 Q-36
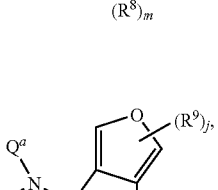 Q-37
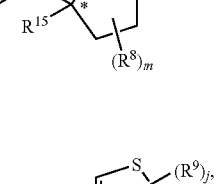 Q-38

-continued
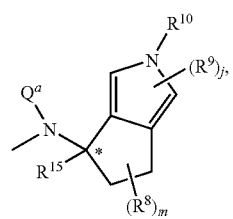 Q-39
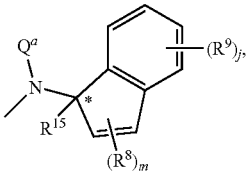 Q-40
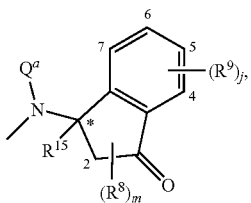 Q-41
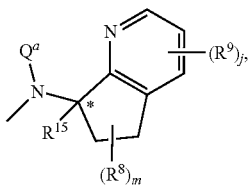 Q-42
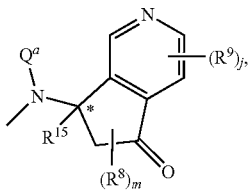 Q-43
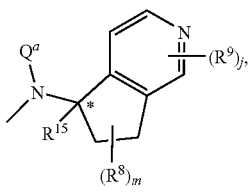 Q-44
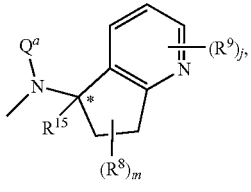 Q-45
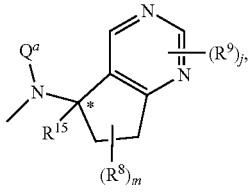 Q-46
-continued
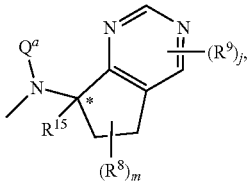 Q-47
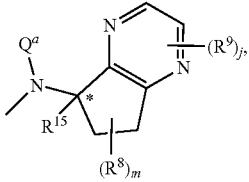 Q-48
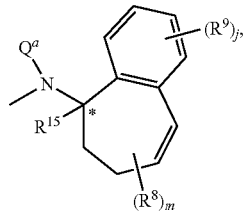 Q-49
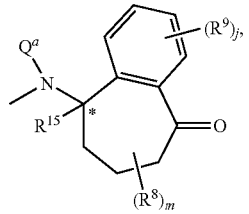 Q-50
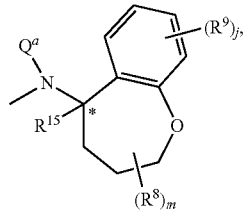 Q-51
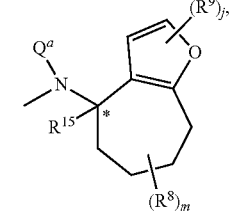 Q-52
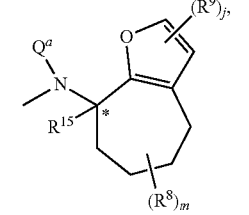 Q-53

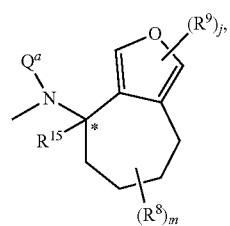 Q-54
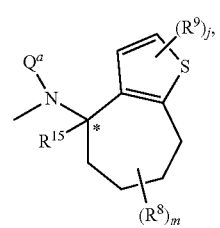 Q-55
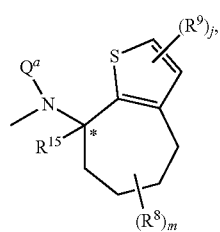 Q-56
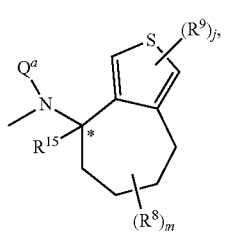 Q-57
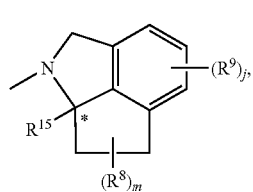 Q-58
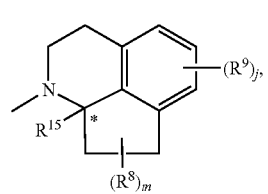 Q-59
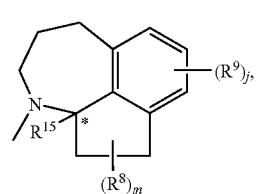 Q-60
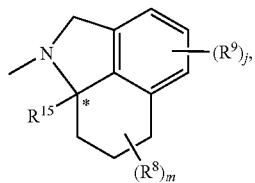 Q-61
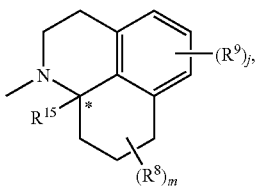 Q-62
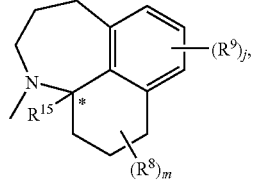 Q-63
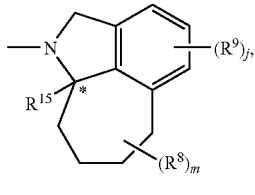 Q-64
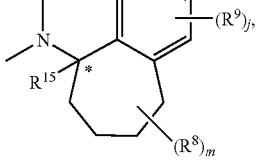 Q-65
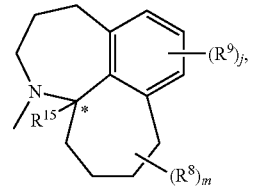 Q-66
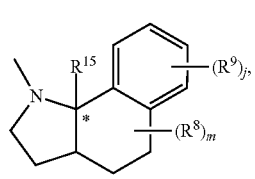 Q-67
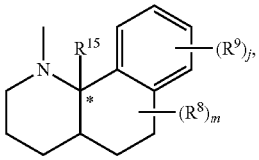 Q-68

-continued

Q-69 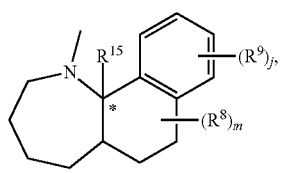

Q-70 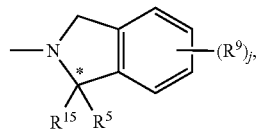

Q-71 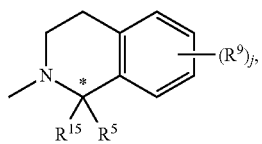

Q-72 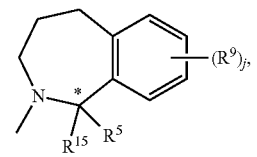

Q-73 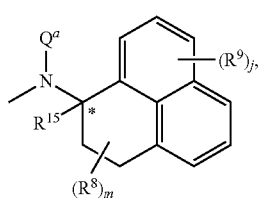

Q-74 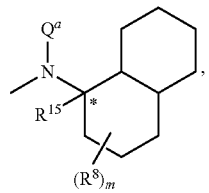

Q-75 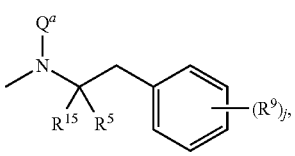

Q-76 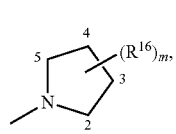

Q-77 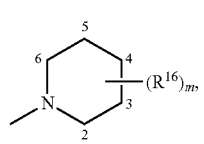

-continued

Q-78 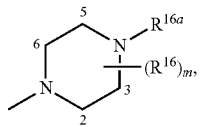

Q-79 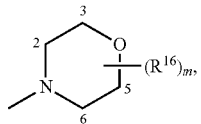

Q-80 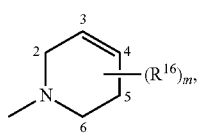

Q-81 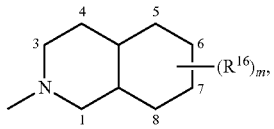

Q-82 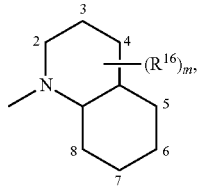

Q-83 

Q-84 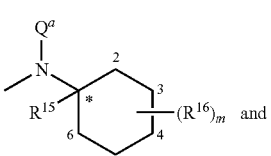 and

Q-85 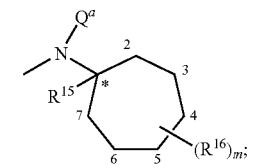;

wherein carbon atom identified with the asterisk (*) contains a stereocenter; $R^{11}$ is as described above, and for Q-2 through Q-75, each $R^8$ is independently attached to the carbon atoms of the nonaromatic carbocyclic ring or heterocyclic ring of the Q group, and each $R^9$ is independently attached to the carbon atoms of phenyl or heteroaromatic ring of the Q group;

each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_6$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_4$ alkoxycarbonyl, $C_2$-$C_4$ alkylcarbonyloxy, $C_2$-$C_4$ alkylcarbonylthio, $C_2$-$C_4$ alkylaminocarbonyl, $C_2$-$C_4$ alkylaminocarbonyloxy, $C_3$-$C_6$ dialkylaminocarbonyl or $C_3$-$C_6$ trialkylsilyl;

each $R^9$ is independently $C_1$-$C_6$ alkyl, $C_2$-$C_6$ alkenyl, $C_3$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

$R^{10}$ is H or $C_1$-$C_3$ alkyl;

m is 0, 1 or 2;

j is 0, 1 or 2;

each $R^{16}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or a phenyl or benzyl ring, optionally substituted with up to 3 substituents selected from $R^{13}$; or two $R^{16}$ attached to adjacent ring carbon atoms are taken together as —$(CH_2)_3$— or —$(CH_2)_4$— optionally substituted with 1-3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

$R^{16a}$ is H, $C_1$-$C_6$ alkyl, $C_3$-$C_6$ alkenyl, $C_3$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_3$-$C_6$ haloalkenyl, $C_3$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylsulfonyl, $C_1$-$C_4$ haloalkylsulfonyl, amino, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylaminocarbonyl or $C_3$-$C_8$ dialkylaminocarbonyl; or a phenyl or benzyl ring, optionally substituted with up to 3 substituents selected from $R^{13}$ each $R^{13}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

$R^6$ is a phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members;

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and $R^{12}$ is H or $C_1$-$C_3$ alkyl.

Embodiment 51

A compound of Formula 1 wherein Q is selected from Q-1 through Q-4, Q-8 through Q-10, Q-12, Q-14, Q-22 through Q-24, Q-40, Q-41, Q-59, Q-62, Q-74 and Q-84.

Embodiment 52

A compound of Embodiment 51 wherein Q is Q-1, Q-2, Q-8, Q-14, Q-23, Q-41, Q-59 or Q-62.

Embodiment 53

A compound of Embodiment 52 wherein Q is Q-1, Q-2, Q-8, Q-23 or Q-41.

Embodiment 54

A compound of Embodiment 53 wherein Q is Q-1.

Embodiment 55

A compound of Embodiment 53 wherein Q is Q-2.

Embodiment 56

A compound of Embodiment 53 wherein Q is Q-8.

Embodiment 57

A compound of Embodiment 53 wherein Q is Q-23.

Embodiment 58

A compound of Embodiment 53 wherein Q is Q-41.

Embodiment 59

A compound of Formula 1 wherein $R^5$ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano, nitro, $C_2$-$C_4$ alkoxyalkyl, $C_2$-$C_6$ alkoxycarbonyl, $C_2$-$C_6$ alkylaminocarbonyl or $C_3$-$C_8$ dialkylaminocarbonyl.

Embodiment 60

A compound of Embodiment 59 wherein $R^5$ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano or $C_2$-$C_4$ alkoxyalkyl.

Embodiment 61

A compound of Embodiment 60 wherein $R^5$ is $C_1$-$C_4$ alkyl, $C_1$-$C_4$ haloalkyl, $C_2$-$C_4$ alkenyl, $C_2$-$C_4$ haloalkenyl or cyano.

Embodiment 62

A compound of Embodiment 61 wherein $R^5$ is $C_1$-$C_4$ alkyl, $C_2$-$C_4$ alkenyl or cyano.

Embodiment 63

A compound of Embodiment 62 wherein $R^5$ is $C_1$-$C_3$ alkyl.

Embodiment 64

A compound of Embodiment 63 wherein $R^5$ is ethyl.

Embodiment 65

A compound of Embodiment 50 wherein $R^6$ is one of H-1 through H-46;

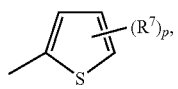  H-1

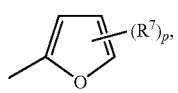  H-2

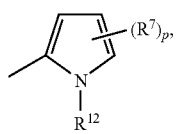  H-3

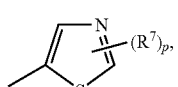  H-4

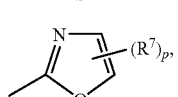  H-5

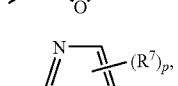  H-6

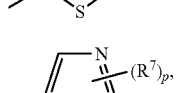  H-7

-continued

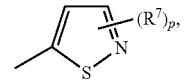  H-8

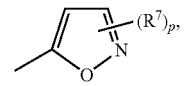  H-9

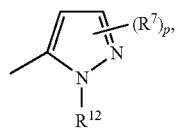  H-10

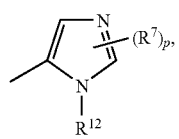  H-11

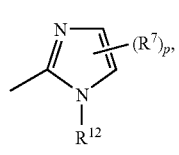  H-12

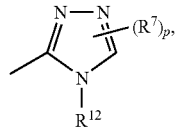  H-13

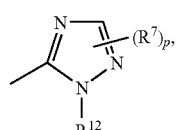  H-14

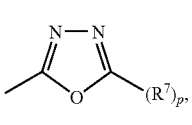  H-15

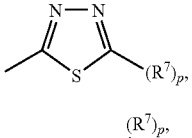  H-16

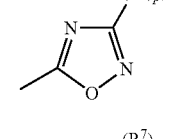  H-17

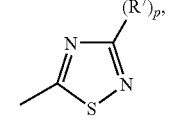  H-18

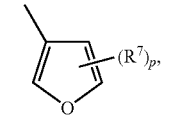  H-19

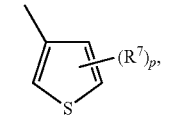  H-20

-continued

H-21, H-22, H-23, H-24, H-25, H-26, H-27, H-28, H-29, H-30, H-31

-continued

H-32, H-33, H-34, H-35, H-36, H-37, H-38, H-39, H-40, H-41, H-42, H-43, H-44, H-45

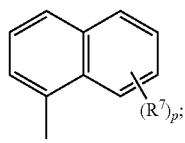

wherein each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and p is 0, 1 or 2.

Embodiment 66

A compound of Embodiment 65 wherein $R^6$ is H-1, H-20, H-32, H-45 or H-46.

Embodiment 67

A compound of Embodiment 66 wherein $R^6$ is H-1 or H-45.

Embodiment 68

A compound of Embodiment 67 wherein $R^6$ is H-45.

Embodiment 69

A compound of Formula 1 wherein $Q^b$ is $CR^5R^6R^{15}$; $R^6$ is a phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members; each $R^7$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, hydroxy, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkylcarbonyloxy, $C_2$-$C_3$ alkoxycarbonyl, $C_2$-$C_3$ alkylaminocarbonyl or $C_3$-$C_4$ dialkylaminocarbonyl; and $R^{12}$ is $C_1$-$C_3$ alkyl.

Embodiment 70

A compound of Embodiment 69 wherein each $R^7$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, hydroxy, $C_1$-$C_2$ alkoxy or $C_1$-$C_2$ haloalkoxy.

Embodiment 71

A compound of Embodiment 70 wherein each $R^7$ is independently halogen, $C_1$-$C_3$ alkyl, $C_1$-$C_3$ haloalkyl, hydroxy, $C_1$-$C_2$ alkoxy or $C_1$-$C_2$ haloalkoxy.

Embodiment 72

A compound of Embodiment 71 wherein each $R^7$ is independently halogen, hydroxy, $C_1$-$C_2$ alkoxy or $C_1$-$C_3$ alkyl.

Embodiment 73

A compound of Embodiment 72 wherein each $R^7$ is independently F, Cl, Br, hydroxy, methoxy or methyl.

Embodiment 74

A compound of Embodiment 65 wherein p is 0.

Embodiment 75

A compound of Embodiment 65 wherein $R^{12}$ is H or $C_1$-$C_2$ alkyl.

Embodiment 76

A compound of Embodiment 75 wherein $R^{12}$ is methyl.

Embodiment 77

A compound of Formula 1 wherein $R^{15}$ is H, $C_1$-$C_4$ alkyl, $C_2$-$C_4$ alkenyl, $C_2$-$C_4$ alkynyl, $C_3$-$C_4$ cycloalkyl or $C_1$-$C_4$ haloalkyl.

Embodiment 78

A compound of Embodiment 77 wherein $R^{15}$ is H or $C_1$-$C_3$ alkyl.

Embodiment 79

A compound of Embodiment 78 wherein $R^{15}$ is H.

Embodiment 80

A compound of Formula 1 wherein $Q^a$ is H or $C_1$-$C_3$ alkyl.

Embodiment 81

A compound of Embodiment 80 wherein $Q^a$ is H or methyl.

Embodiment 82

A compound of Embodiment 81 wherein $Q^a$ is methyl.

Embodiment 83

A compound of Embodiment 50 wherein each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy or $C_2$-$C_4$ alkylcarbonyloxy.

Embodiment 84

A compound of Embodiment 83 wherein each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_3$-$C_6$ halocycloalkyl, halogen, hydroxy, amino, cyano, nitro, $C_1$-$C_4$ alkoxy or $C_2$-$C_4$ alkylcarbonyloxy.

Embodiment 85

A compound of Embodiment 84 wherein each $R^8$ is independently H, $C_1$-$C_3$ alkyl, hydroxy, $C_1$-$C_3$ alkoxy or $C_2$-$C_3$ alkylcarbonyloxy.

Embodiment 86

A compound of Embodiment 85 wherein $R^8$ is H, methyl, methoxy or hydroxy.

Embodiment 87

A compound of Embodiment 50 wherein m is 0 or 1.

Embodiment 88

A compound of Embodiment 87 wherein m is 0.

Embodiment 89

A compound of Embodiment 50 wherein each $R^9$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, hydroxy, $C_2$-$C_3$ alkylcarbonyloxy, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment 90

A compound of Embodiment 89 wherein each $R^9$ is independently $C_1$-$C_3$ alkyl, cyclopropyl, $C_1$-$C_3$ haloalkyl, halocyclopropyl, halogen, hydroxy, $C_2$-$C_3$ alkylcarbonyloxy, $C_1$-$C_2$ alkoxy or $C_1$-$C_2$ haloalkoxy.

Embodiment 91

A compound of Embodiment 90 wherein each $R^9$ is independently $C_1$-$C_3$ alkyl, hydroxy, $C_1$-$C_2$ alkoxy or halogen.

Embodiment 92

A compound of Embodiment 91 wherein each $R^9$ is independently methyl, F, Cl, Br, hydroxy or methoxy.

Embodiment 93

A compound of Embodiment 50 wherein j is 0 or 1.

Embodiment 94

A compound of Embodiment 93 wherein j is 0.

Embodiment 95

A compound of Embodiment 50 wherein each $R^{10}$ is H or methyl.

Embodiment 96

A compound of Formula 1 wherein Q is Q-1 through Q-75 and Q-83 through Q-85 and Q has the orientation depicted above in Embodiment 50, and wherein $R^{15}$ has an orientation below the plane defined by the 3 non-hydrogen atoms attached to the carbon atom identified with the asterisk (*) (e.g., for Q-1, Formula 1').

Embodiment 97

A compound of Embodiment 50 wherein each $R^{16}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; or a phenyl or benzyl ring, optionally substituted with up to 3 substituents selected from $R^{13}$.

Embodiment 98

A compound of Embodiment 50 wherein $R^{16a}$ is H, $C_1$-$C_3$ alkyl, allyl, propargyl, cyclopropyl or $C_1$-$C_3$ haloalkyl; or a phenyl or benzyl ring, optionally substituted with up to 3 substituents selected from $R^{13}$.

Embodiment 99

A compound of Embodiment 50 wherein when Q is Q-76, Q-77, Q-79, Q-80, Q-81, Q-82, Q-83, Q-84 or Q-85, then m is 0 or 1.

Embodiment 100

A compound of Embodiment 99 wherein m is 1.

Embodiment 101

A compound of Embodiment 50 wherein when Q is Q-78 and $R^{16a}$ is other than H, then m is 0.

Embodiment 102

A compound of Embodiment 50 wherein when Q is Q-78 and $R^{16a}$ is H, then m is 1.

Embodiment 103

A compound of Embodiment 50 wherein when Q is Q-78, then $R^{16a}$ is other than H and m is 0.

Embodiments of this invention, including Embodiments 1-103 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-103 above as well as any other embodiments described herein, and any combination thereof, pertain to the compositions and methods of the present invention.

Combinations of Embodiments 1-103 are illustrated by:

Embodiment A1

A compound of Formula 1 wherein n is 0; $R^1$ is a phenyl or 5- or 6-membered heteroaromatic ring, each optionally substituted with 1 to 2 substituents independently selected from $R^4$; and each $R^4$ is independently $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment A2

A compound of Embodiment A1 wherein $W^1$ is O.

Embodiment A3

A compound of Embodiment A2 wherein A is $NR^{18}$ or methylene optionally substituted with $R^{17}$; $R^{17}$ is H, $C_1$-$C_2$ alkyl, $C_2$-$C_3$ alkylcarbonyl or $C_2$-$C_3$ alkoxycarbonyl; $R^{18}$ is H, —CHO, $C_1$-$C_2$ alkyl, $C_2$-$C_3$ alkylcarbonyl or $C_2$-$C_3$ alkoxycarbonyl; Z is C=$W^2$ or methylene optionally substituted with $R^{19}$; $R^{19}$ is H, $C_1$-$C_2$ alkyl or $C_1$-$C_2$ haloalkyl.

Embodiment A4

A compound of Embodiment A3 wherein X is $X^1$ or $X^2$.

Embodiment A5

A compound of Embodiment A4 wherein G is G-1, G-2, G-15, G-26 or G-36.

Embodiment A6

A compound of Embodiment A5 wherein G is unsubstituted.

Embodiment A7

A compound of Embodiment A6 wherein Q is Q-1, Q-2, Q-8, Q-23 or Q-41 and $Q^a$ is H or $C_1$-$C_3$ alkyl.

Embodiment A8

A compound of Embodiment A7 wherein $R^5$ is $C_1$-$C_3$ alkyl, $R^6$ is H-45, $R^{15}$ is H, and p is O.

Embodiment A9

A compound of Embodiment A7 wherein j is 0, m is 0 or 1, and $R^8$ is H, methyl, methoxy or hydroxy.

Embodiment A10

A compound of any one of Embodiments A8 and A9 wherein $R^1$ is U-1 or U-50.

Embodiment A11

A compound of Embodiment A10 wherein each $R^4$ is independently Cl, Br, methyl, ethyl, trifluoromethyl or methoxy.

Embodiment A12

A compound of Embodiment A11 wherein Q is Q-1, $Q^a$ is methyl, $R^5$ is $C_1$-$C_2$ alkyl, $R^{15}$ is H, and the carbon atom to which $R^5$ and $R^6$ are attached is a stereocenter with the R configuration.

Embodiment A13

A compound of Embodiment A11 wherein Q is Q-2, Q-8, Q-23 or Q-41, $Q^a$ is methyl, $R^{15}$ is H, and the carbon atom identified with the asterisk (*) is a stereocenter having a configuration described as R, provided that when m is 1, $R^8$ is hydroxy or methoxy and the $R^8$ group is attached to the carbon adjacent to the carbon atom identified with an asterisk (*), then the carbon atom identified with the asterisk (*) is a stereocenter having a configuration described as S.

Specific embodiments include compounds of Formula 1 selected from the group consisting of:

1-[4-[4-[[methyl[(1R)-1,2,3,4-tetrahydro-1-naphthalenyl]amino]methyl]-2-thiazolyl]-1-piperidinyl]-2-[5-methyl-3-(trifluoromethyl)-1H-pyrazol-1-yl]ethanone (Compound 1), 2-[5-methyl-3-(trifluoromethyl)-1H-pyrazol-1-yl]-1-[4-[4-[[[(1R)-1,2,3,4-tetrahydro-1-naphthalenyl]amino]methyl]-2-thiazolyl]-1-piperidinyl]ethanone (Compound 2), N-[[2-[1-[2-[5-methyl-3-(trifluoromethyl)-1H-pyrazol-1-yl]acetyl]-4-piperidinyl]-4-thiazolyl]methyl]-N-[(1R)-1,2,3,4-tetrahydro-1-naphthalenyl]acetamide (Compound 3), N-[[2-[1-[2-[5-methyl-3-(trifluoromethyl)-1H-pyrazol-1-yl]acetyl]-4-piperidinyl]-4-thiazolyl]methyl]-N-[(1R)-1,2,3,4-tatrahydro-1-naphthalenyl]formamide (Compound 4), N-methyl-2-[1-[3-[5-methyl-3-(trifluoromethyl)-1H-pyrazol-1-yl]-1-oxopropyl]-4-piperidinyl]-N-[(1R)-1,2,3,4-tetrahydro-1-naphthalenyl]-4-thiazolecarboxamide (Compound 5), and ethyl 4-[4-[[methyl(1,2,3,4-tetrahydro-1-naphthalenyl)amino]carbonyl]-2-thiazolyl]-α-[5-methyl-3-(trifluoromethyl)-1H-pyrazol-1-yl]-β-oxo-1-piperidinepropanoate (Compound 6).

Of note are compounds of Formula 1 where G is the thiazole ring, Q is Q-1 and X is $X^1$ and X is linked to the G thiazole ring at the 2 position of said thiazole ring. Of particular note are embodiments of these compounds within Embodiments 1 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-1 and X is $X^1$ and X is linked to the G oxazole ring at the 2 position of said oxazole ring. Of particular note are embodiments of these compounds within Embodiments 1 through 35, Embodiment 42, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-1 and X is $X^2$ and X is linked to the G thiazole ring at the 2 position of said thiazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-1 and X is $X^2$ and X is linked to the G oxazole ring at the 2 position of said oxazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-2 and X is $X^1$ and X is linked to the G thiazole ring at the 2 position of said thiazole ring. Of particular note are embodiments of these compounds within Embodiments 1 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-2 and X is $X^1$ and X is linked to the G oxazole ring at the 2 position of said oxazole ring. Of particular note are embodiments of these compounds within Embodiments 1 through 35, Embodiment 42, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-2 and X is $X^2$ and X is linked to the G thiazole ring at the 2 position of said thiazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-2 and X is $X^2$ and X is linked to the G oxazole ring at the 2 position of said oxazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-8 and X is $X^1$ and X is linked to the G thiazole ring at the 2 position of said thiazole ring. Of particular note are embodiments of these compounds within Embodiments 1 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-8 and X is $X^1$ and X is linked to the G oxazole ring at the 2 position of said oxazole ring. Of particular note are embodiments of these compounds within Embodiments 1 through 35, Embodiment 42, Embodiments 59 through 82, Embodiment 96, Embodiments A1 through A4, Embodiment A6, Embodiment A8 and Embodiments A10 through A12.

Of note are compounds of Formula 1 where G is the thiazole ring, Q is Q-8 and X is $X^2$ and X is linked to the G thiazole ring at the 2 position of said thiazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where G is the oxazole ring, Q is Q-8 and X is $X^2$ and X is linked to the G oxazole ring at the 2 position of said oxazole ring. Of particular note are embodiments of these compounds within Embodiments 1 through 11, Embodiments 14 through 35, Embodiment 41, Embodiments 59 through 82, Embodiment 96, Embodiments A1 through A4, Embodiment A6, Embodiment A8 and Embodiments A10 through A12.

Of note are compounds of Formula 1 where Z is methylene. Of particular note are embodiments of these compounds within Embodiments 1 through 4 and Embodiments 6 through 103.

Of note are compounds of Formula 1 where Z is C=O. Of particular note are embodiments of these compounds within Embodiments 1 through 4 and Embodiments 7 through 103.

This invention provides a fungicidal composition comprising a compound of Formula 1 (including all geometric and stereoisomers, N-oxides, and salts thereof), and at least one other fungicide. Of note as embodiment of such compositions are compositions comprising a compound corresponding to any of the compound embodiments describe above.

This invention provides a fungicidal composition comprising a fungicidally effective amount of a compound of Formula 1 (including all geometric and stereoisomers, N-oxides, and salts thereof), and at least one additional component selected from the group consisting of surfactants, solid diluents and liquid diluents. Of note as embodiment of such compositions are compositions comprising a compound corresponding to any of the compound embodiments describe above.

This invention provides a method for controlling plant diseases caused by fungal plant pathogens comprising applying to the plant or portion thereof, or to the plant seed or seedling, a fungicidally effective amount of a compound of Formula 1 (including all geometric and stereoisomers, N-oxides, and salts thereof). Of note as embodiment of such methods are methods comprising applying a fungicidally effective amount of a compound corresponding to any of the compound embodiments describe above. Of particular notes are embodiment where the compounds are applied as compositions of this invention.

The compounds of Formula 1 can be prepared by one or more of the following methods and variations as described in Schemes 1-17. The definitions of $R^1$, $R^2$, $R^{18}$, A, $W^1$, $W^2$, X, G, $Q^a$, $Q^b$, z and n in the compounds of Formulae 1-24 below are as defined above in the Summary of the Invention unless otherwise noted. Compounds of Formulae 1a-1g are various subsets of the compounds of Formula 1.

As shown in Scheme 1, compounds of Formula 1a can be prepared by coupling of a compound of Formula 2 wherein Y is a suitable leaving group such as Cl, Br, I or OMs (mesylate, —$O_3SCH_3$), with an amine of Formula 3 in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound 4-(dimethylamino)pyridine. The amines of Formula 3 wherein $Q^a$ is an alkyl group can be prepared by either first heating a primary amine $Q^a$-$NH_2$ with an alkyl formate followed by lithium aluminum hydride reduction or by sodium borohydride reduction of N-alkyl imines prepared by treating $Q^a$(=O) with an alkylamine.

Scheme 1

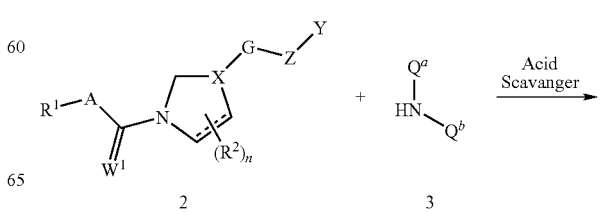

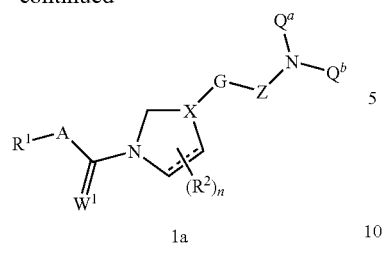

1a

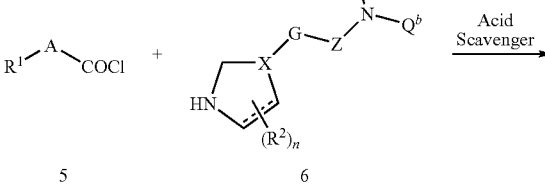

Scheme 3

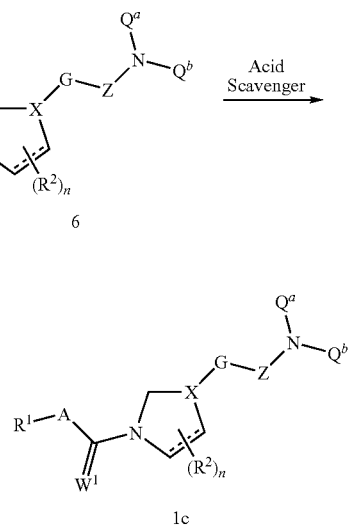

wherein Y is Cl, Br, I or OMs.

An alternate procedure for the preparation of compounds of Formula 1b wherein $W^2$ is O is depicted in Scheme 2 and involves coupling of an acid of Formula 4 with an amine of Formula 3 in the presence of a dehydrative coupling reagent such as dicyclohexylcarbodiimide (DCC), 1-(3-dimethylaminopropyl)-3-ethylcarbodiimide hydrochloride (EDC) or O-benzotriazol-1-yl-N,N,N',N'-tetramethyluronium hexafluorophosphate (HBTU). Polymer-supported reagents are again useful here, such as polymer-bound cyclohexylcarbodiimide. These reactions are typically run at 0-40° C. in a solvent such as dichloromethane or acetonitrile in the presence of a base such as triethylamine or N,N-diisopropylethylamine. In a subsequent step, amides of Formula 1b wherein $W^2$ is O can be converted to thioamides of Formula 1b wherein $W^2$ is S using a variety of standard thiating reagents such as phosphorus pentasulfide or 2,4-bis(4-methoxyphenyl)-1,3-dithia-2,4-diphosphetane-2,4-disulfide (Lawesson's reagent). One skilled in the art will recognize that when $W^1$ is O, the conversion of $W^2$ from O to S may be accompanied by conversion of $W^1$ from O to S. The amines of Formula 3 are known or can be prepared by methods known to one skilled in the art.

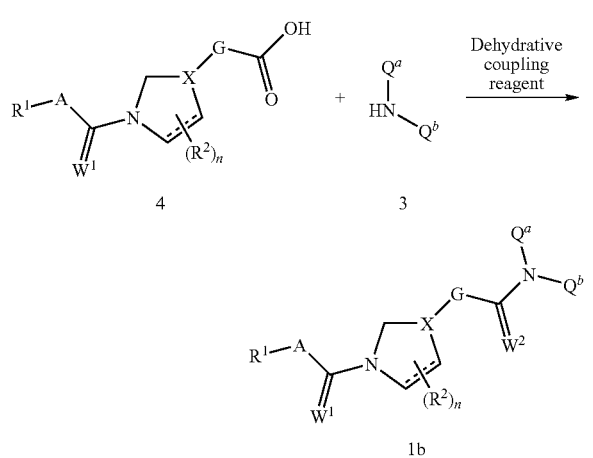

wherein $W^2$ is O

As shown in Scheme 3, compounds of Formula 1c wherein $W^2$ is O can be prepared by coupling a compound of Formula 5 with an amine of Formula 6 in the presence of an acid scavenger, as described for Scheme 1 above. Acid salts of the Formula 6 amines can also be used in this reaction, provided at least 2 equivalents of the acid scavenger is present, as known to one skilled in the art. Typical acids used to form salts with amines include hydrochloric acid, oxalic acid and trifluoroacetic acid.

wherein $W^1$ is O

As shown in Scheme 4, compounds of Formula 1c wherein $W^1$ is O can also be prepared by coupling of a compound of Formula 7 wherein A is other than $NR^{18}$ with an amine of Formula 6 (or its acid salt) in the presence of a dehydrative coupling reagent, analogous to the procedure described in Scheme 2 above. The acids of Formula 7 are known or can be prepared by methods known to one skilled in the art. For example, $R^1CH_2COOH$ where $R^1$ is a heteroaromatic ring linked through nitrogen can be prepared by reacting the corresponding $R^1H$ compound with a haloacetic acid or ester in the presence of base; see, for example, U.S. Pat. No. 4,084,955. $R^1CH_2COOH$ where $R^1$ is a phenyl or a heteroaromatic ring linked through carbon can be prepared from the corresponding $R^1CH_2$-halogen compounds by displacement of the halogen with cyanide followed by hydrolysis; see, for example, K. Adachi, *Yuki Gosei Kagaku Kyokaishi* 1969, 27, 875-876; from $R^1C(\!=\!O)CH_3$ by the Willgerodt-Kindler reaction; see, for example, H. R. Darabi, et. al., *Tetrahedron Letters* 1999, 40, 7549-7552 and M. M. Alam and S. R. Adapa, *Synthetic Communications* 2003, 33, 59-63 and references sited therein; or from $R^1Br$ or $R^1I$ by palladium-catalyzed coupling with t-butyl acetate or diethyl malonate followed by ester hydrolysis; see, for example, W. A. Moradi and S. L. Buchwald, *J. Am. Chem. Soc.* 2001, 123, 7996-8002 and J. F. Hartwig et al., *J. Am. Chem. Soc.* 2002, 124, 12557-12565.

Scheme 4

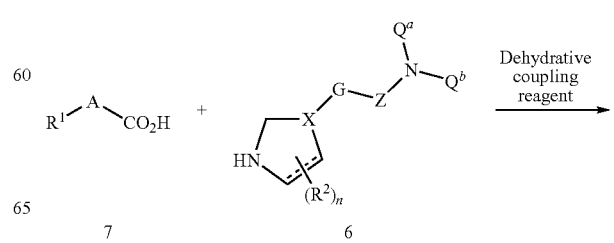

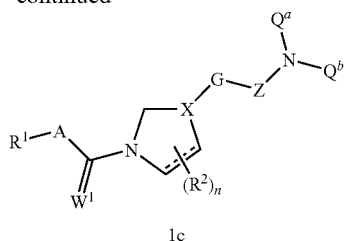

1c wherein A is other than NR$^{18}$, and W$^1$ is O.

The synthetic methods of Schemes 1, 2, 3 and 4 are illustrative of a wide variety of generally useful amide-forming methods known in the art which can be used for preparing compounds of Formula 1. One skilled in the art will recognize that compound of Formula 1 where Q$^a$ is other than H or OH can be prepared from compounds of Formula 1 where Q$^a$ is H by standard alkylation or acylation methods. One skilled in the art will also realize that acid chlorides of Formula 2 wherein Z-Y is C(O)Cl and Formula 5 wherein A is other than NR$^{18}$ can be prepared from acids of Formula 4 and Formula 7, respectively, by numerous well-known methods. Carbamoyl chlorides of Formula 5 wherein A is NR$^{18}$ can be prepared from the corresponding amines R$^1$NHR$^{18}$ by reaction with phosgene.

Certain compounds of Formula 1c wherein W$^1$ is O and R$^1$ is a 5-membered nitrogen-containing heteroaromatic ring linked through the nitrogen atom can be prepared by reaction of the parent heterocycle of Formula 8 and a haloalkylcarbonyl compound of Formula 9 wherein A is other than NR$^{18}$ as shown in Scheme 5. The reaction is carried out in the presence of a base such as sodium hydride or potassium carbonate in a solvent such as tetrahydrofuran, N,N-dimethylformamide or acetonitrile at 0 to 80° C. The haloalkyl-carbonyl compound of Formula 9 can be prepared by the reaction of an amine of Formula 6 with a haloalkylcarbonyl halide or a haloalkylcarboxylic acid or its anhydride, analogous to the amide-forming reactions described in Schemes 3 and 4, respectively.

Scheme 5

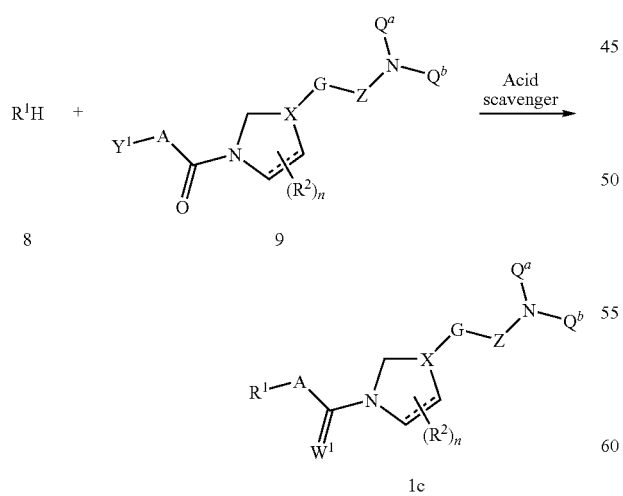

wherein Y$^1$ is Cl, Br or I, A is other than NR$^{18}$, and W$^1$ is O.

Compounds of Formula 1d (Formula 1 wherein A is NH) where R$^1$ is phenyl or a 5- or 6-membered heteroaromatic ring linked via a carbon atom and W$^1$ is O or S, can be prepared by reaction of an amine of Formula 6 with an isocyanate or an isothiocyanate of Formula 10, respectively, as depicted in Scheme 6. This reaction is typically carried out at an ambient temperature in an aprotic solvent such as dichloromethane or acetonitrile.

Scheme 6

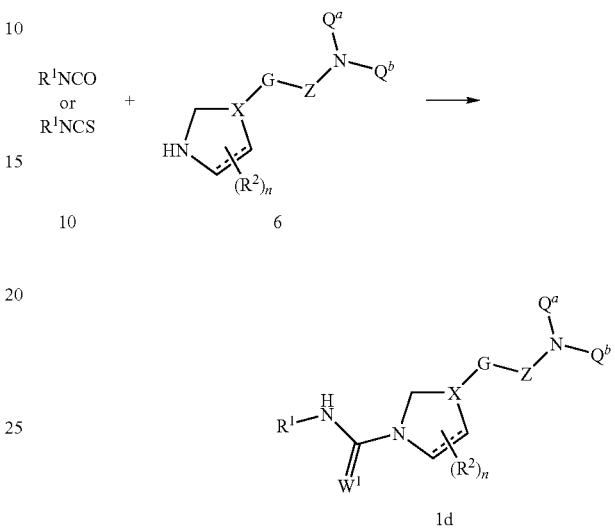

wherein W$^1$ is O or S

Compounds of Formula 1e wherein W$^1$ is O or S can be prepared by the reaction of an amine of Formula 11 with a carbamoyl or thiocarbamoyl chloride or imidazole of Formula 12 as shown in Scheme 7. When Y$^2$ is chlorine, the reaction is typically carried out in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. The carbamoyl or thiocarbamoyl chlorides of Formula 12 (wherein Y$^2$ is Cl) and W$^1$ is O or S can be prepared from amines of Formula 6 by treatment with phosgene or thiophosgene, respectively, or their equivalents, while carbamoyl or thiocarbamoyl imidazoles of Formula 12 (wherein Y$^2$ is imidazol-1-yl) can be prepared from amines of Formula 6 by treatment with 1,1'-carbonyldiimidazole or 1,1'-thiocarbonyl-diimidazole, respectively, according to general methods known to one skilled in the art.

Scheme 7

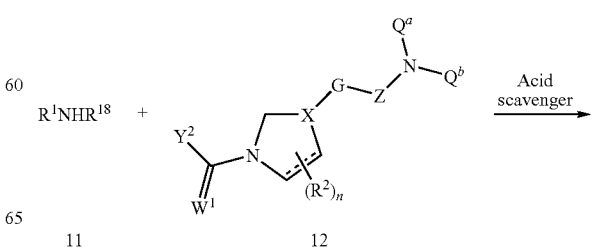

-continued

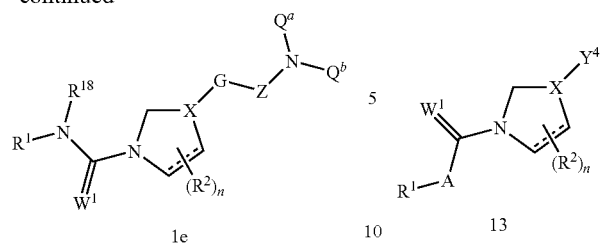

1e wherein $W^1$ is O or S, and $Y^2$ is Cl or imidazol-1-yl.

Certain compounds of Formula 1f (Formula 1 where the ring containing X is saturated) can be prepared from compounds of Formula 1g (Formula 1 where the ring containing X is unsaturated) by catalytic hydrogenation as shown in Scheme 8. Typical conditions involve exposing a compound of Formula 1g to hydrogen gas at a pressure of 70 to 700 kPa, preferably 270 to 350 kPa, in the presence of a metal catalyst such as palladium supported on an inert carrier such as activated carbon, in a weight ratio of 5 to 20% of metal to carrier, suspended in a solvent such as ethanol at ambient temperature. This type of reduction is very well known; see, for example, *Catalytic Hydrogenation*, L. Cerveny, Ed., Elsevier Science, Amsterdam, 1986. One skilled in the art will recognize that other certain functionalities that may be present in compounds of Formula 1g can also be reduced under catalytic hydrogenation conditions, thus requiring a suitable choice of catalyst and conditions.

Scheme 8

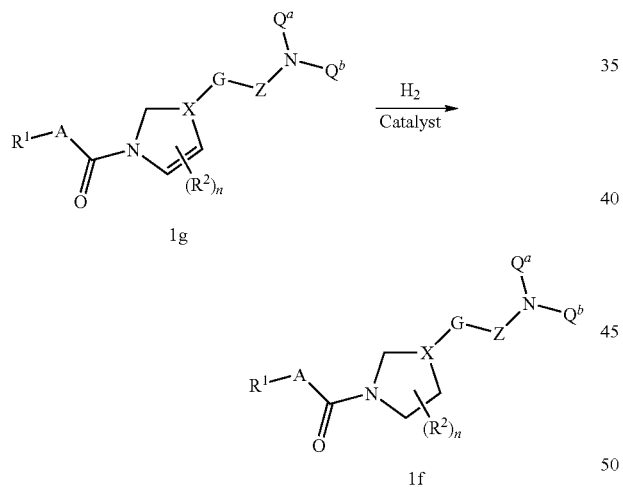

wherein X is $X^1$, $X^2$, $X^5$ or $X^8$.

Certain compounds of Formula 1a wherein X is $X^1$ or $X^5$, and G is linked to the ring containing X via a nitrogen atom, can be prepared by displacement of an appropriate leaving group $Y^4$ on the ring containing the X of Formula 13 with a nitrogen-containing heterocycle of Formula 14 in the presence of a base as depicted in Scheme 9. Suitable bases include sodium hydride or potassium carbonate, and the reaction is carried out in a solvent such as N,N-dimethylformamide or acetonitrile at 0 to 80° C. Suitable leaving groups in the compounds of Formula 13 include bromide, iodine, mesylate (OS(O)$_2$CH$_3$), triflate (OS(O)$_2$CF$_3$) and the like, and compounds of Formula 13 can be prepared from the corresponding compounds wherein $Y^4$ is OH, using general methods known in the art.

Scheme 9

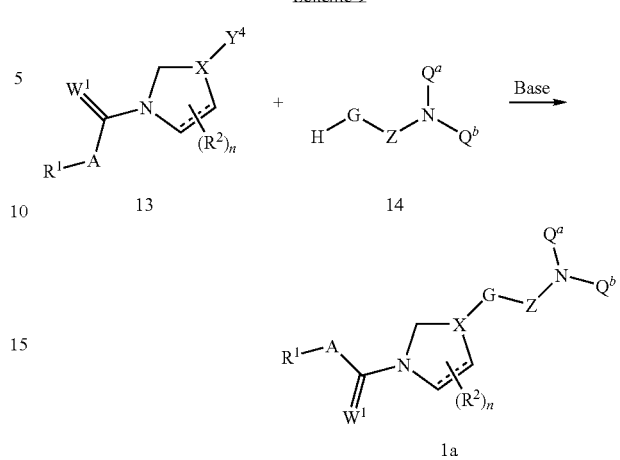

wherein $W^1$ is O or S; X is $X^1$ or $X^5$; and $Y^4$ is a leaving group such as Br, I, OS(O)$_2$Me or OS(O)$_2$CF$_3$.

Compounds of Formula 1a wherein X is $X^2$ or $X^8$ can be prepared by reaction of a compound of Formula 15 with a heterocyclic halide or triflate (OS(O)$_2$CF$_3$) of Formula 16 as shown in Scheme 10. The reaction is carried out in the presence of a base such as potassium carbonate in a solvent such as dimethylsulfoxide, N,N-dimethylformamide or acetonitrile at 0 to 80° C. Compounds of Formula 16 wherein $Y^5$ is triflate can be prepared from corresponding compounds wherein $Y^5$ is OH by methods known to one skilled in the art.

Scheme 10

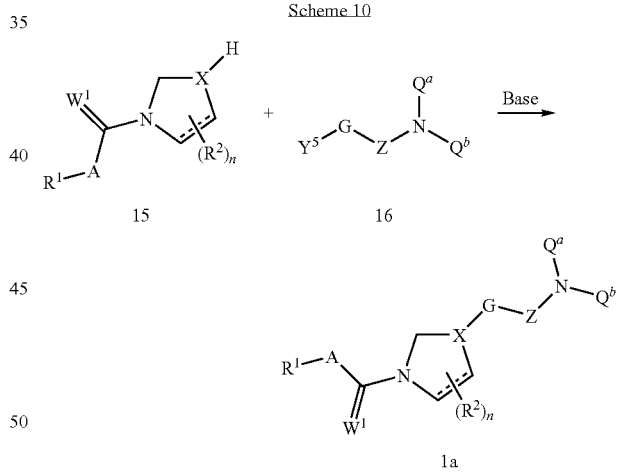

wherein $W^1$ is O or S; X is $X^2$ or $X^8$; and $Y^5$ is a leaving group such as Br, I, OS(O)$_2$Me or OS(O)$_2$CF$_3$.

Amine compounds of Formula 6 can be prepared from the corresponding protected amine compounds of Formula 17 where $Y^6$ is an amine-protecting group as shown in Scheme 11. A wide array of amine-protecting groups are available (see, for example, T. W. Greene and P. G. M. Wuts, *Protective Groups in Organic Synthesis*, 2nd ed.; Wiley: New York, 1991), and the use and choice of the appropriate protecting groups will be apparent to one skilled in chemical synthesis. The protecting group can be removed and the amine isolated as its acid salt or the free amine by general methods known in the art. One skilled in the art will also recognize that the protected amines of Formula 17 can be prepared by methods analogous to those described in Schemes 6 or 7 above where the group $R^1NHC(=W^1)$ or $R^1NR^{18}C(=W^1)$ is replaced by $Y^6$.

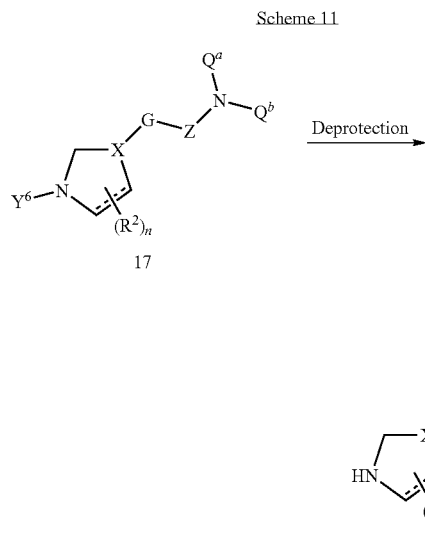

Scheme 11 wherein $Y^6$ is an amine protecting group 6

The compounds of Formula 17 can also be prepared by reaction of a suitably functionalized compound of Formula 18 with a suitably functionalized compound of Formula 19 as shown in Scheme 12. The functional groups $Y^7$ and $Y^8$ are selected from, but not limited to, moieties such as aldehydes, ketones, esters, acids, amides, thioamides, nitriles, amines, alcohols, thiols, hydrazines, oximes, amidines, amide oximes, olefins, acetylenes, halides, alkyl halides, methanesulfonates, trifluoromethanesulfonates, boronic acids, boronates, and the like, which under the appropriate reaction conditions, will allow the construction of the various heterocyclic rings G. As an example, reaction of a compound of Formula 18 where $Y^7$ is a thioamide group with a compound of Formula 19 where $Y^8$ is a bromoacetyl group will give a compound of Formula 17 where G is a thiazole ring. The synthetic literature describes many general methods for forming 5-membered heteroaromatic rings and 5-membered partially saturated heterocyclic rings (e.g., G-1 through G-55); see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. The use of intermediates of Formula 18 where X is $X^1$ and $Y^7$ is Br, I, methanesulfonate or trifluoromethanesulfonate to prepare organozinc reagents for use in cross-coupling reactions with aromatic rings has been described; see, for example, S. Bellotte, *Synlett* 1998, 379-380, and M. Nakamura et al., *Synlett* 2005, 1794-1798. One skilled in the art knows how to select the appropriate functional groups to construct or append the desired heterocyclic rings such as G. Compounds of Formula 18 and 19 are known or can be prepared by a wide variety of general methods known in the art.

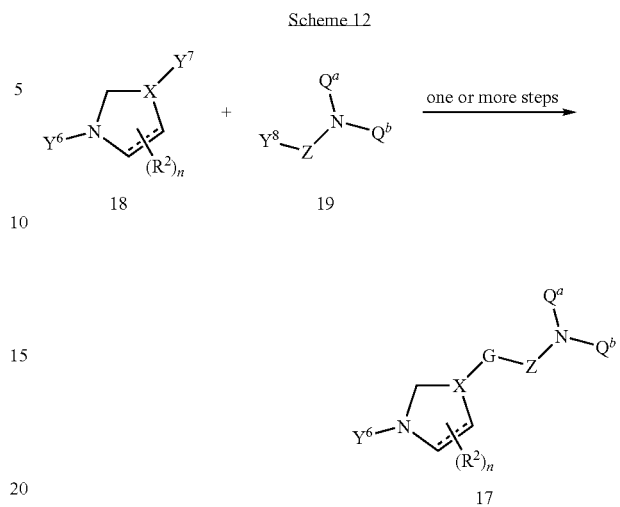

Scheme 12 wherein $Y^6$ is an amine protecting group, and $Y^7$ and $Y^8$ are functional groups suitable for construction of the desired heterocycle G.

The acid compounds of Formula 4 can be prepared by saponification of the corresponding ester compounds of Formula 20 using an alkali metal hydroxide such as LiOH, NaOH or KOH usually in the presence of water along with a co-solvent such as tetrahydrofuran and/or methanol to aid solubility of the ester as illustrated in Scheme 13. The reaction is typically run at 0 to 60° C., and the resulting carboxylate salt is converted to the free acid by addition of a slight excess of a mineral acid such as hydrochloric acid or sulfuric acid.

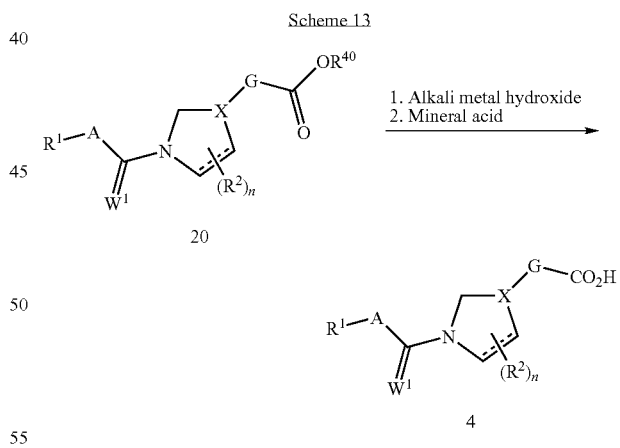

Scheme 13 wherein $R^{40}$ is, for example, $C_1$-$C_4$ alkyl.

As outlined in Scheme 14, the ester compounds of Formula 20 can be prepared from the amine compounds of Formula 21 by methods analogous to those described above for the preparation of compounds of Formula 1. One skilled in the art will recognize that methods analogous to those of Schemes 3, 4, 5, 6, 7 and 8 wherein the group $COOR^{40}$ where $R^{40}$ is, for example, $C_1$-$C_4$ alkyl is substituted for the group $Z$-$NQ^aQ^b$ can be used to provide intermediates of Formula 20 useful for the preparation of compounds of Formula 1.

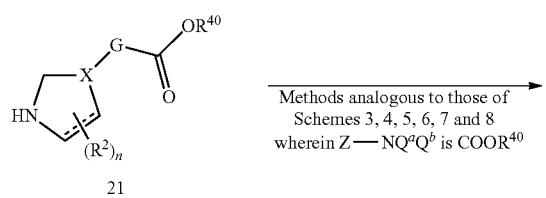

21

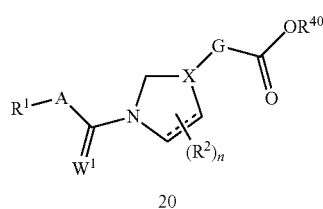

20 wherein $R^{40}$ is, for example, $C_1$-$C_4$ alkyl.

Amine compounds of Formula 21 can be prepared from the protected amine compounds of Formula 22 where PG is an acid-labile amine protecting group such as a t-butoxycarbonyl (t-Boc) or a benzyloxycarbonyl (Cbz) group as shown in Scheme 15. The protecting group is removed by treating with an acid such as trifluoroacetic acid or gaseous HCl in the presence of a solvent such as dichloromethane or dioxane. The amine can be isolated as its acid salt or converted in a subsequent step to the free amine by treatment with a base, as known to one skilled in the art.

Scheme 15

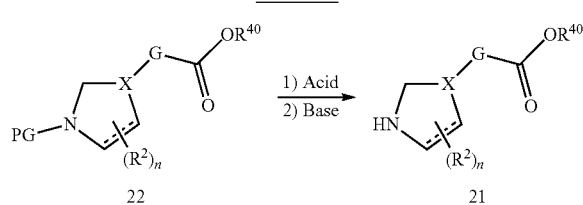

wherein PG is an acid-labile protecting group, and $R^{40}$ is, for example, $C_1$-$C_4$ alkyl.

The amines of Formula 6 can be prepared from the protected amines of Formula 23 where PG is an acid-labile amine protecting group such as a t-butoxycarbonyl (t-Boc) or a benzyloxycarbonyl (Cbz) group as depicted in Scheme 16 by methods analogous to those described above for the preparation of compounds of Formula 21 as outlined in Scheme 15.

Scheme 16

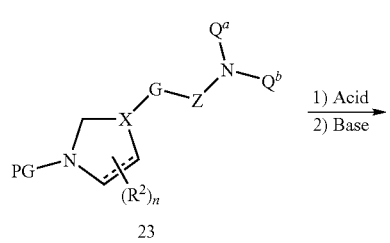

23

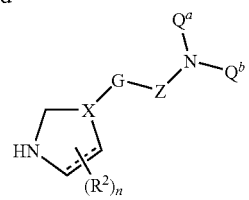

6 wherein PG is an acid-labile protecting group.

The protected amines of Formula 23 can be prepared from compounds of Formula 24 by methods analogous to those described above for the preparation of compounds of Formula 1 as outlined in Scheme 17. One skilled in the art will recognize that in Schemes 1, 2, 8, 9 and 10, the group $R^1AC(=W^1)$ can analogously be replaced by PG where PG is a standard, acid-labile amine protecting group such as a t-butoxycarbonyl (t-Boc) or a benzyloxycarbonyl (Cbz) group to give useful intermediates of Formula 23 for the preparation of compounds of Formula 1. Certain compounds of Formula 24 where $Y^9$ is OH and Z is C=O can be obtained from compounds of Formula 22 by saponification, analogous to methods described for Scheme 13. Certain other compounds of Formula 24 where $Y^9$ is OH and Z is $CH_2$ can be also obtained from compounds of Formula 22 by reduction with $LiBH_4$ or $NaBH_4$ as known to one skilled in the art. Compounds of Formula 24 where $Y^9$ is OH and Z is $CH_2$ can be further transformed to compounds of Formula 24 wherein $Y^9$ is Cl, Br, I, $O(SO_2)Me$ and Z is $CH_2$ by general methods known in the art.

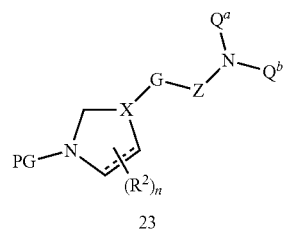

24

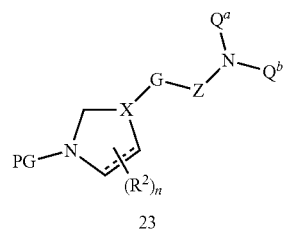

23 wherein $Y^9$ is Cl, Br, I, $O(SO_2)Me$ or OH; PG is an acid-labile protecting group.

Compounds of Formulae 22 and 24 can be prepared by methodologies known in the art of chemical synthesis, including methods analogous to those described with regard to Schemes 1-17. Furthermore, one skilled in the art will recognize that many compounds of Formula 1 can be prepared directly by methods analogous to those described in Scheme 12 above where the group $Y^6$ is replaced by $R^1AC(=W^1)$. Thus, compounds corresponding to Formula 18 in which $Y^6$ is replaced by $R^1AC(=W^1)$ are useful intermediates for the preparation of compounds of Formula 1.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not detailed in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "m" means multiplet, "q" means quartet, "br s" means broad singlet, "br m" means broad multiplet.

Example 1

Preparation of 1-[4-[4-[[methyl[(1R)-1,2,3,4-tetrahydro-1-naphthalenyl]amino]methyl]-2-thiazolyl]-1-piperidinyl]-2-[5-methyl-3-(trifluoromethyl)-1H-pyrazol-1-yl]ethanone (Compound 1)

Step A: Preparation of 1,1-dimethylethyl 4-[4-(ethoxycarbonyl)-2-thiazolyl]-1-piperidinecarboxylate To a suspension of 1,1-dimethylethyl 4-(aminothioxomethyl)-1-tetrahydropyridine-carboxylate (30 g, 123 mmol) in ethanol (180 mL) cooled to 0° C. in an ice bath, was added dropwise a solution of ethyl bromopyruvate (15.7 mL, 125 mmol) in ethanol (180 mL). The ice bath was removed, and the mixture was stirred at ambient temperature overnight. Triethylamine (30 mL) was added, and the mixture was concentrated under reduced pressure, diluted with ethyl acetate, washed with brine, dried over magnesium sulfate and concentrated under reduced pressure to give 31 g of a brown oil, which solidified on standing. A portion of this crude product (8.1 g) was heated with ether (200 mL), and the ether was then decanted. This was repeated a second time, and the combined ether solutions were evaporated under reduced pressure to give 7.6 g of the title compound as a yellow solid.

$^1$H NMR (CDCl$_3$) δ 1.40 (t, 3H), 1.46 (s, 9H), 1.7 (m, 2H), 2.1 (m, 2H), 2.85 (m, 2H), 3.25 (m, 1H), 4.2 (m, 2H), 4.42 (q, 2H), 8.08 (s, 1H).

Step B: Preparation of 1-(1,1-dimethylethyl) 4-[4-(hydroxymethyl)-2-thiazolyl]-1-piperidinecarboxylate A mixture of 1,1-dimethylethyl 4-[4-(ethoxycarbonyl)-2-thiazolyl]-1-piperidinecarboxylate (i.e. the product of Example 1, Step A) (3.4 g, 10 mmol), lithium borohydride (0.33 g, 15 mmol) and methanol (607 μL, 15 mmol) in diethyl ether (40 mL) was heated at reflux for 16 h. The reaction mixture was cooled, treated with water (5 mL) and extracted with diethyl ether and dichloromethane. The combined organic layers were dried (MgSO$_4$) and concentrated under reduced pressure and purified by silica gel chromatography using 50-100% ethyl acetate in hexanes as eluant to give 1.72 g of the title compound as a white solid.

$^1$H NMR (CDCl$_3$) δ 1.45 (s, 9H), 1.66-1.78 (m, 2H), 2.04-2.12 (m, 2H), 2.45-2.53 (m, 1H), 2.80-2.94 (m, 2H), 3.10-3.20 (m, 1H), 4.12-4.30 (m, 2H), 4.75 (d, 2H), 7.073 (s, 1H).

Step C: Preparation of 1-(1,1-dimethylethyl) 4-(4-chloromethyl-2-thiazolyl)-1-piperidinecarboxylate A solution of 1-(1,1-dimethylethyl) 4-(4-hydroxymethyl-2-thiazolyl)-1-piperidinecarboxylate (i.e. the product of Example 1, Step B) (0.83 g, 2.8 mmol) and triethylamine (836 μL, 6.0 mmol) in dichloromethane (3 mL) was cooled to 0° C., and a solution of methanesulfonyl chloride (235 μL, 3.0 mmol) in dichloromethane (2 mL) was added dropwise. The reaction mixture was warmed to ambient temperature, stirred for 2 h, diluted with dichloromethane, washed with 1 N aqueous hydrochloric acid and brine, and dried (MgSO$_4$). The organic layers were concentrated under reduced pressure and purified by silica gel chromatography using 25-50% ethyl acetate in hexanes as eluant to give 0.20 g of the title compound as a white solid.

$^1$H NMR (CDCl$_3$) δ 1.45 (s, 9H), 1.65-1.77 (m, 2H), 2.05-2.12 (m, 2H), 3.12-3.20 (m, 1H), 4.17-4.24 (m, 2H), 4.65 (s, 2H), 7.20 (s, 1H).

Step D: Preparation of 1,1-dimethylethyl 4-[4-[[methyl[(1R)-1,2,3,4-tetrahydro-1-naphthalenyl]amino] methyl]-2-thiazolyl]-1-piperidinecarboxylate A mixture of 1-(1,1-dimethylethyl) 4-(4-chloromethyl-2-thiazolyl)-1-piperidinecarboxylate (i.e. the product of Example 1, Step C) (0.15 g, 0.47 mmol), (1R)-1,2,3,4-tetrahydro-N-methyl-1-naphthalenamine (0.076 g, 0.47 mmol) and potassium carbonate (0.072 g, 0.52 mmol) in dry acetonitrile (5 mL) was heated at reflux for two days. Then the reaction mixture was filtered, concentrated under reduced pressure, diluted with dichloromethane, and washed with 1 N aqueous hydrochloric acid and water. The organic layers were dried (MgSO$_4$) and concentrated under reduced pressure to give 0.19 g of the title compound as a tan foam.

$^1$H NMR (CDCl$_3$) δ 1.47 (s, 9H), 1.58-1.78 (m, 4H), 1.98-2.12 (m, 4H), 2.31 (s, 3H), 2.70-2.90 (m, 4H), 3.10-3.20 (m, 1H), 3.75 (s, 2H), 3.92-4.00 (m, 1H), 4.13-4.24 (br s, 2H), 7.03-7.21 (m, 4H), 7.90 (d, 1H).

Step E: Preparation of 5-methyl-3-(trifluoromethyl)-1H-pyrazol-1-acetic acid

A mixture of 3-methyl-5-trifluoromethylpyrazole (10.0 g, 66.7 mmol), ethyl bromoacetate (11.1 mL, 100 mmol) and potassium carbonate (18.4 g, 133 mmol) in N,N-dimethylformamide (80 mL) was stirred at ambient temperature overnight. The orange mixture was filtered, diluted with ethyl acetate, washed with water and brine, dried (MgSO$_4$) and concentrated under reduced pressure to give 15.7 g of the pyrazole ester. The ester dissolved in tetrahydrofuran (100 mL) was treated with 11 mL of a 50% aqueous NaOH solution in 90 mL of water, and the mixture was stirred at ambient temperature overnight. The tetrahydrofuran solvent was removed from the mixture by evaporation under reduced pressure. The aqueous solution remaining was washed with ether and then acidified with concentrated hydrochloric acid to lower the pH to 1, resulting formation of a precipitate. The precipitate was collected under filtration, washed with water and dried to give 12.1 g of the title compound as a white solid.

$^1$H NMR (Acetone-d$_6$) δ 2.35 (s, 3H), 5.07 (s, 2H), 6.45 (s, 1H).

Step F: Preparation of 5-methyl-3-(trifluoromethyl)-1H-pyrazole-1-acetyl chloride 5-Methyl-3-(trifluoromethyl)-1H-pyrazol-1-yl]acetic acid (7.58 g, 36.4 mmol) (i.e. the product of Example 1, Step E) was dissolved in dichloromethane (100 mL). N,N-dimethylformamide (1 drop) was added to the reaction mixture, which was then cooled to 0° C. Oxalyl chloride (3.5 mL, 40 mmol) was added dropwise to the stirred reaction mixture, which was then allowed to warm to room temperature for 3 h. The resulting mixture was concentrated under reduced pressure and placed under high vacuum to give 7.93 g of the title compound as a tan solid. This compound was of sufficient purity to use in subsequent reactions.

$^1$H NMR (CDCl$_3$) δ 2.31 (s, 3H), 5.27 (s, 2H), 6.38 (s, 1H).

Step G: Preparation of 1-[4-[4-[[methyl[(1R)-1,2,3,4-tetrahydro-1-naphthalenyl]amino]methyl]-2-thiazolyl]-1-piperidinyl]-2-[5-methyl-3-(trifluoromethyl)-1H-pyrazol-1-yl]ethanone A solution of 1,1-dimethylethyl 4-[4-[[methyl[(1R)-1,2,3,4-tetrahydro-1-naphthalenyl]amino]methyl]-2-thiazolyl]-1-piperidinecarboxylate (i.e. the product of Example 1, Step D) (0.19 g, 0.43 mmol) in methanol (5 mL) was treated with a solution of hydrogen chloride in diethyl ether (2 M, 2.15 mL, 4.3 mmol). The reaction mixture was stirred at ambient temperature for 4 h and then concentrated under reduced pressure. The resulting residue and triethylamine (0.28 mL, 2.0 mmol) were dissolved in dichloromethane (10 mL), and the stirred solution was cooled to 0° C. To this solution was added dropwise a solution of 5-methyl-3-(trifluoromethyl)-1H-pyrazole-1-acetyl chloride (i.e. the product of Example 1, Step F) (113 mg, 0.50 mmol) in dichloromethane (2 mL). The stirred reaction mixture was warmed to ambient temperature for 2 h, and then was diluted with dichloromethane. The organic layer was washed with 1 N aqueous hydrochloric acid, saturated aqueous sodium bicarbonate solution and brine, and dried (MgSO$_4$). The organic layers were concentrated under reduced pressure to give 0.16 g of the title product, a compound of the present invention, as an oil.

$^1$H NMR (CDCl$_3$) δ 1.60-1.80 (m, 4H), 2.00-2.10 (m, 2H), 2.12-2.23 (m, 2H), 2.29 (m, 3H), 2.63-2.90 (m, 3H), 3.20-3.34 (m, 2H), 3.75-3.80 (m, 2H), 3.91-4.03 (m, 2H), 4.52-4.61 (d, 1H), 4.92-5.02 (m, 2H), 6.32 (s, 1H), 7.03-7.20 (m, 4H), 7.8 (d, 1H).

Example 2

Preparation of ethyl 4-[4-[[methyl(1,2,3,4-tetrahydro-1-naphthalenyl)amino]carbonyl]-2-thiazolyl]-α-[5-methyl-3-(trifluoromethyl)-1H-pyrazol-1-yl]-β-oxo-1-piperidinepropanoate (Compound 6)

Step A: Preparation of ethyl 2-(4-piperidinyl)-4-thiazolecarboxylate monohydrochloride A solution of 1,1-dimethylethyl 4-[4-(ethoxycarbonyl)-2-thiazolyl]-1-piperidinecarboxylate (11.1 g, 32.7 mmol) (i.e. the product of Example 1, Step A) in diethyl ether (100 mL) at 0° C. was treated with a solution of hydrogen chloride in diethyl ether (2 M, 166 mL, 331 mmol). The reaction mixture then was diluted with absolute ethanol (100 mL) and stirred overnight at room temperature. The reaction mixture was concentrated under reduced pressure, re-dissolved in ethanol and evaporated again to leave a solid. The resulting solid was placed under a high vacuum for several hours to give 10.38 g of the title compound as a hygroscopic white powder. This compound was of sufficient purity to use in subsequent reactions.

$^1$H NMR (DMSO-d$_6$) δ 1.30 (t, 3H), 1.9 (m, 2H), 2.2 (m, 2H), 3.0 (m, 2H), 3.35 (m, 2H), 3.4 (m, 1H), 4.3 (q, 2H), 8.9-9.3 (br m, 2H).

Step B: Preparation of ethyl-2-[1-[[5-methyl-3-(trifluoromethyl)-1H-pyrazol-1-yl]acetyl]-4-piperidinyl]-4-thiazolecarboxylate A solution of ethyl 2-(4-piperidinyl)-4-thiazolecarboxylate monohydrochloride (i.e. the product of Example 2, Step A) (10.38 g, 33.1 mmol) and triethylamine (23 mL, 165 mmol) in dichloromethane (200 mL) was added to a stirred solution of 5-methyl-3-(trifluoromethyl)-1H-pyrazol-1-yl] acetyl chloride (i.e. the product of Example 1, Step F) (7.58 g, 36.4 mmol) in dichloromethane (50 mL) at 0° C. The stirred reaction mixture was allowed to warm to room temperature overnight. Then the reaction mixture was poured into water, and the mixture was extracted with dichloromethane. The organic layer was washed with 1 N hydrochloric acid, water, saturated aqueous sodium bicarbonate solution and brine, dried (MgSO$_4$) and filtered. The filtrate was concentrated under reduced pressure to give 13.0 g of the title compound as an oil. This compound was of sufficient purity to use in subsequent reactions.

$^1$H NMR (CDCl$_3$) δ 1.4 (t, 3H), 1.78 (m, 2H), 2.2 (m, 2H), 2.32 (s, 3H), 2.80 (m, 1H), 3.25 (m, 1H), 3.36 (m, 1H), 4.07 (m, 1H), 4.42 (q, 2H), 4.62 (m, 1H), 4.98 (m, 2H), 6.34 (s, 1H), 8.09 (s, 1H).

Step C: Preparation of 2-[1-[[5-methyl-3-(trifluoromethyl)-1H-pyrazol-1-yl]acetyl]-4-piperidinyl]-4-thiazolecarboxylic acid A stirred solution of ethyl-2-[1-[[5-methyl-3-(trifluoromethyl)-1H-pyrazol-1-yl]acetyl]-4-piperidinyl]-4-thiazolecarboxylate (13.0 g, 30.2 mmol) (i.e. the product of Example 2, Step B) in methanol (60 mL) was cooled to 0° C. and treated with an aqueous sodium hydroxide solution (1 N, 36.3 mL, 36.3 mmol). The stirred reaction mixture was allowed to warm to room temperature for 5 h. The reaction mixture was cooled again to 0° C. and treated with aqueous hydrochloric acid (1 N, 36.3 mL, 36.3 mmol). The resulting precipitate was collected under filtration, washed with water and dried in a vacuum oven at 100° C. to give 10.95 g of the title compound as a white solid.

$^1$H NMR (DMSO-$d_6$) δ 1.55 (m, 1H), 1.80 (m, 1H), 2.1 (m, 2H), 2.21 (s, 3H), 2.82 (m, 1H), 3.30 (m, 2H), 3.98 (m, 1H), 4.38 (m, 1H), 5.28 (m, 2H), 6.50 (s, 1H), 8.36 (s, 1H), 12.9 (br s, 1H).

Step D: Preparation of 2-[1-[[5-methyl-3-(trifluoromethyl)-1H-pyrazol-1-yl]acetyl]-4-piperidinyl]-4-thiazolecarbonyl chloride A stirred solution of 2-[1-[[5-methyl-3-(trifluoromethyl)-1H-pyrazol-1-yl]acetyl]-4-piperidinyl]-4-thiazolecarboxylic acid (2.55 g, 5.87 mmol) (i.e. the product of Example 2, Step C) in dichloromethane (100 mL) was cooled to −10° C., and 1 drop of N,N-dimethyl-formamide was added. A solution of oxalyl chloride (0.60 mL, 6.8 mmol) in dichloromethane (10 mL) was added dropwise to the stirred reaction mixture. The reaction mixture was stirred at −10° C. for 30 minutes more, and then allowed to warm to room temperature and stir an additional 16 h. The resulting homogeneous mixture was evaporated in vacuo, and the residue was placed under high vacuum for several hours to give 2.46 g of the title compound as a light yellow solid. This compound was of sufficient purity to use in subsequent reactions.

$^1$H NMR (CDCl$_3$) δ 1.80 (m, 2H), 2.2 (m, 2H), 2.33 (s, 3H), 2.88 (m, 1H), 3.36 (m, 2H), 4.10 (m, 1H), 4.60 (m, 1H), 4.99 (m, 2H), 6.34 (s, 1H), 8.39 (s, 1H).

Step E: Preparation of N-methyl-2-[1-[[5-methyl-3-(trifluoromethyl)-1H-pyrazol-1-yl]acetyl]-4-piperidinyl]-N-(1,2,3,4-tetrahydro-1-naphthalenyl)-4-thiazolecarboxamide To a stirred solution of 1,2,3,4-tetrahydro-N-methyl-1-naphthalenamine (145 mg, 0.9 mmol) and triethylamine (0.16 mL, 1.13 mmol) in dichloromethane (2 mL) at 0° C. was gradually added 2-[1-[[5-methyl-3-(trifluoromethyl)-1H-pyrazol-1-yl]acetyl]-4-piperidinyl]-4-thiazolecarbonyl chloride (316 mg, 0.75 mmol) (i.e. the product of Example 2, Step D). The reaction mixture was stirred at room temperature for 16 h and then diluted with dichloromethane (4 mL). The mixture was washed with water, 1 N hydrochloric acid, water, saturated aqueous sodium bicarbonate solution and brine, dried (MgSO$_4$) and filtered. The filtrate was concentrated in vacuo to provide crude product, which was purified by medium-pressure liquid chromatography on silica gel using 60-100% of ethyl acetate in hexanes as eluant to give 242 mg of the title compound as white foam.

$^1$H NMR (CDCl$_3$) δ 1.6-2.0 (m, 4H), 2.05-2.3 (m, 6H), 2.7-3.0 (m, 6H), 3.22-3.35 (m, 2H), 3.95-4.58 (m, 3H), 4.96-5.02 (m, 2H), 5.67-6.05 (m, 1H), 6.32 (s, 1H), 7.05-7.25 (m, 4H), 7.85 (m, 1H).

Step F: Preparation of ethyl 4-[4-[[methyl(1,2,3,4-tetrahydro-1-naphthalenyl)amino]carbonyl]-2-thiazolyl]-α-[5-methyl-3-(trifluoromethyl)-1H-pyrazol-1-yl]-β-oxo-1-piperidinepropanoate (Compound 6)

To a stirred solution of N-methyl-2-[1-[[5-methyl-3-(trifluoromethyl)-1H-pyrazol-1-yl]acetyl]-4-piperidinyl]-N-(1,2,3,4-tetrahydro-1-naphthalenyl)-4-thiazolecarboxamide (120 mg, 0.23 mmol) (i.e. the product of Example 2, Step E) in tetrahydrofuran (5 mL) at −78° C. was added a solution of lithium diisopropylamide in tetrahydrofuran (0.5 M, 2.0 mL, 1 mmol). After stirring at −78° C. for 30 minutes, a solution of ethyl chloroformate (100 μL) in tetrahydrofuran (2 mL) was added. The reaction mixture was stirred at −78° C. for 30 minutes more and then at 0° C. for 30 minutes. The reaction mixture was quenched by addition of saturated aqueous ammonium chloride solution, and the mixture was extracted with ethyl acetate. The organic layer was dried (MgSO$_4$) and concentrated under reduced pressure, and the residue was purified by medium-pressure liquid chromatography using 75-100% of ethyl acetate in hexanes as eluant to provide 4 mg of the title product, a compound of the present invention.

Mass spectrum (AP$^+$) 618 (M+1).

By the procedures described herein, together with methods known in the art, the following compounds of Tables 1A to 5 can be prepared. The following abbreviations are used in the Tables which follow: t means tertiary, s means secondary, n means normal, means iso, c means cyclo, Ac means acetyl, Me means methyl, Et means ethyl, Pr means propyl, i-Pr means isopropyl, c-Pr means cyclopropyl, Bu means butyl, Pen means pentyl, Hex means hexyl, CN means cyano, SO$_2$ means S(O)$_2$. A dash (-) indicates no substituents.

The invention includes but is not limited to the following exemplary species.

TABLE 1A

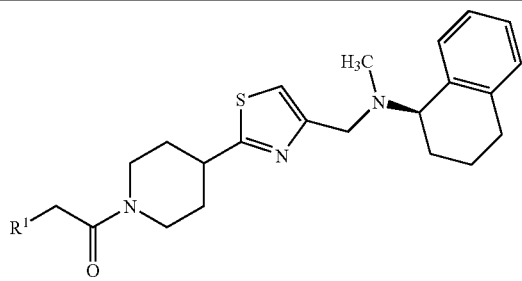

| R$^1$ | R$^1$ |
|---|---|
| phenyl | 2,5-dichlorophenyl |
| 2-methylphenyl | 5-bromo-2-chlorophenyl |
| 2-methoxyphenyl | 2-chloro-5-iodophenyl |
| 2-chlorophenyl | 2-chloro-5-methylphenyl |
| 2-bromophenyl | 2-chloro-5-ethylphenyl |
| 2-ethylphenyl | 2-chloro-5-propylphenyl |
| 2-ethoxyphenyl | 2-chloro-5-isopropylphenyl |

TABLE 1A-continued

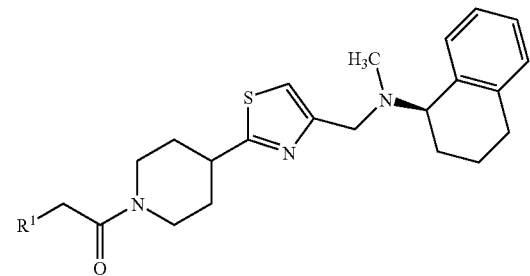

| R$^1$ | R$^1$ |
|---|---|
| 2-(methylthio)phenyl | 2-chloro-5-(trifluoromethyl)phenyl |
| 2-(ethylthio)phenyl | 2-chloro-5-(2,2,2-trifluoroethyl)phenyl |
| 2-(trifluoromethoxy)phenyl | 2-chloro-5-(pentafluoroethyl)phenyl |
| 3-chlorophenyl | 2-chloro-5-cyanophenyl |
| 3-bromophenyl | 2-chloro-5-nitrophenyl |
| 3-iodophenyl | 2-bromo-5-chlorophenyl |
| 3-methylphenyl | 2,5-dibromophenyl |
| 3-ethylphenyl | 2-bromo-5-iodophenyl |
| 3-propylphenyl | 2-bromo-5-methylphenyl |
| 3-isopropylphenyl | 2-bromo-5-ethylphenyl |
| 3-(trifluoromethyl)phenyl | 2-bromo-5-propylphenyl |
| 3-(2,2,2-trifluoroethyl)phenyl | 2-bromo-5-isopropylphenyl |
| 3-(pentafluoroethyl)phenyl | 2-bromo-5-(trifluoromethyl)phenyl |
| 3-cyanophenyl | 2-bromo-5-(2,2,2-trifluoroethyl)phenyl |
| 3-nitrophenyl | 2-bromo-5-(pentafluoroethyl)phenyl |
| 2-bromo-5-cyanophenyl | 2-ethyl-5-(trifluoromethyl)phenyl |
| 2-bromo-5-nitrophenyl | 2-ethyl-5-(2,2,2-trifluoroethyl)phenyl |
| 5-chloro-2-methylphenyl | 2-ethyl-5-(pentafluoroethyl)phenyl |
| 5-bromo-2-methylphenyl | 5-cyano-2-ethylphenyl |
| 5-iodo-2-methylphenyl | 2-ethyl-5-nitrophenyl |
| 2,5-dimethylphenyl | 3-methylpyrazol-1-yl |
| 5-ethyl-2-methylphenyl | 3-chloropyrazol-1-yl |
| 2-methyl-5-propylphenyl | 3-bromopyrazol-1-yl |
| 5-isopropyl-2-methylphenyl | 3-iodopyrazol-1-yl |
| 2-methyl-5-(trifluoromethyl)phenyl | 3-ethylpyrazol-1-yl |
| 2-methyl-5-(2,2,2-trifluoroethyl)phenyl | 3-(trifluoromethyl)pyrazol-1-yl |
| 2-methyl-5-(pentafluoroethyl)phenyl | 3-(2,2,2-trifluoroethyl)pyrazol-1-yl |
| 5-cyano-2-methylphenyl | 3-(pentafluoroethyl)pyrazol-1-yl |
| 2-methyl-5-nitrophenyl | 3-cyanopyrazol-1-yl |
| 5-chloro-2-methoxyphenyl | 3-nitropyrazol-1-yl |
| 5-bromo-2-methoxyphenyl | 3,5-dimethylpyrazol-1-yl |
| 5-iodo-2-methoxyphenyl | 3-chloro-5-methylpyrazol-1-yl |
| 2-methoxy-5-methylphenyl | 3-bromo-5-methylpyrazol-1-yl |
| 5-ethyl-2-methoxyphenyl | 3-iodo-5-methylpyrazol-1-yl |
| 2-methoxy-5-propylphenyl | 3-ethyl-5-methylpyrazol-1-yl |
| 5-isopropyl-2-methoxyphenyl | 5-methyl-3-propylpyrazol-1-yl |
| 2-methoxy-5-(trifluoromethyl)phenyl | 3-isopropyl-5-methylpyrazol-1-yl |
| 2-methoxy-5-(2,2,2-trifluoroethyl)phenyl | 5-methyl-3-(trifluoromethyl)pyrazol-1-yl |
| 2-methoxy-5-(pentafluoroethyl)phenyl | 5-methyl-3-(2,2,2-trifluoroethyl)pyrazol-1-yl |
| 5-cyano-2-methoxyphenyl | 5-methyl-3-(pentafluoroethyl)pyrazol-1-yl |
| 2-methoxy-5-nitrophenyl | 3-cyano-5-methylpyrazol-1-yl |
| 5-chloro-2-ethylphenyl | 5-methyl-3-nitropyrazol-1-yl |
| 5-bromo-2-ethylphenyl | 5-chloro-3-methylpyrazol-1-yl |
| 2-ethyl-5-iodophenyl | 3,5-dichloropyrazol-1-yl |
| 2-ethyl-5-methylphenyl | 5-chloro-3-bromopyrazol-1-yl |
| 2,5-diethylphenyl | 5-chloro-3-iodopyrazol-1-yl |
| 2-ethyl-5-propylphenyl | 5-chloro-3-ethylpyrazol-1-yl |
| 2-ethyl-5-isopropylphenyl | 5-chloro-3-propylpyrazol-1-yl |
| 5-chloro-3-isopropylpyrazol-1-yl | 5-hexyl-2-methylphenyl |
| 5-chloro-3-(trifluoromethyl)pyrazol-1-yl | 5-allyl-2-methylphenyl |
| 5-chloro-3-(2,2,2-trifluoroethyl)pyrazol-1-yl | 2-methyl-5-(4-methyl-3-pentenyl)phenyl |
| 5-chloro-3-(pentafluoroethyl)pyrazol-1-yl | 2-methyl-5-propargylphenyl |
| 5-chloro-3-cyanopyrazol-1-yl | 2-methyl-5-(3-methylpropargyl)phenyl |
| 5-chloro-3-nitropyrazol-1-yl | 5-cyclopropyl-2-methylphenyl |
| 5-bromo-3-methylpyrazol-1-yl | 5-cyclohexyl-2-methylphenyl |
| 5-bromo-3-chloropyrazol-1-yl | 2-methyl-5-(pentafluoroisopropyl)phenyl |
| 3,5-dibromopyrazol-1-yl | 5-(3,3-dichloro-2-propen-1-yl)-2-methylphenyl |
| 5-bromo-3-iodopyrazol-1-yl | 2-methyl-5-(4,4,4-trifluoro-2-butyn-1-yl)phenyl |
| 5-bromo-3-ethylpyrazol-1-yl | 5-(2,2-dichlorocyclopropan-1-yl)-2-methylphenyl |
| 5-bromo-3-propylpyrazol-1-yl | 2-methyl-5-(trifluoromethoxy)phenyl |
| 5-bromo-3-isopropylpyrazol-1-yl | 2-chloro-5-(isobutylthio)phenyl |
| 5-bromo-3-(trifluoromethyl)pyrazol-1-yl | 2-chloro-5-(ethylsulfonyl)phenyl |
| 5-bromo-3-(2,2,2-trifluoroethyl)pyrazol-1-yl | 2-chloro-5-(trifluoromethylthio)phenyl |
| 5-bromo-3-(pentafluoroethyl)pyrazol-1-yl | 2-chloro-5-(trifluoromethylsulfonyl)phenyl |

TABLE 1A-continued

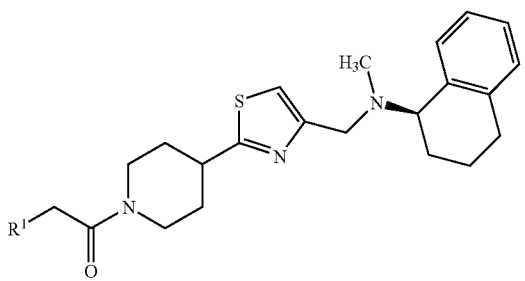

| R¹ | R¹ |
|---|---|
| 5-bromo-3-cyanopyrazol-1-yl | 2-chloro-5-(methylamino)phenyl |
| 5-bromo-3-nitropyrazol-1-yl | 2-chloro-5-(tert-butylamino)phenyl |
| 5-methoxy-3-methylpyrazol-1-yl | 2-chloro-5-(dimethylamino)phenyl |
| 3-chloro-5-methoxypyrazol-1-yl | 2-chloro-5-(diethylamino)phenyl |
| 5-ethyl-3-methylpyrazol-1-yl | 2-chloro-5-(cyclopropylamino)phenyl |
| 3-chloro-5-ethylpyrazol-1-yl | 3-(methoxymethyl)phenyl |
| 3-bromo-5-ethylpyrazol-1-yl | 2-chloro-5-(ethoxymethyl)phenyl |
| 5-ethyl-3-iodopyrazol-1-yl | 2-chloro-5-(hyroxymethyl)phenyl |
| 3,5-diethylpyrazol-1-yl | 2-chloro-5-(methoxycarbonyl)phenyl |
| 5-ethyl-3-propylpyrazol-1-yl | 2-chloro-5-(ethylcarbonyl)phenyl |
| 5-ethyl-3-isopropylpyrazol-1-yl | 2-chloro-5-(methylcarbonyloxy)phenyl |
| 5-ethyl-3-(trifluoromethyl)pyrazol-1-yl | 2-chloro-5-(metylaminocarbonyl)phenyl |
| 5-ethyl-3-(2,2,2-trifluoroethyl)pyrazol-1-yl | 2-chloro-5-(dimethylaminocarbonyl)phenyl |
| 5-ethyl-3-(pentafluoroethyl)pyrazol-1-yl | 2-methyl-5-(trimethylsilyl)phenyl |
| 3-cyano-5-ethylpyrazol-1-yl | 3,5-dimethyl-2-thienyl |
| 5-ethyl-3-nitropyrazol-1-yl | 3,5-dichloro-2-thienyl |
| 5-butyl-2-methylphenyl | 3,5-dimethyl-2-furyl |
| 1-methyl-2-pyrrolyl | 1-methyl-4-imidazolyl |
| 4-methyl-2-trifluoromethyl-5-thiazolyl | 5-trifluoromethyl-3-(1,2,4-oxadiazolyl) |
| 4-trifluoromethyl-2-thiazolyl | 5-trifluoromethyl-3-(1,2,4-thiadiazolyl) |
| 4-trifluoromethyl-2-oxazolyl | 2-bromo-1-(1,3,4-triazolyl) |
| 4-methyl-2-trifluoromethyl-5-oxazolyl | 5-trifluoromethyl-3-(1,2,4-triazolyl) |
| 4-bromo-5-isothiazolyl | 2-bromo-1-imidazolyl |
| 4-bromo-5-isoxazolyl | 3,6-dimethyl-2-pyridyl |
| 1-methyl-5-pyrazolyl | 2,5-dimethyl-3-pyridyl |
| 1-methyl-5-imidazolyl | 2,5-dimethyl-4-pyridyl |
| 1-methyl-4-trifluoromethyl-2-imidazolyl | 3,6-dichloro-2-pyridyl |
| 4-methyl-3-(1,3,4-triazolyl) | 2,5-dichloro-3-pyridyl |
| 2-methyl-3-(1,2,4-triazolyl) | 2,5-dichloro-4-pyridyl |
| 5-trifluoromethyl-2-(1,3,4-thiadiazolyl) | 4-bromo-3-pyridazinyl |
| 5-trifluoromethyl-2-(1,3,4-oxadiazolyl) | 4-trifluoromethyl-2-pyrimidinyl |
| 3-trifluoromethyl-5-(1,2,4-thiadiazolyl) | 3,6-dimethyl-2-pyrazinyl |
| 3-trifluoromethyl-5-(1,2,4-oxadiazolyl) | 2,5-dimethyl-4-pyrimidinyl |
| 3-trifluoromethyl-1-(1,2,4-triazolyl) | 4-methoxy-5-pyrimidinyl |
| 2,5-dimethyl-1-pyrrolyl | 3,6-dimethyl-4-pyridazinyl |
| 2,5-dimethyl-3-furyl | 5-trifluoromethyl-3-(1,2,4-triazinyl) |
| 2,5-dimethyl-3-thienyl | 5-methoxy-6-(1,2,4-triazinly) |
| 2,5-dichloro-3-thienyl | 4-trifluoromethyl-2-(1,3,5-triazinyl) |
| 1,4-dimethyl-3-pyrrolyl | 3,6-dimethyl-5-(1,2,4-triazinyl) |
| 1,4-dimethyl-3-pyrazolyl | 3,5-bis-(trifluoromethyl)pyrazol-1-yl |
| 1,3-dimethyl-4-pyrazolyl | 1-methyl-3-(trifluoromethyl)pyrazol-5-yl |
| 2,5-dimethyl-4-oxazolyl | 1-methyl-4-(trifluoromethyl)imidazol-2-yl |
| 2,5-dimethyl-4-thiazolyl | 3-methyl-5-(trifluoromethyl)pyrazol-1-yl |
| 3-bromo-4-isothiazolyl | 3-chloro-5-(trifluoromethyl)pyrazol-1-yl |
| 3-bromo-4-isooxazolyl | 3-bromo-5-(trifluoromethyl)pyrazol-1-yl |

TABLE 1B

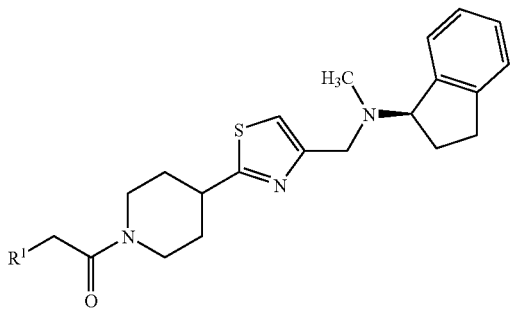

| R¹ | R¹ |
|---|---|
| 2-methoxyphenyl | 2-bromo-5-(trifluoromethyl)phenyl |
| 3-bromophenyl | 2-bromo-5-(2,2,2-trifluoroethyl)phenyl |
| 3-iodophenyl | 2-bromo-5-(pentafluoroethyl)phenyl |
| 3-(trifluoromethyl)phenyl | 2-bromo-5-cyanophenyl |
| 3-(2,2,2-trifluoroethyl)phenyl | 2-bromo-5-nitrophenyl |
| 3-(pentafluoroethyl)phenyl | 5-chloro-2-methylphenyl |
| 3-cyanophenyl | 5-bromo-2-methylphenyl |
| 3-nitrophenyl | 5-iodo-2-methylphenyl |
| 2,5-dichlorophenyl | 2,5-dimethylphenyl |
| 5-bromo-2-chlorophenyl | 5-ethyl-2-methylphenyl |
| 2-chloro-5-iodophenyl | 2-methyl-5-propylphenyl |
| 2-chloro-5-methylphenyl | 5-isopropyl-2-methylphenyl |
| 2-chloro-5-ethylphenyl | 2-methyl-5-(trifluoromethyl)phenyl |
| 2-chloro-5-(trifluoromethyl)phenyl | 2-methyl-5-(2,2,2-trifluoroethyl)phenyl |
| 2-chloro-5-(2,2,2-trifluoroethyl)phenyl | 2-methyl-5-(pentafluoroethyl)phenyl |
| 2-chloro-5-(pentafluoroethyl)phenyl | 5-cyano-2-methylphenyl |
| 2-chloro-5-cyanophenyl | 2-methyl-5-nitrophenyl |
| 2-chloro-5-nitrophenyl | 5-chloro-2-methoxyphenyl |
| 2-bromo-5-chlorophenyl | 5-bromo-2-methoxyphenyl |
| 2,5-dibromophenyl | 5-iodo-2-methoxyphenyl |
| 2-bromo-5-iodophenyl | 2-methoxy-5-methylphenyl |
| 2-bromo-5-methylphenyl | 5-ethyl-2-methoxyphenyl |
| 2-bromo-5-ethylphenyl | 2-methoxy-5-propylphenyl |
| 2-bromo-5-propylphenyl | 2-methoxy-5-(trifluoromethyl)phenyl |
| 2-methoxy-5-(2,2,2-trifluoroethyl)phenyl | 5-chloro-3-methylpyrazol-1-yl |
| 2-methoxy-5-(pentafluoroethyl)phenyl | 3,5-dichloropyrazol-1-yl |
| 5-cyano-2-methoxyphenyl | 5-chloro-3-bromopyrazol-1-yl |
| 2-methoxy-5-nitrophenyl | 5-chloro-3-iodopyrazol-1-yl |
| 5-chloro-2-ethylphenyl | 5-chloro-3-ethylpyrazol-1-yl |
| 5-bromo-2-ethylphenyl | 5-chloro-3-propylpyrazol-1-yl |
| 2-ethyl-5-iodophenyl | 5-chloro-3-(trifluoromethyl)pyrazol-1-yl |
| 2-ethyl-5-methylphenyl | 5-chloro-3-(2,2,2-trifluoroethyl)pyrazol-1-yl |
| 2,5-diethylphenyl | 5-chloro-3-(pentafluoroethyl)pyrazol-1-yl |
| 2-ethyl-5-propylphenyl | 5-chloro-3-cyanopyrazol-1-yl |
| 2-ethyl-5-((trifluoromethyl))phenyl | 5-chloro-3-nitropyrazol-1-yl |
| 2-ethyl-5-(2,2,2-trifluoroethyl)phenyl | 5-bromo-3-methylpyrazol-1-yl |
| 2-ethyl-5-(pentafluoroethyl)phenyl | 5-bromo-3-chloropyrazol-1-yl |
| 5-cyano-2-ethylphenyl | 3,5-dibromopyrazol-1-yl |
| 2-ethyl-5-nitrophenyl | 5-bromo-3-iodopyrazol-1-yl |
| 3-chloropyrazol-1-yl | 5-bromo-3-ethylpyrazol-1-yl |
| 3-bromopyrazol-1-yl | 5-bromo-3-propylpyrazol-1-yl |
| 3-(trifluoromethyl)pyrazol-1-yl | 5-bromo-3-(trifluoromethyl)pyrazol-1-yl |
| 3-(2,2,2-trifluoroethyl)pyrazol-1-yl | 5-bromo-3-(2,2,2-trifluoroethyl)pyrazol-1-yl |
| 3-(pentafluoroethyl)pyrazol-1-yl | 5-bromo-3-(pentafluoroethyl)pyrazol-1-yl |
| 3-cyanopyrazol-1-yl | 5-ethyl-3-methylpyrazol-1-yl |
| 3-nitropyrazol-1-yl | 3-chloro-5-ethylpyrazol-1-yl |
| 3,5-dimethylpyrazol-1-yl | 3-bromo-5-ethylpyrazol-1-yl |
| 3-chloro-5-methylpyrazol-1-yl | 5-ethyl-3-iodopyrazol-1-yl |
| 3-bromo-5-methylpyrazol-1-yl | 3,5-diethylpyrazol-1-yl |
| 3-iodo-5-methylpyrazol-1-yl | 5-ethyl-3-propylpyrazol-1-yl |
| 3-ethyl-5-methylpyrazol-1-yl | 5-ethyl-3-(trifluoromethyl)pyrazol-1-yl |
| 5-methyl-3-propylpyrazol-1-yl | 5-ethyl-3-(2,2,2-trifluoroethyl)pyrazol-1-yl |
| 5-methyl-3-(trifluoromethyl)pyrazol-1-yl | 5-ethyl-3-(pentafluoroethyl)pyrazol-1-yl |
| 5-methyl-3-(2,2,2-trifluoroethyl)pyrazol-1-yl | 3,5-dimethyl-2-thienyl |
| 5-methyl-3-(pentafluoroethyl)pyrazol-1-yl | 3,5-dichloro-2-thienyl |
| 3-cyano-5-methylpyrazol-1-yl | 2,5-dimethyl-3-thienyl |
| 5-methyl-3-nitropyrazol-1-yl | 2,5-dichloro-3-thienyl |
| 3,6-dimethyl-2-pyridyl | 3,5-bis-(trifluoromethyl)pyrazol-1-yl |

TABLE 1B-continued

[Structure: piperidine-thiazole with CH2-N(CH3)-indanyl group, R1-C(=O)- on piperidine N]

| R¹ | R¹ |
|---|---|
| 2,5-dimethyl-3-pyridyl | 1-methyl-3-(trifluoromethyl)pyrazol-5-yl |
| 2,5-dimethyl-4-pyridyl | 1-methyl-4-(trifluoromethyl)imidazol-2-yl |
| 3,6-dichloro-2-pyridyl | 3-methyl-5-(trifluoromethyl)pyrazol-1-yl |
| 2,5-dichloro-3-pyridyl | 3-chloro-5-(trifluoromethyl)pyrazol-1-yl |
| 2,5-dichloro-4-pyridyl | 3-bromo-5-(trifluoromethyl)pyrazol-1-yl |

TABLE 1C

[Structure: piperidine-thiazole with CH2-N(CH3)-CH(R5)-phenyl group, R1-C(=O)- on piperidine N]

| R¹ | R⁵ |
|---|---|
| 2-methoxyphenyl | Et |
| 3-bromophenyl | Et |
| 3-iodophenyl | Et |
| 3-(trifluoromethyl)phenyl | Et |
| 3-(2,2,2-trifluoroethyl)phenyl | Et |
| 3-(pentafluoroethyl)phenyl | Et |
| 3-cyanophenyl | Et |
| 3-nitrophenyl | Et |
| 2,5-dichlorophenyl | Et |
| 5-bromo-2-chlorophenyl | Et |
| 2-chloro-5-iodophenyl | Et |
| 2-chloro-5-methylphenyl | Et |
| 2-chloro-5-ethylphenyl | Et |
| 2-chloro-5-(trifluoromethyl)phenyl | Et |
| 2-chloro-5-(2,2,2-trifluoroethyl)phenyl | Et |
| 2-chloro-5-(pentafluoroethyl)phenyl | Et |
| 2-chloro-5-cyanophenyl | Et |
| 2-chloro-5-nitrophenyl | Et |
| 2-bromo-5-chlorophenyl | Et |
| 2,5-dibromophenyl | Et |
| 2-bromo-5-iodophenyl | Et |
| 2-bromo-5-methylphenyl | Et |
| 2-bromo-5-ethylphenyl | Et |
| 2-bromo-5-propylphenyl | Et |
| 2-bromo-5-(trifluoromethyl)phenyl | Et |
| 2-bromo-5-(2,2,2-trifluoroethyl)phenyl | Et |
| 2-bromo-5-(pentafluoroethyl)phenyl | Et |
| 2-bromo-5-cyanophenyl | Et |
| 2-bromo-5-nitrophenyl | Et |
| 5-chloro-2-methylphenyl | Et |
| 5-bromo-2-methylphenyl | Et |
| 5-iodo-2-methylphenyl | Et |
| 2,5-dimethylphenyl | Et |
| 5-ethyl-2-methylphenyl | Et |
| 2-methyl-5-propylphenyl | Et |
| 5-isopropyl-2-methylphenyl | Et |

TABLE 1C-continued

| R¹ | R⁵ |
|---|---|
| 2-methyl-5-(trifluoromethyl)phenyl | Et |
| 2-methyl-5-(2,2,2-trifluoroethyl)phenyl | Et |
| 2-methyl-5-(pentafluoroethyl)phenyl | Et |
| 5-cyano-2-methylphenyl | Et |
| 2-methyl-5-nitrophenyl | Et |
| 5-chloro-2-methoxyphenyl | Et |
| 5-bromo-2-methoxyphenyl | Et |
| 5-iodo-2-methoxyphenyl | Et |
| 2-methoxy-5-methylphenyl | Et |
| 5-ethyl-2-methoxyphenyl | Et |
| 2-methoxy-5-propylphenyl | Et |
| 2-methoxy-5-(trifluoromethyl)phenyl | Et |
| 2-methoxy-5-(2,2,2-trifluoroethyl)phenyl | Et |
| 2-methoxy-5-(pentafluoroethyl)phenyl | Et |
| 5-cyano-2-methoxyphenyl | Et |
| 2-methoxy-5-nitrophenyl | Et |
| 5-chloro-2-ethylphenyl | Et |
| 5-bromo-2-ethylphenyl | Et |
| 2-ethyl-5-iodophenyl | Et |
| 2-ethyl-5-methylphenyl | Et |
| 2,5-diethylphenyl | Et |
| 2-ethyl-5-propylphenyl | Et |
| 2-ethyl-5-(trifluoromethyl)phenyl | Et |
| 2-ethyl-5-(2,2,2-trifluoroethyl)phenyl | Et |
| 2-ethyl-5-(pentafluoroethyl)phenyl | Et |
| 5-cyano-2-ethylphenyl | Et |
| 2-ethyl-5-nitrophenyl | Et |
| 3-chloropyrazol-1-yl | Et |
| 3-bromopyrazol-1-yl | Et |
| 3-(trifluoromethyl)pyrazol-1-yl | Et |
| 3-(2,2,2-trifluoroethyl)pyrazol-1-yl | Et |
| 3-(pentafluoroethyl)pyrazol-1-yl | Et |
| 3-cyanopyrazol-1-yl | Et |
| 3-nitropyrazol-1-yl | Et |
| 3,5-dimethylpyrazol-1-yl | Et |
| 3-chloro-5-methylpyrazol-1-yl | Et |

TABLE 1C-continued

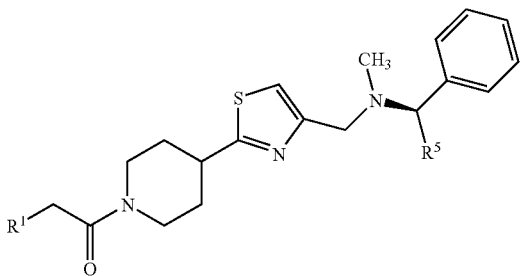

| R¹ | R⁵ |
|---|---|
| 3-bromo-5-methylpyrazol-1-yl | Et |
| 3-iodo-5-methylpyrazol-1-yl | Et |
| 3-ethyl-5-methylpyrazol-1-yl | Et |
| 5-methyl-3-propylpyrazol-1-yl | Et |
| 5-methyl-3-(trifluoromethyl)pyrazol-1-yl | Et |
| 5-methyl-3-(2,2,2-trifluoroethyl)pyrazol-1-yl | Et |
| 5-methyl-3-(pentafluoroethyl)pyrazol-1-yl | Et |
| 3-cyano-5-methylpyrazol-1-yl | Et |
| 5-methyl-3-nitropyrazol-1-yl | Et |
| 5-chloro-3-methylpyrazol-1-yl | Et |
| 3,5-dichloropyrazol-1-yl | Et |
| 5-chloro-3-bromopyrazol-1-yl | Et |
| 5-chloro-3-iodopyrazol-1-yl | Et |
| 5-chloro-3-ethylpyrazol-1-yl | Et |
| 5-chloro-3-propylpyrazol-1-yl | Et |
| 5-chloro-3-(trifluoromethyl)pyrazol-1-yl | Et |
| 5-chloro-3-(2,2,2-trifluoroethyl)pyrazol-1-yl | Et |
| 5-chloro-3-(pentafluoroethyl)pyrazol-1-yl | Et |
| 5-chloro-3-cyanopyrazol-1-yl | Et |
| 5-chloro-3-nitropyrazol-1-yl | Et |
| 5-bromo-3-methylpyrazol-1-yl | Et |
| 5-bromo-3-chloropyrazol-1-yl | Et |
| 3,5-dibromopyrazol-1-yl | Et |
| 5-bromo-3-iodopyrazol-1-yl | Et |
| 5-bromo-3-ethylpyrazol-1-yl | Et |
| 5-bromo-3-propylpyrazol-1-yl | Et |
| 5-bromo-3-(trifluoromethyl)pyrazol-1-yl | Et |
| 5-bromo-3-(2,2,2-trifluoroethyl)pyrazol-1-yl | Et |
| 5-bromo-3-(pentafluoroethyl)pyrazol-1-yl | Et |
| 5-ethyl-3-methylpyrazol-1-yl | Et |
| 3-chloro-5-ethylpyrazol-1-yl | Et |
| 3-bromo-5-ethylpyrazol-1-yl | Et |
| 5-ethyl-3-iodopyrazol-1-yl | Et |
| 3,5-diethylpyrazol-1-yl | Et |
| 5-ethyl-3-propylpyrazol-1-yl | Et |
| 5-ethyl-3-(trifluoromethyl)pyrazol-1-yl | Et |
| 5-ethyl-3-(2,2,2-trifluoroethyl)pyrazol-1-yl | Et |
| 5-ethyl-3-(pentafluoroethyl)pyrazol-1-yl | Et |
| 3,5-dimethyl-2-thienyl | Et |
| 3,5-dichloro-2-thienyl | Et |
| 2,5-dimethyl-3-thienyl | Et |
| 2,5-dichloro-3-thienyl | Et |
| 3,6-dimethyl-2-pyridyl | Et |
| 2,5-dimethyl-3-pyridyl | Et |
| 2,5-dimethyl-4-pyridyl | Et |
| 3,6-dichloro-2-pyridyl | Et |
| 2,5-dichloro-3-pyridyl | Et |
| 2,5-dichloro-4-pyridyl | Et |
| 2-methoxyphenyl | Me |
| 2,5-dichlorophenyl | Me |
| 5-bromo-2-chlorophenyl | Me |
| 2-chloro-5-methylphenyl | Me |
| 2-chloro-5-(trifluoromethyl)phenyl | Me |
| 2,5-dibromophenyl | Me |
| 2-bromo-5-methylphenyl | Me |
| 2-bromo-5-(trifluoromethyl)phenyl | Me |
| 5-chloro-2-methylphenyl | Me |
| 5-bromo-2-methylphenyl | Me |
| 2,5-dimethylphenyl | Me |
| 5-ethyl-2-methylphenyl | Me |
| 2-methyl-5-(trifluoromethyl)phenyl | Me |
| 5-bromo-2-methoxyphenyl | Me |
| 2-methoxy-5-methylphenyl | Me |
| 2-methoxy-5-(trifluoromethyl)phenyl | Me |

TABLE 1C-continued

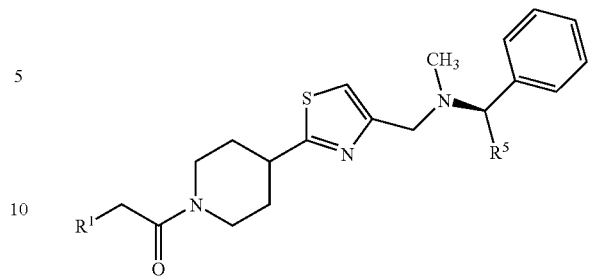

| R¹ | R⁵ |
|---|---|
| 3-(trifluoromethyl)pyrazol-1-yl | Me |
| 3,5-dimethylpyrazol-1-yl | Me |
| 3-ethyl-5-methylpyrazol-1-yl | Me |
| 5-methyl-3-(trifluoromethyl)pyrazol-1-yl | Me |
| 3,5-dichloropyrazol-1-yl | Me |
| 5-chloro-3-(trifluoromethyl)pyrazol-1-yl | Me |
| 3,5-dibromopyrazol-1-yl | Me |
| 5-bromo-3-(trifluoromethyl)pyrazol-1-yl | Me |
| 3,5-diethylpyrazol-1-yl | Me |
| 5-ethyl-3-(trifluoromethyl)pyrazol-1-yl | Me |
| 2-methoxyphenyl | n-Pr |
| 2,5-dichlorophenyl | n-Pr |
| 5-bromo-2-chlorophenyl | n-Pr |
| 2-chloro-5-methylphenyl | n-Pr |
| 2-chloro-5-(trifluoromethyl)phenyl | n-Pr |
| 2,5-dibromophenyl | n-Pr |
| 2-bromo-5-methylphenyl | n-Pr |
| 2-bromo-5-(trifluoromethyl)phenyl | n-Pr |
| 5-chloro-2-methylphenyl | n-Pr |
| 5-bromo-2-methylphenyl | n-Pr |
| 2,5-dimethylphenyl | n-Pr |
| 5-ethyl-2-methylphenyl | n-Pr |
| 2-methyl-5-(trifluoromethyl)phenyl | n-Pr |
| 5-bromo-2-methoxyphenyl | n-Pr |
| 2-methoxy-5-methylphenyl | n-Pr |
| 2-methoxy-5-(trifluoromethyl)phenyl | n-Pr |
| 3-(trifluoromethyl)pyrazol-1-yl | n-Pr |
| 3,5-dimethylpyrazol-1-yl | n-Pr |
| 3-ethyl-5-methylpyrazol-1-yl | n-Pr |
| 5-methyl-3-(trifluoromethyl)pyrazol-1-yl | n-Pr |
| 3,5-dichloropyrazol-1-yl | n-Pr |
| 5-chloro-3-(trifluoromethyl)pyrazol-1-yl | n-Pr |
| 3,5-dibromopyrazol-1-yl | n-Pr |
| 5-bromo-3-(trifluoromethyl)pyrazol-1-yl | n-Pr |
| 3,5-diethylpyrazol-1-yl | n-Pr |
| 5-ethyl-3-(trifluoromethyl)pyrazol-1-yl | n-Pr |
| 2-methoxyphenyl | CN |
| 2,5-dichlorophenyl | CN |
| 5-bromo-2-chlorophenyl | CN |
| 2-chloro-5-methylphenyl | CN |
| 2-chloro-5-(trifluoromethyl)phenyl | CN |
| 2,5-dibromophenyl | CN |
| 2-bromo-5-methylphenyl | CN |
| 2-bromo-5-(trifluoromethyl)phenyl | CN |
| 5-chloro-2-methylphenyl | CN |
| 5-bromo-2-methylphenyl | CN |
| 2,5-dimethylphenyl | CN |
| 5-ethyl-2-methylphenyl | CN |
| 2-methyl-5-(trifluoromethyl)phenyl | CN |
| 5-bromo-2-methoxyphenyl | CN |
| 2-methoxy-5-methylphenyl | CN |
| 2-methoxy-5-(trifluoromethyl)phenyl | CN |
| 3-(trifluoromethyl)pyrazol-1-yl | CN |
| 3,5-dimethylpyrazol-1-yl | CN |
| 3-ethyl-5-methylpyrazol-1-yl | CN |
| 5-methyl-3-(trifluoromethyl)pyrazol-1-yl | CN |
| 3,5-dichloropyrazol-1-yl | CN |
| 5-chloro-3-(trifluoromethyl)pyrazol-1-yl | CN |
| 3,5-dibromopyrazol-1-yl | CN |
| 5-bromo-3-(trifluoromethyl)pyrazol-1-yl | CN |
| 3,5-diethylpyrazol-1-yl | CN |
| 5-ethyl-3-(trifluoromethyl)pyrazol-1-yl | CN |
| 5-methyl-3-(trifluoromethyl)pyrazol-1-yl | i-Pr |
| 5-methyl-3-(trifluoromethyl)pyrazol-1-yl | n-Bu |

TABLE 1C-continued

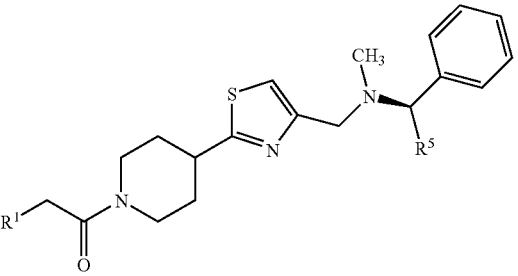

| R¹ | R⁵ |
|---|---|
| 5-methyl-3-(trifluoromethyl)pyrazol-1-yl | i-Bu |
| 5-methyl-3-(trifluoromethyl)pyrazol-1-yl | n-Pen |
| 5-methyl-3-(trifluoromethyl)pyrazol-1-yl | n-Hex |
| 5-methyl-3-(trifluoromethyl)pyrazol-1-yl | ethenyl |
| 5-methyl-3-(trifluoromethyl)pyrazol-1-yl | ethynyl |
| 5-methyl-3-(trifluoromethyl)pyrazol-1-yl | 4-methyl-3-penten-1-yl |
| 5-methyl-3-(trifluoromethyl)pyrazol-1-yl | c-Pr |
| 5-methyl-3-(trifluoromethyl)pyrazol-1-yl | c-Bu |
| 5-methyl-3-(trifluoromethyl)pyrazol-1-yl | c-Pen |
| 5-methyl-3-(trifluoromethyl)pyrazol-1-yl | c-Hex |
| 5-methyl-3-(trifluoromethyl)pyrazol-1-yl | trifluoromethyl |
| 5-methyl-3-(trifluoromethyl)pyrazol-1-yl | 2,2,2-trifluoroethyl |
| 5-methyl-3-(trifluoromethyl)pyrazol-1-yl | 3,3-dichloro-2-propen-1-yl |
| 5-methyl-3-(trifluoromethyl)pyrazol-1-yl | ethynyl |
| 5-methyl-3-(trifluoromethyl)pyrazol-1-yl | propynyl |
| 5-methyl-3-(trifluoromethyl)pyrazol-1-yl | methylethynyl |
| 5-methyl-3-(trifluoromethyl)pyrazol-1-yl | trifluoromethylethynyl |
| 5-methyl-3-(trifluoromethyl)pyrazol-1-yl | 2,2-dichlorocycloprop-1-yl |
| 5-methyl-3-(trifluoromethyl)pyrazol-1-yl | nitro |
| 5-methyl-3-(trifluoromethyl)pyrazol-1-yl | methoxymethyl |
| 5-methyl-3-(trifluoromethyl)pyrazol-1-yl | methoxyethyl |
| 5-methyl-3-(trifluoromethyl)pyrazol-1-yl | 1-methoxyethyl |
| 5-methyl-3-(trifluoromethyl)pyrazol-1-yl | 2-methoxyethyl |
| 5-methyl-3-(trifluoromethyl)pyrazol-1-yl | hydroxymethyl |
| 5-methyl-3-(trifluoromethyl)pyrazol-1-yl | acetyl |
| 5-methyl-3-(trifluoromethyl)pyrazol-1-yl | isobutyryl |
| 5-methyl-3-(trifluoromethyl)pyrazol-1-yl | methoxycarbonyl |
| 5-methyl-3-(trifluoromethyl)pyrazol-1-yl | ethoxycarbonyl |
| 5-methyl-3-(trifluoromethyl)pyrazol-1-yl | methylaminocarbonyl |
| 5-methyl-3-(trifluoromethyl)pyrazol-1-yl | dimethylaminocarbonyl |
| 5-methyl-3-(trifluoromethyl)pyrazol-1-yl | trimethylsilyl |
| 3,5-bis-(trifluoromethyl)pyrazol-1-yl | Et |
| 1-methyl-3-(trifluoromethyl)pyrazol-5-yl | Et |
| 1-methyl-4-(trifluoromethyl)imidazol-2-yl | Et |

TABLE 1D

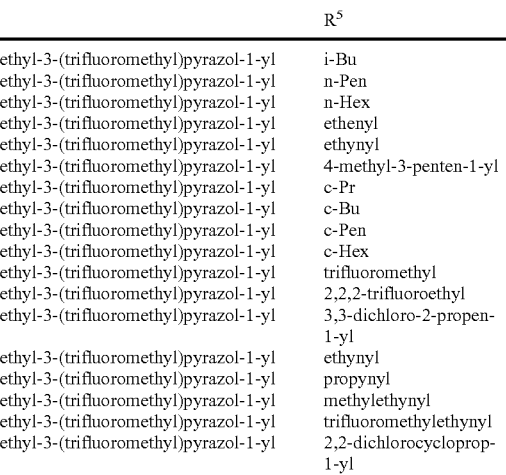

| R¹ | R⁶ |
|---|---|
| 2-methoxyphenyl | 2-methylphenyl |
| 2,5-dichlorophenyl | 2-methylphenyl |
| 5-bromo-2-chlorophenyl | 2-methylphenyl |
| 2-chloro-5-methylphenyl | 2-methylphenyl |
| 2-chloro-5-(trifluoromethyl)phenyl | 2-methylphenyl |
| 2,5-dibromophenyl | 2-methylphenyl |
| 2-bromo-5-methylphenyl | 2-methylphenyl |
| 2-bromo-5-(trifluoromethyl)phenyl | 2-methylphenyl |

TABLE 1D-continued

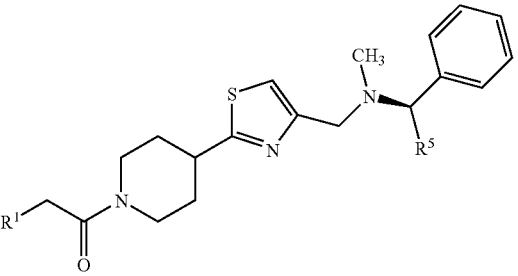

| R¹ | R⁶ |
|---|---|
| 5-chloro-2-methylphenyl | 2-methylphenyl |
| 5-bromo-2-methylphenyl | 2-methylphenyl |
| 2,5-dimethylphenyl | 2-methylphenyl |
| 5-ethyl-2-methylphenyl | 2-methylphenyl |
| 2-methyl-5-(trifluoromethyl)phenyl | 2-methylphenyl |
| 5-bromo-2-methoxyphenyl | 2-methylphenyl |
| 2-methoxy-5-methylphenyl | 2-methylphenyl |
| 2-methoxy-5-(trifluoromethyl)phenyl | 2-methylphenyl |
| 3-(trifluoromethyl)pyrazol-1-yl | 2-methylphenyl |
| 3,5-dimethylpyrazol-1-yl | 2-methylphenyl |
| 3-ethyl-5-methylpyrazol-1-yl | 2-methylphenyl |
| 5-methyl-3-(trifluoromethyl)pyrazol-1-yl | 2-methylphenyl |
| 3,5-dichloropyrazol-1-yl | 2-methylphenyl |
| 5-chloro-3-(trifluoromethyl)pyrazol-1-yl | 2-methylphenyl |
| 3,5-dibromopyrazol-1-yl | 2-methylphenyl |
| 5-bromo-3-(trifluoromethyl)pyrazol-1-yl | 2-methylphenyl |
| 3,5-diethylpyrazol-1-yl | 2-methylphenyl |
| 5-ethyl-3-(trifluoromethyl)pyrazol-1-yl | 2-methylphenyl |
| 2-methoxyphenyl | 4-methylphenyl |
| 2,5-dichlorophenyl | 4-methylphenyl |
| 5-bromo-2-chlorophenyl | 4-methylphenyl |
| 2-chloro-5-methylphenyl | 4-methylphenyl |
| 2-chloro-5-(trifluoromethyl)phenyl | 4-methylphenyl |
| 2,5-dibromophenyl | 4-methylphenyl |
| 2-bromo-5-methylphenyl | 4-methylphenyl |
| 2-bromo-5-(trifluoromethyl)phenyl | 4-methylphenyl |
| 5-chloro-2-methylphenyl | 4-methylphenyl |
| 5-bromo-2-methylphenyl | 4-methylphenyl |
| 2,5-dimethylphenyl | 4-methylphenyl |
| 5-ethyl-2-methylphenyl | 4-methylphenyl |
| 2-methyl-5-(trifluoromethyl)phenyl | 4-methylphenyl |
| 5-bromo-2-methoxyphenyl | 4-methylphenyl |
| 2-methoxy-5-methylphenyl | 4-methylphenyl |
| 2-methoxy-5-(trifluoromethyl)phenyl | 4-methylphenyl |
| 3-(trifluoromethyl)pyrazol-1-yl | 4-methylphenyl |
| 3,5-dimethylpyrazol-1-yl | 4-methylphenyl |
| 3-ethyl-5-methylpyrazol-1-yl | 4-methylphenyl |
| 5-methyl-3-(trifluoromethyl)pyrazol-1-yl | 4-methylphenyl |
| 3,5-dichloropyrazol-1-yl | 4-methylphenyl |
| 5-chloro-3-(trifluoromethyl)pyrazol-1-yl | 4-methylphenyl |
| 3,5-dibromopyrazol-1-yl | 4-methylphenyl |
| 5-bromo-3-(trifluoromethyl)pyrazol-1-yl | 4-methylphenyl |
| 3,5-diethylpyrazol-1-yl | 4-methylphenyl |
| 5-ethyl-3-(trifluoromethyl)pyrazol-1-yl | 4-methylphenyl |
| 2-methoxyphenyl | 4-chlorophenyl |
| 2,5-dichlorophenyl | 4-chlorophenyl |
| 5-bromo-2-chlorophenyl | 4-chlorophenyl |
| 2-chloro-5-methylphenyl | 4-chlorophenyl |
| 2-chloro-5-(trifluoromethyl)phenyl | 4-chlorophenyl |
| 2,5-dibromophenyl | 4-chlorophenyl |
| 2-bromo-5-methylphenyl | 4-chlorophenyl |
| 2-bromo-5-(trifluoromethyl)phenyl | 4-chlorophenyl |
| 5-chloro-2-methylphenyl | 4-chlorophenyl |
| 5-bromo-2-methylphenyl | 4-chlorophenyl |
| 2,5-dimethylphenyl | 4-chlorophenyl |
| 5-ethyl-2-methylphenyl | 4-chlorophenyl |
| 2-methyl-5-(trifluoromethyl)phenyl | 4-chlorophenyl |
| 5-bromo-2-methoxyphenyl | 4-chlorophenyl |
| 2-methoxy-5-methylphenyl | 4-chlorophenyl |
| 2-methoxy-5-(trifluoromethyl)phenyl | 4-chlorophenyl |
| 3-(trifluoromethyl)pyrazol-1-yl | 4-chlorophenyl |
| 3,5-dimethylpyrazol-1-yl | 4-chlorophenyl |
| 3-ethyl-5-methylpyrazol-1-yl | 4-chlorophenyl |
| 5-methyl-3-(trifluoromethyl)pyrazol-1-yl | 4-chlorophenyl |
| 3,5-dichloropyrazol-1-yl | 4-chlorophenyl |

TABLE 1D-continued

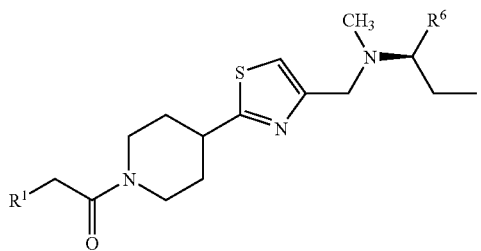

| R¹ | R⁶ |
|---|---|
| 5-chloro-3-(trifluoromethyl)pyrazol-1-yl | 4-chlorophenyl |
| 3,5-dibromopyrazol-1-yl | 4-chlorophenyl |
| 5-bromo-3-(trifluoromethyl)pyrazol-1-yl | 4-chlorophenyl |
| 3,5-diethylpyrazol-1-yl | 4-chlorophenyl |
| 5-ethyl-3-(trifluoromethyl)pyrazol-1-yl | 4-chlorophenyl |
| 5-methyl-3-(trifluoromethyl)pyrazol-1-yl | 2-ethylphenyl |
| 5-methyl-3-(trifluoromethyl)pyrazol-1-yl | 4-t-butylphenyl |
| 5-methyl-3-(trifluoromethyl)pyrazol-1-yl | 4-allylphenyl |
| 5-methyl-3-(trifluoromethyl)pyrazol-1-yl | 4-ethynylphenyl |
| 5-methyl-3-(trifluoromethyl)pyrazol-1-yl | 4-cyclopropylphenyl |
| 5-methyl-3-(trifluoromethyl)pyrazol-1-yl | 4-(trifluoromethyl)phenyl |
| 5-methyl-3-(trifluoromethyl)pyrazol-1-yl | 4-(2-chloroethenyl)phenyl |
| 5-methyl-3-(trifluoromethyl)pyrazol-1-yl | 4-bromoethynylphenyl |
| 5-methyl-3-(trifluoromethyl)pyrazol-1-yl | 4-(2,2-dichlorocycloprop-1-yl)phenyl |
| 5-methyl-3-(trifluoromethyl)pyrazol-1-yl | 2-fluorophenyl |
| 5-methyl-3-(trifluoromethyl)pyrazol-1-yl | 3-fluorophenyl |
| 5-methyl-3-(trifluoromethyl)pyrazol-1-yl | 4-fluorophenyl |
| 5-methyl-3-(trifluoromethyl)pyrazol-1-yl | 2-chlorophenyl |
| 5-methyl-3-(trifluoromethyl)pyrazol-1-yl | 4-bromophenyl |
| 5-methyl-3-(trifluoromethyl)pyrazol-1-yl | 4-hydroxyphenyl |
| 5-methyl-3-(trifluoromethyl)pyrazol-1-yl | 4-aminophenyl |
| 5-methyl-3-(trifluoromethyl)pyrazol-1-yl | 4-cyanophenyl |
| 5-methyl-3-(trifluoromethyl)pyrazol-1-yl | 4-nitrophenyl |
| 5-methyl-3-(trifluoromethyl)pyrazol-1-yl | 4-methoxyphenyl |
| 5-methyl-3-(trifluoromethyl)pyrazol-1-yl | 4-(trifluoromethoxy)phenyl |
| 5-methyl-3-(trifluoromethyl)pyrazol-1-yl | 4-(methylthio)phenyl |
| 5-methyl-3-(trifluoromethyl)pyrazole-1-yl | 4-(methylsulfonyl)phenyl |
| (5-methyl-3-(trifluoromethyl)pyrazol-1-yl | 4-(methylsulfonyl)phenyl |
| 5-methyl-3-(trifluoromethyl)pyrazol-1-yl | 4-(trifluoromethylthio)phenyl |
| 5-methyl-3-(trifluoromethyl)pyrazol-1-yl | 4-(trifluoromethylsulfonyl)phenyl |
| 5-methyl-3-(trifluoromethyl)pyrazol-1-yl | 4-(methylamino)phenyl |
| 5-methyl-3-(trifluoromethyl)pyrazol-1-yl | 4-(dimethylamino)phenyl |
| 5-methyl-3-(trifluoromethyl)pyrazol-1-yl | 4-(cyclopropylamino)phenyl |
| 5-methyl-3-(trifluoromethyl)pyrazol-1-yl | 2-(methoxymethyl)phenyl |
| 5-methyl-3-(trifluoromethyl)pyrazol-1-yl | 3,4-(dimethoxy)phenyl |
| 5-methyl-3-(trifluoromethyl)pyrazol-1-yl | 4-acetylphenyl |
| 5-methyl-3-(trifluoromethyl)pyrazol-1-yl | 4-(methoxycarbonyl)phenyl |
| 5-methyl-3-(trifluoromethyl)pyrazol-1-yl | 4-(acetyloxy)phenyl |
| 5-methyl-3-(trifluoromethyl)pyrazol-1-yl | 4-(methylaminocarbonyl)phenyl |
| 5-methyl-3-(trifluoromethyl)pyrazol-1-yl | 4-(dimethylaminocarbonyl)phenyl |
| 5-methyl-3-(trifluoromethyl)pyrazol-1-yl | 4-(trimethylsilyl)phenyl |
| 5-methyl-3-(trifluoromethyl)pyrazol-1-yl | 2,6-difluorophenyl |
| 5-methyl-3-(trifluoromethyl)pyrazol-1-yl | 2,4,6-trifluorophenyl |
| 5-methyl-3-(trifluoromethyl)pyrazol-1-yl | 2,3-dimethylphenyl |
| 5-methyl-3-(trifluoromethyl)pyrazol-1-yl | 2,3-dichlorophenyl |
| 5-methyl-3-(trifluoromethyl)pyrazol-1-yl | 1-naphthalenyl |
| 5-methyl-3-(trifluoromethyl)pyrazol-1-yl | 2-thienyl |
| 5-methyl-3-(trifluoromethyl)pyrazol-1-yl | 2-furyl |
| 5-methyl-3-(trifluoromethyl)pyrazol-1-yl | 1-methyl-2-pyrrolyl |
| 5-methyl-3-(trifluoromethyl)pyrazol-1-yl | 5-thiazolyl |
| 5-methyl-3-(trifluoromethyl)pyrazol-1-yl | 2-oxazolyl |
| 5-methyl-3-(trifluoromethyl)pyrazol-1-yl | 2-thiazolyl |
| 5-methyl-3-(trifluoromethyl)pyrazol-1-yl | 5-oxazolyl |
| 5-methyl-3-(trifluoromethyl)pyrazol-1-yl | 5-isothiazolyl |
| 5-methyl-3-(trifluoromethyl)pyrazol-1-yl | 5-isoxazolyl |
| 5-methyl-3-(trifluoromethyl)pyrazol-1-yl | 1-methyl-5-pyrazolyl |
| 5-methyl-3-(trifluoromethyl)pyrazol-1-yl | 1-methyl-5-imidazolyl |
| 5-methyl-3-(trifluoromethyl)pyrazol-1-yl | 1-methyl-2-imidazolyl |
| 5-methyl-3-(trifluoromethyl)pyrazol-1-yl | 4-methyl-1,2,4-triazolyl-3-yl |
| 5-methyl-3-(trifluoromethyl)pyrazol-1-yl | 1-methyl-1,2,4-triazolyl-5-yl |
| 5-methyl-3-(trifluoromethyl)pyrazol-1-yl | 1,3,4-oxadiazol-2-yl |
| 5-methyl-3-(trifluoromethyl)pyrazol-1-yl | 1,3,4-thiadiazol-2-yl |

TABLE 1D-continued

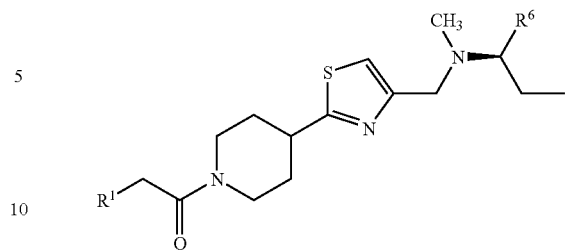

| R¹ | R⁶ |
|---|---|
| 5-methyl-3-(trifluoromethyl)pyrazol-1-yl | 1,2,4-oxadiazol-2-yl |
| 5-methyl-3-(trifluoromethyl)pyrazol-1-yl | 1,2,4-thiadiazol-2-yl |
| 5-methyl-3-(trifluoromethyl)pyrazol-1-yl | 3-thienyl |
| 5-methyl-3-(trifluoromethyl)pyrazol-1-yl | 3-furyl |
| 5-methyl-3-(trifluoromethyl)pyrazol-1-yl | 1-methyl-3-pyrrolyl |
| 5-methyl-3-(trifluoromethyl)pyrazol-1-yl | 1-methyl-3-pyrazolyl |
| 5-methyl-3-(trifluoromethyl)pyrazol-1-yl | 1-methyl-4-pyrazolyl |
| 5-methyl-3-(trifluoromethyl)pyrazol-1-yl | 4-oxazolyl |
| 5-methyl-3-(trifluoromethyl)pyrazol-1-yl | 4-thiazolyl |
| 5-methyl-3-(trifluoromethyl)pyrazol-1-yl | 4-isothiazolyl |
| 5-methyl-3-(trifluoromethyl)pyrazol-1-yl | 4-isoxazolyl |
| 5-methyl-3-(trifluoromethyl)pyrazol-1-yl | 1-methyl-4-imidazolyl |
| 5-methyl-3-(trifluoromethyl)pyrazol-1-yl | 1,2,4-oxadiazol-3-yl |
| 5-methyl-3-(trifluoromethyl)pyrazol-1-yl | 1,2,4-thiadiazol-3-yl |
| 5-methyl-3-(trifluoromethyl)pyrazol-1-yl | 1-methyl-1,2,4-triazolyl-3-yl |
| 5-methyl-3-(trifluoromethyl)pyrazol-1-yl | 2-pyridyl |
| 5-methyl-3-(trifluoromethyl)pyrazol-1-yl | 3,5-dichloro-2-pyridyl |
| 5-methyl-3-(trifluoromethyl)pyrazol-1-yl | 3-pyridyl |
| 5-methyl-3-(trifluoromethyl)pyrazol-1-yl | 4-pyridyl |
| 5-methyl-3-(trifluoromethyl)pyrazol-1-yl | 3-pyrazinyl |
| 5-methyl-3-(trifluoromethyl)pyrazol-1-yl | 2-pyrimidinyl |
| 5-methyl-3-(trifluoromethyl)pyrazol-1-yl | 2-pyridazinyl |
| 5-methyl-3-(trifluoromethyl)pyrazol-1-yl | 4-pyrimidinyl |
| 5-methyl-3-(trifluoromethyl)pyrazol-1-yl | 5-pyrimidinyl |
| 5-methyl-3-(trifluoromethyl)pyrazol-1-yl | 4-pyrazinyl |
| 5-methyl-3-(trifluoromethyl)pyrazol-1-yl | 1,2,4-triazin-6-yl |
| 5-methyl-3-(trifluoromethyl)pyrazol-1-yl | 1,2,4-triazin-3-yl |
| 5-methyl-3-(trifluoromethyl)pyrazol-1-yl | 1,3,5-triazin-2-yl |
| 5-methyl-3-(trifluoromethyl)pyrazol-1-yl | 1,2,4-triazin-5-yl |

TABLE 2

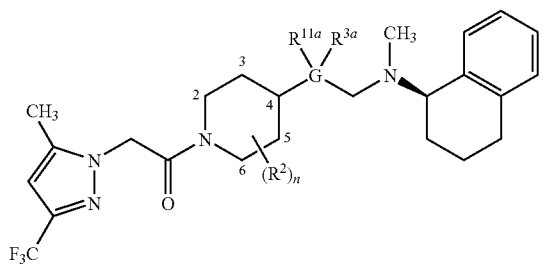

| (R²)ₙ | G | R³ᵃ | R¹¹ᵃ |
|---|---|---|---|
| — | G-1 | H | — |
| — | G-2 | H | — |
| — | G-3 | H | H |
| — | G-4 | H | — |
| — | G-5 | H | — |
| — | G-6 | H | H |
| — | G-7 | — | — |
| — | G-8 | — | — |
| — | G-9 | — | H |
| — | G-10 | H | — |
| — | G-11 | H | — |
| — | G-12 | H | H |
| — | G-13 | H | H |
| — | G-14 | H | — |
| — | G-15 | H | — |

TABLE 2-continued

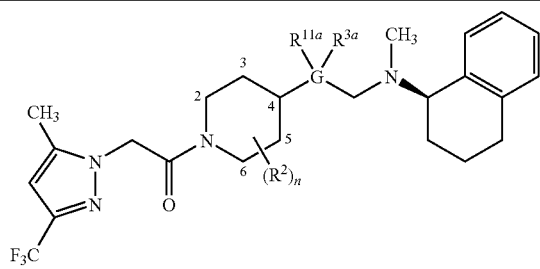

| (R²)ₙ | G | R³ᵃ | R¹¹ᵃ |
|---|---|---|---|
| — | G-16 | H | H |
| — | G-17 | H | — |
| — | G-18 | H | — |
| — | G-19 | — | H |
| — | G-20 | — | — |
| — | G-21 | — | — |
| — | G-22 | H | H |
| — | G-23 | H | — |
| — | G-24 | H | — |
| — | G-25 | H | — |
| — | G-26 | H | — |
| — | G-27 | H | — |
| — | G-28 | H | — |
| — | G-29 | H | — |
| — | G-30 | H | — |
| — | G-31 | H | — |
| — | G-32 | H | — |
| — | G-33 | H | — |
| — | G-34 | H | — |
| — | G-35 | H | — |
| — | G-36 | H | — |
| — | G-37 | H | — |
| — | G-38 | H | — |
| — | G-39 | H | H |
| — | G-40 | H | — |
| — | G-41 | H | — |
| — | G-42 | H | H |
| — | G-43 | H | H |
| — | G-44 | H | — |
| — | G-45 | H | — |

TABLE 2-continued

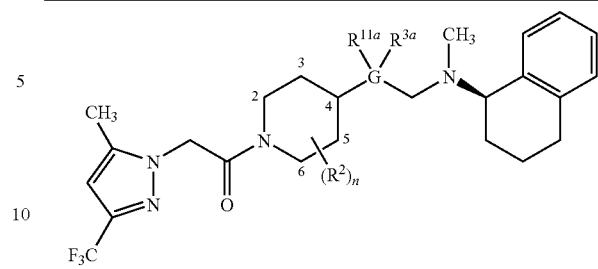

| (R²)ₙ | G | R³ᵃ | R¹¹ᵃ |
|---|---|---|---|
| — | G-46 | — | — |
| — | G-47 | — | — |
| — | G-48 | — | H |
| — | G-49 | H | — |
| — | G-50 | H | — |
| — | G-51 | H | H |
| — | G-52 | H | — |
| — | G-53 | H | — |
| — | G-54 | H | H |
| — | G-55 | — | — |
| — | G-2 | Me | — |
| — | G-2 | Cl | — |
| — | G-2 | F | — |
| — | G-2 | CF₃ | — |
| — | G-14 | n-Pr | — |
| — | G-3 | H | Me |
| — | G-3 | H | n-Pr |
| — | G-26 | 5-Me | — |
| 2-Me | G-1 | H | — |
| 3-Me | G-1 | H | — |
| 2,6-di-Me | G-1 | H | — |
| 3,5-di-Me | G-1 | H | — |
| 3-n-Bu | G-1 | H | — |
| 4-MeO | G-1 | H | — |
| 4-OH | G-1 | H | — |
| 4-Cl | G-1 | H | — |
| 4-Br | G-1 | H | — |
| 4-CN | G-1 | H | — |

TABLE 3*

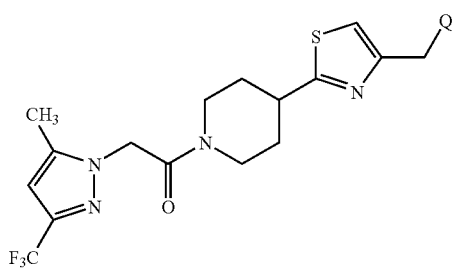

| Q | Qᵃ | R⁵ | (R⁸)ₘ | (R⁹)ⱼ | R¹⁰ | R¹⁵ | (R¹⁶)ₘ/R¹⁶ᵃ |
|---|---|---|---|---|---|---|---|
| Q-2 | Me | — | H | — | — | H | — |
| Q-3 | Me | — | H | — | — | H | — |
| Q-4 | Me | — | H | — | — | H | — |
| Q-5 | Me | — | H | — | H | H | — |
| Q-6 | Me | — | H | — | — | H | — |
| Q-7 | Me | — | H | — | — | H | — |
| Q-8 | Me | — | H | — | — | H | — |
| Q-9 | Me | — | H | — | — | H | — |
| Q-10 | Me | — | H | — | — | H | — |
| Q-11 | Me | — | H | — | H | H | — |
| Q-12 | Me | — | H | — | — | H | — |
| Q-13 | Me | — | H | — | — | H | — |
| Q-14 | Me | — | H | — | — | H | — |
| Q-15 | Me | — | H | — | H | H | — |

TABLE 3*-continued

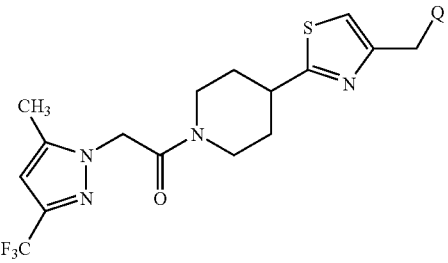

| Q | $Q^a$ | $R^5$ | $(R^8)_m$ | $(R^9)_j$ | $R^{10}$ | $R^{15}$ | $(R^{16})_m/R^{16a}$ |
|---|---|---|---|---|---|---|---|
| Q-2 | Me | — | 2-Me | — | — | H | — |
| Q-2 | Me | — | 2,2-di-Me | — | — | H | — |
| Q-2 | Me | — | 2-Et | — | — | H | — |
| Q-2 | Me | — | H | 6-Me | — | H | — |
| Q-2 | Me | — | H | 6-Cl | — | H | — |
| Q-2 | Me | — | H | 6-OMe | — | H | — |
| Q-2 | Me | — | H | 6-Br | — | H | — |
| Q-2 | Me | — | H | 6-F | — | H | — |
| Q-2 | Me | — | H | 5-OMe | — | H | — |
| Q-2 | Me | — | H | 7-OMe | — | H | — |
| Q-3 | Me | — | 3-Me | — | — | H | — |
| Q-4 | Me | — | 3-Me | — | — | H | — |
| Q-5 | Me | — | H | — | Me | H | — |
| Q-5 | Me | — | H | — | n-Pr | H | — |
| Q-6 | Me | — | H | 3-Cl | — | H | — |
| Q-7 | Me | — | H | 2-Cl | — | H | — |
| Q-8 | Me | — | 2-Me | — | — | H | — |
| Q-8 | Me | — | 2,2-di-Me | — | — | H | — |
| Q-8 | Me | — | 2-Et | — | — | H | — |
| Q-8 | Me | — | 2-n-Pr | — | — | H | — |
| Q-8 | Me | — | 3,3-di-Me | — | — | H | — |
| Q-8 | Me | — | H | 5-Me | — | H | — |
| Q-8 | Me | — | H | 5-Cl | — | H | — |
| Q-8 | Me | — | H | 5-OMe | — | H | — |
| Q-8 | Me | — | H | 5-Br | — | H | — |
| Q-9 | Me | — | 2-Me | — | — | H | — |
| Q-10 | Me | — | 2-Me | — | — | H | — |
| Q-11 | Me | — | H | — | Me | H | — |
| Q-13 | Me | — | H | 2-Me | — | H | — |
| Q-14 | Me | — | H | 2-Me | — | H | — |
| Q-14 | Me | — | H | 2-Cl | — | H | — |
| Q-15 | Me | — | H | — | Me | H | — |
| Q-16 | Me | — | H | — | — | H | — |
| Q-17 | Me | — | H | — | — | H | — |
| Q-18 | Me | — | H | — | Me | H | — |
| Q-19 | Me | — | H | — | — | H | — |
| Q-20 | Me | — | H | — | — | H | — |
| Q-21 | Me | — | H | — | Me | H | — |
| Q-22 | Me | — | H | — | — | H | — |
| Q-23 | Me | — | H | — | — | H | — |
| Q-24 | Me | — | H | — | — | H | — |
| Q-25 | Me | — | H | — | — | H | — |
| Q-26 | Me | — | H | — | — | H | — |
| Q-27 | Me | — | H | — | — | H | — |
| Q-28 | Me | — | H | — | — | H | — |
| Q-29 | Me | — | H | — | — | H | — |
| Q-30 | Me | — | H | — | — | H | — |
| Q-31 | Me | — | H | — | — | H | — |
| Q-32 | Me | — | H | — | — | H | — |
| Q-33 | Me | — | H | — | Me | H | — |
| Q-34 | Me | — | H | — | — | H | — |
| Q-35 | Me | — | H | — | — | H | — |
| Q-36 | Me | — | H | — | Me | H | — |
| Q-37 | Me | — | H | — | — | H | — |
| Q-38 | Me | — | H | — | — | H | — |
| Q-39 | Me | — | H | — | Me | H | — |
| Q-40 | Me | — | H | — | — | H | — |
| Q-41 | Me | — | H | — | — | H | — |
| Q-42 | Me | — | H | — | — | H | — |
| Q-43 | Me | — | H | — | — | H | — |
| Q-44 | Me | — | H | — | — | H | — |
| Q-45 | Me | — | H | — | — | H | — |
| Q-46 | Me | — | H | — | — | H | — |

TABLE 3*-continued

| Q | Q$^a$ | R$^5$ | (R$^8$)$_m$ | (R$^9$)$_j$ | R$^{10}$ | R$^{15}$ | (R$^{16}$)$_m$/R$^{16a}$ |
|---|---|---|---|---|---|---|---|
| Q-47 | Me | — | H | — | — | H | — |
| Q-48 | Me | — | H | — | — | H | — |
| Q-49 | Me | — | H | — | — | H | — |
| Q-50 | Me | — | H | — | — | H | — |
| Q-51 | Me | — | H | — | — | H | — |
| Q-52 | Me | — | H | — | — | H | — |
| Q-53 | Me | — | H | — | — | H | — |
| Q-54 | Me | — | H | — | — | H | — |
| Q-55 | Me | — | H | — | — | H | — |
| Q-56 | Me | — | H | — | — | H | — |
| Q-57 | Me | — | H | — | — | H | — |
| Q-58 | — | — | H | — | — | H | — |
| Q-59 | — | — | H | — | — | H | — |
| Q-60 | — | — | H | — | — | H | — |
| Q-61 | — | — | H | — | — | H | — |
| Q-62 | — | — | H | — | — | H | — |
| Q-63 | — | — | H | — | — | H | — |
| Q-64 | — | — | H | — | — | H | — |
| Q-65 | — | — | H | — | — | H | — |
| Q-66 | — | — | H | — | — | H | — |
| Q-67 | — | — | H | — | — | H | — |
| Q-68 | — | — | H | — | — | H | — |
| Q-69 | — | — | H | — | — | H | — |
| Q-70 | — | Et | — | — | — | H | — |
| Q-71 | — | Et | — | — | — | H | — |
| Q-72 | — | Et | — | — | — | H | — |
| Q-73 | Me | — | — | — | — | H | — |
| Q-74 | Me | — | — | — | — | H | — |
| Q-75 | Me | Me | — | — | — | Me | — |
| Q-76 | — | — | — | — | — | — | 3-Ph |
| Q-77 | — | — | — | — | — | — | 4-Ph |
| Q-78 | — | — | — | — | — | — | 4-Ph |
| Q-79 | — | — | — | — | — | — | — |
| Q-80 | — | — | — | — | — | — | 4-Ph |
| Q-81 | — | — | — | — | — | — | 1-Me |
| Q-82 | — | — | — | — | — | — | — |
| Q-83 | Me | — | — | — | — | H | 2-Ph |
| Q-84 | Me | — | — | — | — | H | 2-Ph |
| Q-85 | Me | — | — | — | — | H | 2-Ph |
| Q-2 | Me | — | 4-Me | — | — | H | — |
| Q-2 | Me | — | 4,4-di-Me | — | — | H | — |
| Q-2 | Me | — | 4-Et | — | — | H | — |
| Q-2 | Me | — | 2-OH | — | — | H | — |
| Q-2 | Me | — | 4-OH | — | — | H | — |
| Q-2 | Me | — | 4-OMe | — | — | H | — |
| Q-2 | Me | — | 4-SMe | — | — | H | — |
| Q-2 | Me | — | 4-SOMe | — | — | H | — |
| Q-2 | Me | — | 4-SO$_2$Me | — | — | H | — |
| Q-2 | Me | — | 4-OCF$_3$ | — | — | H | — |
| Q-2 | Me | — | 2-CF$_3$ | — | — | H | — |
| Q-2 | Me | — | 4-NH$_2$ | — | — | H | — |
| Q-2 | Me | — | 2-n-Bu | — | — | H | — |
| Q-2 | Me | — | 2-propenyl | — | — | H | — |
| Q-2 | Me | — | 2-propynyl | — | — | H | — |
| Q-2 | Me | — | 4-Cl | — | — | H | — |
| Q-2 | Me | — | 2-CN | — | — | H | — |
| Q-2 | Me | — | 4-CN | — | — | H | — |
| Q-2 | Me | — | 4-O-t-Bu | — | — | H | — |
| Q-2 | Me | — | 4-NHMe | — | — | H | — |
| Q-2 | Me | — | 4-N(Me)Me | — | — | H | — |
| Q-2 | Me | — | 2-MeOMe | — | — | H | — |
| Q-2 | Me | — | 4-CH$_2$OH | — | — | H | — |
| Q-2 | Me | — | 4-Ac | — | — | H | — |

TABLE 3*-continued

| Q | Q$^a$ | R$^5$ | (R$^8$)$_m$ | (R$^9$)$_j$ | R$^{10}$ | R$^{15}$ | (R$^{16}$)$_m$/R$^{16a}$ |
|---|---|---|---|---|---|---|---|
| Q-2 | Me | — | 4-COOMe | — | — | H | — |
| Q-2 | Me | — | 4-OAc | — | — | H | — |
| Q-2 | Me | — | 4-O(C=O)-n-Bu | — | — | H | — |
| Q-2 | Me | — | 4-OEt | — | — | H | — |
| Q-2 | Me | — | 4-O(C=O)Et | — | — | H | — |
| Q-2 | Me | — | 4-SAc | — | — | H | — |
| Q-2 | Me | — | 4-CONHMe | — | — | H | — |
| Q-2 | Me | — | 4-CONMe$_2$ | — | — | H | — |
| Q-2 | H | — | 2-Me | — | — | H | — |
| Q-2 | H | — | 2,2-di-Me | — | — | H | — |
| Q-2 | H | — | 4-Me | — | — | H | — |
| Q-2 | H | — | 4,4-di-Me | — | — | H | — |
| Q-2 | H | — | 4-OH | — | — | H | — |
| Q-2 | H | — | 4-OMe | — | — | H | — |
| Q-2 | H | — | 4-OAc | — | — | H | — |
| Q-2 | Me | — | 2-Me | — | — | Me | — |
| Q-2 | Me | — | 2,2-di-Me | — | — | Me | — |
| Q-2 | Me | — | 4-Me | — | — | Me | — |
| Q-2 | Me | — | 4,4-di-Me | — | — | Me | — |
| Q-2 | Me | — | 4-OH | — | — | Me | — |
| Q-2 | Me | — | 4-OMe | — | — | Me | — |
| Q-2 | Me | — | 4-OAc | — | — | Me | — |
| Q-2 | Et | — | H | — | — | H | — |
| Q-2 | Pr | — | H | — | — | H | — |
| Q-2 | 2-propenyl | — | H | — | — | H | — |
| Q-2 | 2-propynyl | — | H | — | — | H | — |
| Q-2 | c-propyl | — | H | — | — | H | — |
| Q-2 | CF$_3$ | — | H | — | — | H | — |
| Q-2 | CN | — | H | — | — | H | — |
| Q-2 | OH | — | H | — | — | H | — |
| Q-2 | OMe | — | H | — | — | H | — |
| Q-2 | CH$_2$OMe | — | H | — | — | H | — |
| Q-2 | CH$_2$OH | — | H | — | — | H | — |
| Q-2 | Ac | — | H | — | — | H | — |
| Q-2 | COEt | — | H | — | — | H | — |
| Q-2 | CO$_2$Me | — | H | — | — | H | — |
| Q-2 | CONHMe | — | H | — | — | H | — |
| Q-2 | CON(Me)$_2$ | — | H | — | — | H | — |
| Q-8 | Me | — | 3-Me | — | — | H | — |
| Q-8 | Me | — | 3,3-di-Me | — | — | H | — |
| Q-8 | Me | — | 3-OH | — | — | H | — |
| Q-8 | Me | — | 3-OMe | — | — | H | — |
| Q-8 | Me | — | 3-OAc | — | — | H | — |
| Q-8 | Me | — | 2-Et | — | — | H | — |
| Q-8 | H | — | H | — | — | H | — |
| Q-14 | Me | — | 2-Me | — | — | H | — |
| Q-14 | Me | — | 2,2-di-Me | — | — | H | — |
| Q-14 | Me | — | 3-Me | — | — | H | — |
| Q-14 | Me | — | 3,3-di-Me | — | — | H | — |
| Q-14 | Me | — | 3-OH | — | — | H | — |
| Q-14 | Me | — | 3-OMe | — | — | H | — |
| Q-14 | Me | — | 3-OAc | — | — | H | — |
| Q-14 | Me | — | 2-Et | — | — | H | — |
| Q-14 | Me | — | H | — | — | H | — |
| Q-23 | Me | — | 2-Me | — | — | H | — |
| Q-23 | Me | — | 2,2-di-Me | — | — | H | — |
| Q-23 | Me | — | 3-Me | — | — | H | — |
| Q-23 | Me | — | 3,3-di-Me | — | — | H | — |
| Q-23 | H | — | H | — | — | H | — |
| Q-41 | Me | — | 2-Me | — | — | H | — |
| Q-41 | Me | — | 2,2-di-Me | — | — | H | — |
| Q-41 | H | — | H | — | — | H | — |
| Q-70 | — | Me | — | — | — | Me | — |

TABLE 3*-continued

| Q | Q$^a$ | R$^5$ | (R$^8$)$_m$ | (R$^9$)$_j$ | R$^{10}$ | R$^{15}$ | (R$^{16}$)$_m$/R$^{16a}$ |
|---|---|---|---|---|---|---|---|
| Q-71 | — | Me | — | — | — | Me | — |
| Q-78 | — | — | — | — | — | — | H |
| Q-78 | — | — | — | — | — | — | 4-Me |
| Q-78 | — | — | — | — | — | — | 4-Et |
| Q-78 | — | — | — | — | — | — | 4-i-Pr |
| Q-78 | — | — | — | — | — | — | 4-t-Bu |
| Q-78 | — | — | — | — | — | — | 4-propen-2-yl |
| Q-78 | — | — | — | — | — | — | 4-propyn-2-yl |
| Q-78 | — | — | — | — | — | — | 4-c-propyl |
| Q-78 | — | — | — | — | — | — | 4-c-hexyl |
| Q-78 | — | — | — | — | — | — | 4-CF$_3$ |
| Q-78 | — | — | — | — | — | — | 4-CH$_2$CF$_3$ |
| Q-78 | — | — | — | — | — | — | 4-SO$_2$Me |
| Q-78 | — | — | — | — | — | — | 4-CH$_2$OH |
| Q-78 | — | — | — | — | — | — | 4-Ac |
| Q-78 | — | — | — | — | — | — | 4-COEt |
| Q-78 | — | — | — | — | — | — | 4-COO-t-Bu |
| Q-78 | — | — | — | — | — | — | 4-benzyl |
| Q-78 | — | — | — | — | — | — | 4-(4-Cl-Ph) |
| Q-77 | — | — | — | — | — | — | — |
| Q-77 | — | — | — | — | — | — | 4-Me |
| Q-77 | — | — | — | — | — | — | 4-t-Bu |
| Q-77 | — | — | — | — | — | — | 4-OH |
| Q-77 | — | — | — | — | — | — | 4-OMe |
| Q-77 | — | — | — | — | — | — | 4-OPr |
| Q-77 | — | — | — | — | — | — | 4-Br |
| Q-77 | — | — | — | — | — | — | 4-Cl |
| Q-77 | — | — | — | — | — | — | 4-NH$_2$ |
| Q-77 | — | — | — | — | — | — | 4-NHMe |
| Q-77 | — | — | — | — | — | — | 4-N(Et)$_2$ |
| Q-77 | — | — | — | — | — | — | 4-CN |
| Q-77 | — | — | — | — | — | — | 4-NO$_2$ |
| Q-77 | — | — | — | — | — | — | 4-OCF$_3$ |
| Q-77 | — | — | — | — | — | — | 4-SMe |
| Q-77 | — | — | — | — | — | — | 4-SO-n-Bu |
| Q-77 | — | — | — | — | — | — | 4-SCHF$_2$ |
| Q-77 | — | — | — | — | — | — | 4-NHMe |
| Q-77 | — | — | — | — | — | — | 4-N(Me)$_2$ |
| Q-77 | — | — | — | — | — | — | 4-MeOMe |
| Q-77 | — | — | — | — | — | — | 4-CO$_2$Me |
| Q-77 | — | — | — | — | — | — | 4-OAc |
| Q-77 | — | — | — | — | — | — | 4-CONHMe |
| Q-77 | — | — | — | — | — | — | 4-trimethylsilyl |
| Q-77 | — | — | — | — | — | — | 3-Ph |
| Q-77 | — | — | — | — | — | — | 3-Me |
| Q-77 | — | — | — | — | — | — | 2-Ph |
| Q-75 | Me | Et | — | — | — | Et | — |
| Q-75 | Me | Et | — | — | — | Me | — |
| Q-75 | Me | Me | — | — | — | i-Pr | — |

Notes:

*The definitions of R$^5$, R$^{10}$, R$^{15}$, (R$^{16}$)$_m$, R$^{16a}$, Q$^a$, (R$^8$)$_m$ and (R$^9$)$_j$ in the compounds of Table 3 are shown in Embodiment 50 unless otherwise noted.

TABLE 4

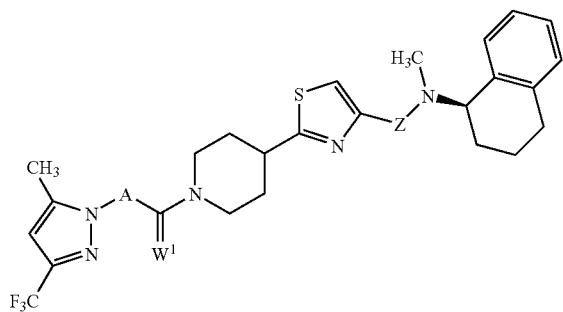

| A | W¹ | Z |
|---|---|---|
| —CH$_2$— | S | —CH$_2$— |
| —NH— | S | —CH$_2$— |
| —NH— | O | —CH$_2$— |
| —CH$_2$— | O | —CH$_2$CH$_2$— |
| —CH$_2$— | O | —CH$_2$CH$_2$CH$_2$— |
| —CH$_2$— | O | —CH(Me)— |
| —CH$_2$— | O | —CH(Et)— |
| —CH$_2$— | O | —CH(CN)— |
| —CH$_2$— | O | —CH(i-Bu)— |
| —CH$_2$— | O | —CH(CF$_3$)— |
| —CH$_2$— | O | —CHCl— |
| —CH$_2$— | O | —CH(C≡CH)— |
| —CH$_2$— | O | —CH(CH=CH$_2$)— |
| —CH$_2$— | O | —CH(OH)CH$_2$— |
| —CH$_2$— | O | —CH(OMe)— |
| —CH$_2$— | O | —CH(SMe)— |
| —CH$_2$— | O | —CH(S=OMe)— |
| —CH$_2$— | O | —CH(SO$_2$Me)— |
| —CH$_2$— | O | —CH(Ac)— |
| —CH$_2$— | O | —CHCO$_2$Me— |
| —CH$_2$— | O | —CHCONMe$_2$— |
| —CH$_2$— | O | —CH(OMe)CH$_2$— |
| —CH$_2$— | O | —CH(SO$_2$Me)CH$_2$— |
| —CH$_2$— | O | —CH$_2$C(CN)$_2$— |
| —CH$_2$CH$_2$— | O | —(C=O)— |
| —CH$_2$CH$_2$CH$_2$— | O | —(C=O)— |
| —CH(Me)— | O | —(C=O)— |
| —CH(Et)— | O | —(C=O)— |
| —CH(CN)— | O | —(C=O)— |
| —CH(i-Bu)— | O | —(C=O)— |
| —CH(CF$_3$)— | O | —(C=O)— |
| —CHCl— | O | —(C=O)— |
| —CH(C≡CH)— | O | —(C=O)— |
| —CH(CH=CH$_2$)— | O | —(C=O)— |
| —CH(OH)CH$_2$— | O | —(C=O)— |
| —CH(OMe)— | O | —(C=O)— |
| —CH(SMe)— | O | —(C=O)— |
| —CH(SOMe)— | O | —(C=O)— |
| —CH(SO$_2$Me)— | O | —(C=O)— |
| —CHAc— | O | —(C=O)— |
| —CH(CO$_2$Me)— | O | —(C=O)— |
| —CH(CONMe$_2$)— | O | —(C=O)— |
| —CH(OMe)CH$_2$— | O | —(C=O)— |
| —CH(SO$_2$Me)CH$_2$— | O | —(C=O)— |
| —CH$_2$C(CN)$_2$— | O | —(C=O)— |

TABLE 4-continued

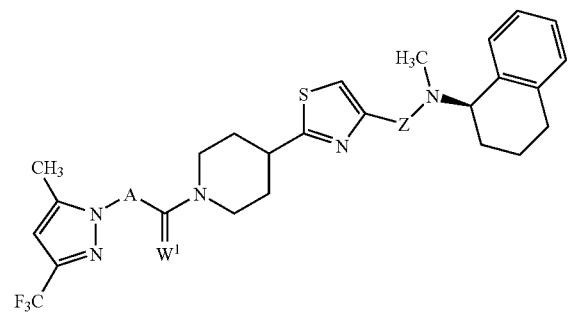

| A | W¹ | Z |
|---|---|---|
| —CH$_2$C(OH)— | O | —(C=O)— |
| —CH(CHO)— | O | —(C=O)— |
| —CH(CO$_2$Et)— | O | —(C=O)— |
| —CH(CO$_2$-n-Pr)— | O | —(C=O)— |
| —CH(CO$_2$-i-Pr)— | O | —(C=O)— |
| —CH(CO$_2$-n-Bu)— | O | —(C=O)— |
| —CH(CO$_2$-i-Bu)— | O | —(C=O)— |
| —CH(CO$_2$-t-Bu)— | O | —(C=O)— |
| —C(Cl)$_2$— | O | —(C=O)— |
| —CH$_2$CH(Me)— | O | —(C=O)— |
| —CH(COCF$_3$)— | O | —(C=O)— |
| —CH(CH$_2$OCH$_3$)— | O | —(C=O)— |
| —CH(CH$_2$CO$_2$Me)— | O | —(C=O)— |
| —CH(CO$_2$Me)CH$_2$— | O | —(C=O)— |
| —CH(CONHMe)— | O | —(C=O)— |
| —N(Me)— | O | —(C=O)— |
| —N(Et)— | O | —(C=O)— |
| —N(CN)— | O | —(C=O)— |
| —N(OH)— | O | —(C=O)— |
| —N(CHO)— | O | —(C=O)— |
| —N(CH$_2$CH=CH$_2$)— | O | —(C=O)— |
| —N(CH$_2$C≡CH)— | O | —(C=O)— |
| —N(CH$_2$Cl)— | O | —(C=O)— |
| —N(CH$_2$OMe)— | O | —(C=O)— |
| —N(CH$_2$OEt)— | O | —(C=O)— |
| —N(CH$_2$OMe)— | O | —(C=O)— |
| —N(CH$_2$SMe)— | O | —(C=O)— |
| —N(CH$_2$SOMe)— | O | —(C=O)— |
| —N(CH$_2$SO$_2$Me)— | O | —(C=O)— |
| —N(Ac)— | O | —(C=O)— |
| —N(COCF$_3$)— | O | —(C=O)— |
| —N(CO$_2$Me)— | O | —(C=O)— |
| —N(CONMe$_2$)— | O | —(C=O)— |
| —N(CH$_2$CH$_2$OMe)— | O | —(C=O)— |
| —N(SO$_2$Et)— | O | —(C=O)— |
| —N(CH$_2$CHMe$_2$)— | O | —(C=O)— |
| —N(CO$_2$Et)— | O | —(C=O)— |
| —N(CO$_2$-n-Pr)— | O | —(C=O)— |
| —N(CO$_2$-i-Pr)— | O | —(C=O)— |
| —N(CO$_2$-n-Bu)— | O | —(C=O)— |
| —N(CO$_2$-i-Bu)— | O | —(C=O)— |
| —N(CO$_2$-t-Bu)— | O | —(C=O)— |
| —N(SOMe)— | O | —(C=O)— |
| —N(SO$_2$Me)— | O | —(C=O)— |

TABLE 5

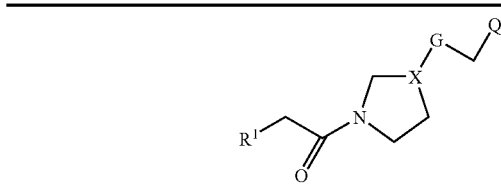

| R¹ | X* | G** | Q |
|---|---|---|---|
| 2,5-dichlorophenyl | X¹ | G-26 | (1R)-N-methyl-1-phenylpropylamino |
| 2-chloro-5-(trifluoromethyl)phenyl | X¹ | G-26 | (1R)-N-methyl-1-phenylpropylamino |

TABLE 5-continued

| R¹ | X* | G** | Q |
|---|---|---|---|
| 2,5-dimethylphenyl | X¹ | G-26 | (1R)-N-methyl-1-phenylpropylamino |
| 2-methyl-5-(trifluoromethyl)phenyl | X¹ | G-26 | (1R)-N-methyl-1-phenylpropylamino |
| 3,5-dimethylpyrazol-1-yl | X¹ | G-26 | (1R)-N-methyl-1-phenylpropylamino |
| 5-methyl-3-(trifluoromethyl)pyrazol-1-yl | X¹ | G-26 | (1R)-N-methyl-1-phenylpropylamino |
| 3,5-dichloropyrazol-1-yl | X¹ | G-26 | (1R)-N-methyl-1-phenylpropylamino |
| 5-chloro-3-(trifluoromethyl)pyrazol-1-yl | X¹ | G-26 | (1R)-N-methyl-1-phenylpropylamino |
| 3,5-dibromopyrazol-1-yl | X¹ | G-26 | (1R)-N-methyl-1-phenylpropylamino |
| 5-bromo-3-(trifluoromethyl)pyrazol-1-yl | X¹ | G-26 | (1R)-N-methyl-1-phenylpropylamino |
| 3,5-diethylpyrazol-1-yl | X¹ | G-26 | (1R)-N-methyl-1-phenylpropylamino |
| 5-ethyl-3-(trifluoromethyl)pyrazol-1-yl | X¹ | G-26 | (1R)-N-methyl-1-phenylpropylamino |
| 3,5-bis-(trifluoromethyl)pyrazol-1-yl | X¹ | G-26 | (1R)-N-methyl-1-phenylpropylamino |
| 3-methyl-5-(trifluoromethyl)pyrazol-1-yl | X¹ | G-26 | (1R)-N-methyl-1-phenylpropylamino |
| 3-chloro-5-(trifluoromethyl)pyrazol-1-yl | X¹ | G-26 | (1R)-N-methyl-1-phenylpropylamino |
| 2,5-dichlorophenyl | X¹ | G-26 | (1R)-N-methyl-1,2,3,4-tetrahydro-1-naphthalenylamino |
| 2-chloro-5-(trifluoromethyl)phenyl | X¹ | G-26 | (1R)-N-methyl-1,2,3,4-tetrahydro-1-naphthalenylamino |
| 2,5-dimethylphenyl | X¹ | G-26 | (1R)-N-methyl-1,2,3,4-tetrahydro-1-naphthalenylamino |
| 2-methyl-5-(trifluoromethyl)phenyl | X¹ | G-26 | (1R)-N-methyl-1,2,3,4-tetrahydro-1-naphthalenylamino |
| 3,5-dimethylpyrazol-1-yl | X¹ | G-26 | (1R)-N-methyl-1,2,3,4-tetrahydro-1-naphthalenylamino |
| 5-methyl-3-(trifluoromethyl)pyrazol-1-yl | X¹ | G-26 | (1R)-N-methyl-1,2,3,4-tetrahydro-1-naphthalenylamino |
| 3,5-dichloropyrazol-1-yl | X¹ | G-26 | (1R)-N-methyl-1,2,3,4-tetrahydro-1-naphthalenylamino |
| 5-chloro-3-(trifluoromethyl)pyrazol-1-yl | X¹ | G-26 | (1R)-N-methyl-1,2,3,4-tetrahydro-1-naphthalenylamino |
| 3,5-dibromopyrazol-1-yl | X¹ | G-26 | (1R)-N-methyl-1,2,3,4-tetrahydro-1-naphthalenylamino |
| 5-bromo-3-(trifluoromethyl)pyrazol-1-yl | X¹ | G-26 | (1R)-N-methyl-1,2,3,4-tetrahydro-1-naphthalenylamino |
| 3,5-diethylpyrazol-1-yl | X¹ | G-26 | (1R)-N-methyl-1,2,3,4-tetrahydro-1-naphthalenylamino |
| 5-ethyl-3-(trifluoromethyl)pyrazol-1-yl | X¹ | G-26 | (1R)-N-methyl-1,2,3,4-tetrahydro-1-naphthalenylamino |
| 3,5-bis-(trifluoromethyl)pyrazol-1-yl | X¹ | G-26 | (1R)-N-methyl-1,2,3,4-tetrahydro-1-naphthalenylamino |
| 3-methyl-5-(trifluoromethyl)pyrazol-1-yl | X¹ | G-26 | (1R)-N-methyl-1,2,3,4-tetrahydro-1-naphthalenylamino |
| 3-chloro-5-(trifluoromethyl)pyrazol-1-yl | X¹ | G-26 | (1R)-N-methyl-1,2,3,4-tetrahydro-1-naphthalenylamino |
| 2,5-dichlorophenyl | X¹ | G-26 | (1R)-N-methyl-1-indanylamino |
| 2-chloro-5-(trifluoromethyl)phenyl | X¹ | G-26 | (1R)-N-methyl-1-indanylamino |
| 2,5-dimethylphenyl | X¹ | G-26 | (1R)-N-methyl-1-indanylamino |
| 2-methyl-5-(trifluoromethyl)phenyl | X¹ | G-26 | (1R)-N-methyl-1-indanylamino |
| 3,5-dimethylpyrazol-1-yl | X¹ | G-26 | (1R)-N-methyl-1-indanylamino |
| 5-methyl-3-(trifluoromethyl)pyrazol-1-yl | X¹ | G-26 | (1R)-N-methyl-1-indanylamino |
| 3,5-dichloropyrazol-1-yl | X¹ | G-26 | (1R)-N-methyl-1-indanylamino |
| 5-chloro-3-(trifluoromethyl)pyrazol-1-yl | X¹ | G-26 | (1R)-N-methyl-1-indanylamino |
| 3,5-dibromopyrazol-1-yl | X¹ | G-26 | (1R)-N-methyl-1-indanylamino |
| 5-bromo-3-(trifluoromethyl)pyrazol-1-yl | X¹ | G-26 | (1R)-N-methyl-1-indanylamino |
| 3,5-diethylpyrazol-1-yl | X¹ | G-26 | (1R)-N-methyl-1-indanylamino |
| 5-ethyl-3-(trifluoromethyl)pyrazol-1-yl | X¹ | G-26 | (1R)-N-methyl-1-indanylamino |
| 3,5-bis-(trifluoromethyl)pyrazol-1-yl | X¹ | G-26 | (1R)-N-methyl-1-indanylamino |
| 3-methyl-5-(trifluoromethyl)pyrazol-1-yl | X¹ | G-26 | (1R)-N-methyl-1-indanylamino |
| 3-chloro-5-(trifluoromethyl)pyrazol-1-yl | X¹ | G-26 | (1R)-N-methyl-1-indanylamino |
| 2,5-dichlorophenyl | X¹ | G-27 | (1R)-N-methyl-1-phenylpropylamino |
| 2-chloro-5-(trifluoromethyl)phenyl | X¹ | G-27 | (1R)-N-methyl-1-phenylpropylamino |
| 2,5-dimethylphenyl | X¹ | G-27 | (1R)-N-methyl-1-phenylpropylamino |
| 2-methyl-5-(trifluoromethyl)phenyl | X¹ | G-27 | (1R)-N-methyl-1-phenylpropylamino |
| 3,5-dimethylpyrazol-1-yl | X¹ | G-27 | (1R)-N-methyl-1-phenylpropylamino |
| 5-methyl-3-(trifluoromethyl)pyrazol-1-yl | X¹ | G-27 | (1R)-N-methyl-1-phenylpropylamino |
| 3,5-dichloropyrazol-1-yl | X¹ | G-27 | (1R)-N-methyl-1-phenylpropylamino |
| 5-chloro-3-(trifluoromethyl)pyrazol-1-yl | X¹ | G-27 | (1R)-N-methyl-1-phenylpropylamino |
| 3,5-dibromopyrazol-1-yl | X¹ | G-27 | (1R)-N-methyl-1-phenylpropylamino |
| 5-bromo-3-(trifluoromethyl)pyrazol-1-yl | X¹ | G-27 | (1R)-N-methyl-1-phenylpropylamino |
| 3,5-diethylpyrazol-1-yl | X¹ | G-27 | (1R)-N-methyl-1-phenylpropylamino |

TABLE 5-continued

| R¹ | X* | G** | Q |
|---|---|---|---|
| 5-ethyl-3-(trifluoromethyl)pyrazol-1-yl | X¹ | G-27 | (1R)-N-methyl-1-phenylpropylamino |
| 3,5-bis-(trifluoromethyl)pyrazol-1-yl | X¹ | G-27 | (1R)-N-methyl-1-phenylpropylamino |
| 3-methyl-5-(trifluoromethyl)pyrazol-1-yl | X¹ | G-27 | (1R)-N-methyl-1-phenylpropylamino |
| 3-chloro-5-(trifluoromethyl)pyrazol-1-yl | X¹ | G-27 | (1R)-N-methyl-1-phenylpropylamino |
| 2,5-dichlorophenyl | X¹ | G-27 | (1R)-N-methyl-1,2,3,4-tetrahydro-1-naphthalenylamino |
| 2-chloro-5-(trifluoromethyl)phenyl | X¹ | G-27 | (1R)-N-methyl-1,2,3,4-tetrahydro-1-naphthalenylamino |
| 2,5-dimethylphenyl | X¹ | G-27 | (1R)-N-methyl-1,2,3,4-tetrahydro-1-naphthalenylamino |
| 2-methyl-5-(trifluoromethyl)phenyl | X¹ | G-27 | (1R)-N-methyl-1,2,3,4-tetrahydro-1-naphthalenylamino |
| 3,5-dimethylpyrazol-1-yl | X¹ | G-27 | (1R)-N-methyl-1,2,3,4-tetrahydro-1-naphthalenylamino |
| 5-methyl-3-(trifluoromethyl)pyrazol-1-yl | X¹ | G-27 | (1R)-N-methyl-1,2,3,4-tetrahydro-1-naphthalenylamino |
| 3,5-dichloropyrazol-1-yl | X¹ | G-27 | (1R)-N-methyl-1,2,3,4-tetrahydro-1-naphthalenylamino |
| 5-chloro-3-(trifluoromethyl)pyrazol-1-yl | X¹ | G-27 | (1R)-N-methyl-1,2,3,4-tetrahydro-1-naphthalenylamino |
| 3,5-dibromopyrazol-1-yl | X¹ | G-27 | (1R)-N-methyl-1,2,3,4-tetrahydro-1-naphthalenylamino |
| 5-bromo-3-(trifluoromethyl)pyrazol-1-yl | X¹ | G-27 | (1R)-N-methyl-1,2,3,4-tetrahydro-1-naphthalenylamino |
| 3,5-diethylpyrazol-1-yl | X¹ | G-27 | (1R)-N-methyl-1,2,3,4-tetrahydro-1-naphthalenylamino |
| 5-ethyl-3-(trifluoromethyl)pyrazol-1-yl | X¹ | G-27 | (1R)-N-methyl-1,2,3,4-tetrahydro-1-naphthalenylamino |
| 3,5-bis-(trifluoromethyl)pyrazol-1-yl | X¹ | G-27 | (1R)-N-methyl-1,2,3,4-tetrahydro-1-naphthalenylamino |
| 3-methyl-5-(trifluoromethyl)pyrazol-1-yl | X¹ | G-27 | (1R)-N-methyl-1,2,3,4-tetrahydro-1-naphthalenylamino |
| 3-chloro-5-(trifluoromethyl)pyrazol-1-yl | X¹ | G-27 | (1R)-N-methyl-1,2,3,4-tetrahydro-1-naphthalenylamino |
| 2,5-dichlorophenyl | X¹ | G-27 | (1R)-N-methyl-1-indanylamino |
| 2-chloro-5-(trifluoromethyl)phenyl | X¹ | G-27 | (1R)-N-methyl-1-indanylamino |
| 2,5-dimethylphenyl | X¹ | G-27 | (1R)-N-methyl-1-indanylamino |
| 2-methyl-5-(trifluoromethyl)phenyl | X¹ | G-27 | (1R)-N-methyl-1-indanylamino |
| 3,5-dimethylpyrazol-1-yl | X¹ | G-27 | (1R)-N-methyl-1-indanylamino |
| 5-methyl-3-(trifluoromethyl)pyrazol-1-yl | X¹ | G-27 | (1R)-N-methyl-1-indanylamino |
| 3,5-dichloropyrazol-1-yl | X¹ | G-27 | (1R)-N-methyl-1-indanylamino |
| 5-chloro-3-(trifluoromethyl)pyrazol-1-yl | X¹ | G-27 | (1R)-N-methyl-1-indanylamino |
| 3,5-dibromopyrazol-1-yl | X¹ | G-27 | (1R)-N-methyl-1-indanylamino |
| 5-bromo-3-(trifluoromethyl)pyrazol-1-yl | X¹ | G-27 | (1R)-N-methyl-1-indanylamino |
| 3,5-diethylpyrazol-1-yl | X¹ | G-27 | (1R)-N-methyl-1-indanylamino |
| 5-ethyl-3-(trifluoromethyl)pyrazol-1-yl | X¹ | G-27 | (1R)-N-methyl-1-indanylamino |
| 3,5-bis-(trifluoromethyl)pyrazol-1-yl | X¹ | G-27 | (1R)-N-methyl-1-indanylamino |
| 3-methyl-5-(trifluoromethyl)pyrazol-1-yl | X¹ | G-27 | (1R)-N-methyl-1-indanylamino |
| 3-chloro-5-(trifluoromethyl)pyrazol-1-yl | X¹ | G-27 | (1R)-N-methyl-1-indanylamino |
| 2,5-dichlorophenyl | X¹ | G-36 | (1R)-N-methyl-1-phenylpropylamino |
| 2-chloro-5-(trifluoromethyl)phenyl | X¹ | G-36 | (1R)-N-methyl-1-phenylpropylamino |
| 2,5-dimethylphenyl | X¹ | G-36 | (1R)-N-methyl-1-phenylpropylamino |
| 2-methyl-5-(trifluoromethyl)phenyl | X¹ | G-36 | (1R)-N-methyl-1-phenylpropylamino |
| 3,5-dimethylpyrazol-1-yl | X¹ | G-36 | (1R)-N-methyl-1-phenylpropylamino |
| 5-methyl-3-(trifluoromethyl)pyrazol-1-yl | X¹ | G-36 | (1R)-N-methyl-1-phenylpropylamino |
| 3,5-dichloropyrazol-1-yl | X¹ | G-36 | (1R)-N-methyl-1-phenylpropylamino |
| 5-chloro-3-(trifluoromethyl)pyrazol-1-yl | X¹ | G-36 | (1R)-N-methyl-1-phenylpropylamino |
| 3,5-dibromopyrazol-1-yl | X¹ | G-36 | (1R)-N-methyl-1-phenylpropylamino |
| 5-bromo-3-(trifluoromethyl)pyrazol-1-yl | X¹ | G-36 | (1R)-N-methyl-1-phenylpropylamino |
| 3,5-diethylpyrazol-1-yl | X¹ | G-36 | (1R)-N-methyl-1-phenylpropylamino |
| 5-ethyl-3-(trifluoromethyl)pyrazol-1-yl | X¹ | G-36 | (1R)-N-methyl-1-phenylpropylamino |
| 3,5-bis-(trifluoromethyl)pyrazol-1-yl | X¹ | G-36 | (1R)-N-methyl-1-phenylpropylamino |
| 3-methyl-5-(trifluoromethyl)pyrazol-1-yl | X¹ | G-36 | (1R)-N-methyl-1-phenylpropylamino |
| 3-chloro-5-(trifluoromethyl)pyrazol-1-yl | X¹ | G-36 | (1R)-N-methyl-1-phenylpropylamino |
| 2,5-dichlorophenyl | X¹ | G-36 | (1R)-N-methyl-1,2,3,4-tetrahydro-1-naphthalenylamino |

TABLE 5-continued

| R¹ | X* | G** | Q |
|---|---|---|---|
| 2-chloro-5-(trifluoromethyl)phenyl | X¹ | G-36 | (1R)-N-methyl-1,2,3,4-tetrahydro-1-naphthalenylamino |
| 2,5-dimethylphenyl | X¹ | G-36 | (1R)-N-methyl-1,2,3,4-tetrahydro-1-naphthalenylamino |
| 2-methyl-5-(trifluoromethyl)phenyl | X¹ | G-36 | (1R)-N-methyl-1,2,3,4-tetrahydro-1-naphthalenylamino |
| 3,5-dimethylpyrazol-1-yl | X¹ | G-36 | (1R)-N-methyl-1,2,3,4-tetrahydro-1-naphthalenylamino |
| 5-methyl-3-(trifluoromethyl)pyrazol-1-yl | X¹ | G-36 | (1R)-N-methyl-1,2,3,4-tetrahydro-1-naphthalenylamino |
| 3,5-dichloropyrazol-1-yl | X¹ | G-36 | (1R)-N-methyl-1,2,3,4-tetrahydro-1-naphthalenylamino |
| 5-chloro-3-(trifluoromethyl)pyrazol-1-yl | X¹ | G-36 | (1R)-N-methyl-1,2,3,4-tetrahydro-1-naphthalenylamino |
| 3,5-dibromopyrazol-1-yl | X¹ | G-36 | (1R)-N-methyl-1,2,3,4-tetrahydro-1-naphthalenylamino |
| 5-bromo-3-(trifluoromethyl)pyrazol-1-yl | X¹ | G-36 | (1R)-N-methyl-1,2,3,4-tetrahydro-1-naphthalenylamino |
| 3,5-diethylpyrazol-1-yl | X¹ | G-36 | (1R)-N-methyl-1,2,3,4-tetrahydro-1-naphthalenylamino |
| 5-ethyl-3-(trifluoromethyl)pyrazol-1-yl | X¹ | G-36 | (1R)-N-methyl-1,2,3,4-tetrahydro-1-naphthalenylamino |
| 3,5-bis-(trifluoromethyl)pyrazol-1-yl | X¹ | G-36 | (1R)-N-methyl-1,2,3,4-tetrahydro-1-naphthalenylamino |
| 3-methyl-5-(trifluoromethyl)pyrazol-1-yl | X¹ | G-36 | (1R)-N-methyl-1,2,3,4-tetrahydro-1-naphthalenylamino |
| 3-chloro-5-(trifluoromethyl)pyrazol-1-yl | X¹ | G-36 | (1R)-N-methyl-1,2,3,4-tetrahydro-1-naphthalenylamino |
| 2,5-dichlorophenyl | X¹ | G-36 | (1R)-N-methyl-1-indanylamino |
| 2-chloro-5-(trifluoromethyl)phenyl | X¹ | G-36 | (1R)-N-methyl-1-indanylamino |
| 2,5-dimethylphenyl | X¹ | G-36 | (1R)-N-methyl-1-indanylamino |
| 2-methyl-5-(trifluoromethyl)phenyl | X¹ | G-36 | (1R)-N-methyl-1-indanylamino |
| 3,5-dimethylpyrazol-1-yl | X¹ | G-36 | (1R)-N-methyl-1-indanylamino |
| 5-methyl-3-(trifluoromethyl)pyrazol-1-yl | X¹ | G-36 | (1R)-N-methyl-1-indanylamino |
| 3,5-dichloropyrazol-1-yl | X¹ | G-36 | (1R)-N-methyl-1-indanylamino |
| 5-chloro-3-(trifluoromethyl)pyrazol-1-yl | X¹ | G-36 | (1R)-N-methyl-1-indanylamino |
| 3,5-dibromopyrazol-1-yl | X¹ | G-36 | (1R)-N-methyl-1-indanylamino |
| 5-bromo-3-(trifluoromethyl)pyrazol-1-yl | X¹ | G-36 | (1R)-N-methyl-1-indanylamino |
| 3,5-diethylpyrazol-1-yl | X¹ | G-36 | (1R)-N-methyl-1-indanylamino |
| 5-ethyl-3-(trifluoromethyl)pyrazol-1-yl | X¹ | G-36 | (1R)-N-methyl-1-indanylamino |
| 3,5-bis-(trifluoromethyl)pyrazol-1-yl | X¹ | G-36 | (1R)-N-methyl-1-indanylamino |
| 3-methyl-5-(trifluoromethyl)pyrazol-1-yl | X¹ | G-36 | (1R)-N-methyl-1-indanylamino |
| 3-chloro-5-(trifluoromethyl)pyrazol-1-yl | X¹ | G-36 | (1R)-N-methyl-1-indanylamino |
| 2,5-dichlorophenyl | X¹ | G-2 | (1R)-N-methyl-1-phenylpropylamino |
| 2-chloro-5-(trifluoromethyl)phenyl | X¹ | G-2 | (1R)-N-methyl-1-phenylpropylamino |
| 2,5-dimethylphenyl | X¹ | G-2 | (1R)-N-methyl-1-phenylpropylamino |
| 2-methyl-5-(trifluoromethyl)phenyl | X¹ | G-2 | (1R)-N-methyl-1-phenylpropylamino |
| 3,5-dimethylpyrazol-1-yl | X¹ | G-2 | (1R)-N-methyl-1-phenylpropylamino |
| 5-methyl-3-(trifluoromethyl)pyrazol-1-yl | X¹ | G-2 | (1R)-N-methyl-1-phenylpropylamino |
| 3,5-dichloropyrazol-1-yl | X¹ | G-2 | (1R)-N-methyl-1-phenylpropylamino |
| 5-chloro-3-(trifluoromethyl)pyrazol-1-yl | X¹ | G-2 | (1R)-N-methyl-1-phenylpropylamino |
| 3,5-dibromopyrazol-1-yl | X¹ | G-2 | (1R)-N-methyl-1-phenylpropylamino |
| 5-bromo-3-(trifluoromethyl)pyrazol-1-yl | X¹ | G-2 | (1R)-N-methyl-1-phenylpropylamino |
| 3,5-diethylpyrazol-1-yl | X¹ | G-2 | (1R)-N-methyl-1-phenylpropylamino |
| 5-ethyl-3-(trifluoromethyl)pyrazol-1-yl | X¹ | G-2 | (1R)-N-methyl-1-phenylpropylamino |
| 3,5-bis-(trifluoromethyl)pyrazol-1-yl | X¹ | G-2 | (1R)-N-methyl-1-phenylpropylamino |
| 3-methyl-5-(trifluoromethyl)pyrazol-1-yl | X¹ | G-2 | (1R)-N-methyl-1-phenylpropylamino |
| 3-chloro-5-(trifluoromethyl)pyrazol-1-yl | X¹ | G-2 | (1R)-N-methyl-1-phenylpropylamino |
| 2,5-dichlorophenyl | X¹ | G-2 | (1R)-N-methyl-1,2,3,4-tetrahydro-1-naphthalenylamino |
| 2-chloro-5-(trifluoromethyl)phenyl | X¹ | G-2 | (1R)-N-methyl-1,2,3,4-tetrahydro-1-naphthalenylamino |
| 2,5-dimethylphenyl | X¹ | G-2 | (1R)-N-methyl-1,2,3,4-tetrahydro-1-naphthalenylamino |
| 2-methyl-5-(trifluoromethyl)phenyl | X¹ | G-2 | (1R)-N-methyl-1,2,3,4-tetrahydro-1-naphthalenylamino |
| 3,5-dimethylpyrazol-1-yl | X¹ | G-2 | (1R)-N-methyl-1,2,3,4-tetrahydro-1-naphthalenylamino |

TABLE 5-continued

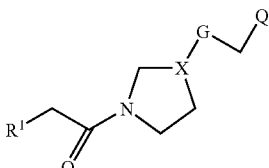

| R¹ | X* | G** | Q |
|---|---|---|---|
| 5-methyl-3-(trifluoromethyl)pyrazol-1-yl | X¹ | G-2 | (1R)-N-methyl-1,2,3,4-tetrahydro-1-naphthalenylamino |
| 3,5-dichloropyrazol-1-yl | X¹ | G-2 | (1R)-N-methyl-1,2,3,4-tetrahydro-1-naphthalenylamino |
| 5-chloro-3-(trifluoromethyl)pyrazol-1-yl | X¹ | G-2 | (1R)-N-methyl-1,2,3,4-tetrahydro-1-naphthalenylamino |
| 3,5-dibromopyrazol-1-yl | X¹ | G-2 | (1R)-N-methyl-1,2,3,4-tetrahydro-1-naphthalenylamino |
| 5-bromo-3-(trifluoromethyl)pyrazol-1-yl | X¹ | G-2 | (1R)-N-methyl-1,2,3,4-tetrahydro-1-naphthalenylamino |
| 3,5-diethylpyrazol-1-yl | X¹ | G-2 | (1R)-N-methyl-1,2,3,4-tetrahydro-1-naphthalenylamino |
| 5-ethyl-3-(trifluoromethyl)pyrazol-1-yl | X¹ | G-2 | (1R)-N-methyl-1,2,3,4-tetrahydro-1-naphthalenylamino |
| 3,5-bis-(trifluoromethyl)pyrazol-1-yl | X¹ | G-2 | (1R)-N-methyl-1,2,3,4-tetrahydro-1-naphthalenylamino |
| 3-methyl-5-(trifluoromethyl)pyrazol-1-yl | X¹ | G-2 | (1R)-N-methyl-1,2,3,4-tetrahydro-1-naphthalenylamino |
| 3-chloro-5-(trifluoromethyl)pyrazol-1-yl | X¹ | G-2 | (1R)-N-methyl-1,2,3,4-tetrahydro-1-naphthalenylamino |
| 2,5-dichlorophenyl | X¹ | G-2 | (1R)-N-methyl-1-indanylamino |
| 2-chloro-5-(trifluoromethyl)phenyl | X¹ | G-2 | (1R)-N-methyl-1-indanylamino |
| 2,5-dimethylphenyl | X¹ | G-2 | (1R)-N-methyl-1-indanylamino |
| 2-methyl-5-(trifluoromethyl)phenyl | X¹ | G-2 | (1R)-N-methyl-1-indanylamino |
| 3,5-dimethylpyrazol-1-yl | X¹ | G-2 | (1R)-N-methyl-1-indanylamino |
| 5-methyl-3-(trifluoromethyl)pyrazol-1-yl | X¹ | G-2 | (1R)-N-methyl-1-indanylamino |
| 3,5-dichloropyrazol-1-yl | X¹ | G-2 | (1R)-N-methyl-1-indanylamino |
| 5-chloro-3-(trifluoromethyl)pyrazol-1-yl | X¹ | G-2 | (1R)-N-methyl-1-indanylamino |
| 3,5-dibromopyrazol-1-yl | X¹ | G-2 | (1R)-N-methyl-1-indanylamino |
| 5-bromo-3-(trifluoromethyl)pyrazol-1-yl | X¹ | G-2 | (1R)-N-methyl-1-indanylamino |
| 3,5-diethylpyrazol-1-yl | X¹ | G-2 | (1R)-N-methyl-1-indanylamino |
| 5-ethyl-3-(trifluoromethyl)pyrazol-1-yl | X¹ | G-2 | (1R)-N-methyl-1-indanylamino |
| 3,5-bis-(trifluoromethyl)pyrazol-1-yl | X¹ | G-2 | (1R)-N-methyl-1-indanylamino |
| 3-methyl-5-(trifluoromethyl)pyrazol-1-yl | X¹ | G-2 | (1R)-N-methyl-1-indanylamino |
| 3-chloro-5-(trifluoromethyl)pyrazol-1-yl | X¹ | G-2 | (1R)-N-methyl-1-indanylamino |
| 2,5-dichlorophenyl | X² | G-1 | (1R)-N-methyl-1-phenylpropylamino |
| 2-chloro-5-(trifluoromethyl)phenyl | X² | G-1 | (1R)-N-methyl-1-phenylpropylamino |
| 2,5-dimethylphenyl | X² | G-1 | (1R)-N-methyl-1-phenylpropylamino |
| 2-methyl-5-(trifluoromethyl)phenyl | X² | G-1 | (1R)-N-methyl-1-phenylpropylamino |
| 3,5-dimethylpyrazol-1-yl | X² | G-1 | (1R)-N-methyl-1-phenylpropylamino |
| 5-methyl-3-(trifluoromethyl)pyrazol-1-yl | X² | G-1 | (1R)-N-methyl-1-phenylpropylamino |
| 3,5-dichloropyrazol-1-yl | X² | G-1 | (1R)-N-methyl-1-phenylpropylamino |
| 5-chloro-3-(trifluoromethyl)pyrazol-1-yl | X² | G-1 | (1R)-N-methyl-1-phenylpropylamino |
| 3,5-dibromopyrazol-1-yl | X² | G-1 | (1R)-N-methyl-1-phenylpropylamino |
| 5-bromo-3-(trifluoromethyl)pyrazol-1-yl | X² | G-1 | (1R)-N-methyl-1-phenylpropylamino |
| 3,5-diethylpyrazol-1-yl | X² | G-1 | (1R)-N-methyl-1-phenylpropylamino |
| 5-ethyl-3-(trifluoromethyl)pyrazol-1-yl | X² | G-1 | (1R)-N-methyl-1-phenylpropylamino |
| 3,5-bis-(trifluoromethyl)pyrazol-1-yl | X² | G-1 | (1R)-N-methyl-1-phenylpropylamino |
| 3-methyl-5-(trifluoromethyl)pyrazol-1-yl | X² | G-1 | (1R)-N-methyl-1-phenylpropylamino |
| 3-chloro-5-(trifluoromethyl)pyrazol-1-yl | X² | G-1 | (1R)-N-methyl-1-phenylpropylamino |
| 2,5-dichlorophenyl | X² | G-1 | (1R)-N-methyl-1,2,3,4-tetrahydro-1-naphthalenylamino |
| 2-chloro-5-(trifluoromethyl)phenyl | X² | G-1 | (1R)-N-methyl-1,2,3,4-tetrahydro-1-naphthalenylamino |
| 2,5-dimethylphenyl | X² | G-1 | (1R)-N-methyl-1,2,3,4-tetrahydro-1-naphthalenylamino |
| 2-methyl-5-(trifluoromethyl)phenyl | X² | G-1 | (1R)-N-methyl-1,2,3,4-tetrahydro-1-naphthalenylamino |
| 3,5-dimethylpyrazol-1-yl | X² | G-1 | (1R)-N-methyl-1,2,3,4-tetrahydro-1-naphthalenylamino |
| 5-methyl-3-(trifluoromethyl)pyrazol-1-yl | X² | G-1 | (1R)-N-methyl-1,2,3,4-tetrahydro-1-naphthalenylamino |
| 3,5-dichloropyrazol-1-yl | X² | G-1 | (1R)-N-methyl-1,2,3,4-tetrahydro-1-naphthalenylamino |
| 5-chloro-3-(trifluoromethyl)pyrazol-1-yl | X² | G-1 | (1R)-N-methyl-1,2,3,4-tetrahydro-1-naphthalenylamino |
| 3,5-dibromopyrazol-1-yl | X² | G-1 | (1R)-N-methyl-1,2,3,4-tetrahydro-1-naphthalenylamino |

TABLE 5-continued

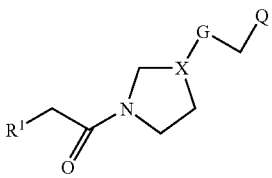

| R¹ | X* | G** | Q |
|---|---|---|---|
| 5-bromo-3-(trifluoromethyl)pyrazol-1-yl | X² | G-1 | (1R)-N-methyl-1,2,3,4-tetrahydro-1-naphthalenylamino |
| 3,5-diethylpyrazol-1-yl | X² | G-1 | (1R)-N-methyl-1,2,3,4-tetrahydro-1-naphthalenylamino |
| 5-ethyl-3-(trifluoromethyl)pyrazol-1-yl | X² | G-1 | (1R)-N-methyl-1,2,3,4-tetrahydro-1-naphthalenylamino |
| 3,5-bis-(trifluoromethyl)pyrazol-1-yl | X² | G-1 | (1R)-N-methyl-1,2,3,4-tetrahydro-1-naphthalenylamino |
| 3-methyl-5-(trifluoromethyl)pyrazol-1-yl | X² | G-1 | (1R)-N-methyl-1,2,3,4-tetrahydro-1-naphthalenylamino |
| 3-chloro-5-(trifluoromethyl)pyrazol-1-yl | X² | G-1 | (1R)-N-methyl-1,2,3,4-tetrahydro-1-naphthalenylamino |
| 2,5-dichlorophenyl | X² | G-1 | (1R)-N-methyl-1-indanylamino |
| 2-chloro-5-(trifluoromethyl)phenyl | X² | G-1 | (1R)-N-methyl-1-indanylamino |
| 2,5-dimethylphenyl | X² | G-1 | (1R)-N-methyl-1-indanylamino |
| 2-methyl-5-(trifluoromethyl)phenyl | X² | G-1 | (1R)-N-methyl-1-indanylamino |
| 3,5-dimethylpyrazol-1-yl | X² | G-1 | (1R)-N-methyl-1-indanylamino |
| 5-methyl-3-(trifluoromethyl)pyrazol-1-yl | X² | G-1 | (1R)-N-methyl-1-indanylamino |
| 3,5-dichloropyrazol-1-yl | X² | G-1 | (1R)-N-methyl-1-indanylamino |
| 5-chloro-3-(trifluoromethyl)pyrazol-1-yl | X² | G-1 | (1R)-N-methyl-1-indanylamino |
| 3,5-dibromopyrazol-1-yl | X² | G-1 | (1R)-N-methyl-1-indanylamino |
| 5-bromo-3-(trifluoromethyl)pyrazol-1-yl | X² | G-1 | (1R)-N-methyl-1-indanylamino |
| 3,5-diethylpyrazol-1-yl | X² | G-1 | (1R)-N-methyl-1-indanylamino |
| 5-ethyl-3-(trifluoromethyl)pyrazol-1-yl | X² | G-1 | (1R)-N-methyl-1-indanylamino |
| 3,5-bis-(trifluoromethyl)pyrazol-1-yl | X² | G-1 | (1R)-N-methyl-1-indanylamino |
| 3-methyl-5-(trifluoromethyl)pyrazol-1-yl | X² | G-1 | (1R)-N-methyl-1-indanylamino |
| 3-chloro-5-(trifluoromethyl)pyrazol-1-yl | X² | G-1 | (1R)-N-methyl-1-indanylamino |
| 2,5-dichlorophenyl | X² | G-2 | (1R)-N-methyl-1-phenylpropylamino |
| 2-chloro-5-(trifluoromethyl)phenyl | X² | G-2 | (1R)-N-methyl-1-phenylpropylamino |
| 2,5-dimethylphenyl | X² | G-2 | (1R)-N-methyl-1-phenylpropylamino |
| 2-methyl-5-(trifluoromethyl)phenyl | X² | G-2 | (1R)-N-methyl-1-phenylpropylamino |
| 3,5-dimethylpyrazol-1-yl | X² | G-2 | (1R)-N-methyl-1-phenylpropylamino |
| 5-methyl-3-(trifluoromethyl)pyrazol-1-yl | X² | G-2 | (1R)-N-methyl-1-phenylpropylamino |
| 3,5-dichloropyrazol-1-yl | X² | G-2 | (1R)-N-methyl-1-phenylpropylamino |
| 5-chloro-3-(trifluoromethyl)pyrazol-1-yl | X² | G-2 | (1R)-N-methyl-1-phenylpropylamino |
| 3,5-dibromopyrazol-1-yl | X² | G-2 | (1R)-N-methyl-1-phenylpropylamino |
| 5-bromo-3-(trifluoromethyl)pyrazol-1-yl | X² | G-2 | (1R)-N-methyl-1-phenylpropylamino |
| 3,5-diethylpyrazol-1-yl | X² | G-2 | (1R)-N-methyl-1-phenylpropylamino |
| 5-ethyl-3-(trifluoromethyl)pyrazol-1-yl | X² | G-2 | (1R)-N-methyl-1-phenylpropylamino |
| 3,5-bis-(trifluoromethyl)pyrazol-1-yl | X² | G-2 | (1R)-N-methyl-1-phenylpropylamino |
| 3-methyl-5-(trifluoromethyl)pyrazol-1-yl | X² | G-2 | (1R)-N-methyl-1-phenylpropylamino |
| 3-chloro-5-(trifluoromethyl)pyrazol-1-yl | X² | G-2 | (1R)-N-methyl-1-phenylpropylamino |
| 2,5-dichlorophenyl | X² | G-2 | (1R)-N-methyl-1,2,3,4-tetrahydro-1-naphthalenylamino |
| 2-chloro-5-(trifluoromethyl)phenyl | X² | G-2 | (1R)-N-methyl-1,2,3,4-tetrahydro-1-naphthalenylamino |
| 2,5-dimethylphenyl | X² | G-2 | (1R)-N-methyl-1,2,3,4-tetrahydro-1-naphthalenylamino |
| 2-methyl-5-(trifluoromethyl)phenyl | X² | G-2 | (1R)-N-methyl-1,2,3,4-tetrahydro-1-naphthalenylamino |
| 3,5-dimethylpyrazol-1-yl | X² | G-2 | (1R)-N-methyl-1,2,3,4-tetrahydro-1-naphthalenylamino |
| 5-methyl-3-(trifluoromethyl)pyrazol-1-yl | X² | G-2 | (1R)-N-methyl-1,2,3,4-tetrahydro-1-naphthalenylamino |
| 3,5-dichloropyrazol-1-yl | X² | G-2 | (1R)-N-methyl-1,2,3,4-tetrahydro-1-naphthalenylamino |
| 5-chloro-3-(trifluoromethyl)pyrazol-1-yl | X² | G-2 | (1R)-N-methyl-1,2,3,4-tetrahydro-1-naphthalenylamino |
| 3,5-dibromopyrazol-1-yl | X² | G-2 | (1R)-N-methyl-1,2,3,4-tetrahydro-1-naphthalenylamino |
| 5-bromo-3-(trifluoromethyl)pyrazol-1-yl | X² | G-2 | (1R)-N-methyl-1,2,3,4-tetrahydro-1-naphthalenylamino |
| 3,5-diethylpyrazol-1-yl | X² | G-2 | (1R)-N-methyl-1,2,3,4-tetrahydro-1-naphthalenylamino |
| 5-ethyl-3-(trifluoromethyl)pyrazol-1-yl | X² | G-2 | (1R)-N-methyl-1,2,3,4-tetrahydro-1-naphthalenylamino |
| 3,5-bis-(trifluoromethyl)pyrazol-1-yl | X² | G-2 | (1R)-N-methyl-1,2,3,4-tetrahydro-1-naphthalenylamino |

TABLE 5-continued

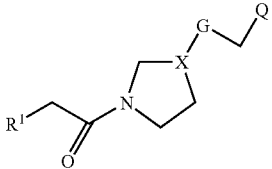

| R¹ | X* | G** | Q |
|---|---|---|---|
| 3-methyl-5-(trifluoromethyl)pyrazol-1-yl | X² | G-2 | (1R)-N-methyl-1,2,3,4-tetrahydro-1-naphthalenylamino |
| 3-chloro-5-(trifluoromethyl)pyrazol-1-yl | X² | G-2 | (1R)-N-methyl-1,2,3,4-tetrahydro-1-naphthalenylamino |
| 2,5-dichlorophenyl | X² | G-2 | (1R)-N-methyl-1-indanylamino |
| 2-chloro-5-(trifluoromethyl)phenyl | X² | G-2 | (1R)-N-methyl-1-indanylamino |
| 2,5-dimethylphenyl | X² | G-2 | (1R)-N-methyl-1-indanylamino |
| 2-methyl-5-(trifluoromethyl)phenyl | X² | G-2 | (1R)-N-methyl-1-indanylamino |
| 3,5-dimethylpyrazol-1-yl | X² | G-2 | (1R)-N-methyl-1-indanylamino |
| 5-methyl-3-(trifluoromethyl)pyrazol-1-yl | X² | G-2 | (1R)-N-methyl-1-indanylamino |
| 3,5-dichloropyrazol-1-yl | X² | G-2 | (1R)-N-methyl-1-indanylamino |
| 5-chloro-3-(trifluoromethyl)pyrazol-1-yl | X² | G-2 | (1R)-N-methyl-1-indanylamino |
| 3,5-dibromopyrazol-1-yl | X² | G-2 | (1R)-N-methyl-1-indanylamino |
| 5-bromo-3-(trifluoromethyl)pyrazol-1-yl | X² | G-2 | (1R)-N-methyl-1-indanylamino |
| 3,5-diethylpyrazol-1-yl | X² | G-2 | (1R)-N-methyl-1-indanylamino |
| 5-ethyl-3-(trifluoromethyl)pyrazol-1-yl | X² | G-2 | (1R)-N-methyl-1-indanylamino |
| 3,5-bis-(trifluoromethyl)pyrazol-1-yl | X² | G-2 | (1R)-N-methyl-1-indanylamino |
| 3-methyl-5-(trifluoromethyl)pyrazol-1-yl | X² | G-2 | (1R)-N-methyl-1-indanylamino |
| 3-chloro-5-(trifluoromethyl)pyrazol-1-yl | X² | G-2 | (1R)-N-methyl-1-indanylamino |
| 2,5-dichlorophenyl | X³ | G-1 | (1R)-N-methyl-1-phenylpropylamino |
| 2-chloro-5-(trifluoromethyl)phenyl | X³ | G-1 | (1R)-N-methyl-1-phenylpropylamino |
| 2,5-dimethylphenyl | X³ | G-1 | (1R)-N-methyl-1-phenylpropylamino |
| 2-methyl-5-(trifluoromethyl)phenyl | X³ | G-1 | (1R)-N-methyl-1-phenylpropylamino |
| 3,5-dimethylpyrazol-1-yl | X³ | G-1 | (1R)-N-methyl-1-phenylpropylamino |
| 5-methyl-3-(trifluoromethyl)pyrazol-1-yl | X³ | G-1 | (1R)-N-methyl-1-phenylpropylamino |
| 3,5-dichloropyrazol-1-yl | X³ | G-1 | (1R)-N-methyl-1-phenylpropylamino |
| 5-chloro-3-(trifluoromethyl)pyrazol-1-yl | X³ | G-1 | (1R)-N-methyl-1-phenylpropylamino |
| 3,5-dibromopyrazol-1-yl | X³ | G-1 | (1R)-N-methyl-1-phenylpropylamino |
| 5-bromo-3-(trifluoromethyl)pyrazol-1-yl | X³ | G-1 | (1R)-N-methyl-1-phenylpropylamino |
| 3,5-diethylpyrazol-1-yl | X³ | G-1 | (1R)-N-methyl-1-phenylpropylamino |
| 5-ethyl-3-(trifluoromethyl)pyrazol-1-yl | X³ | G-1 | (1R)-N-methyl-1-phenylpropylamino |
| 3,5-bis-(trifluoromethyl)pyrazol-1-yl | X³ | G-1 | (1R)-N-methyl-1-phenylpropylamino |
| 3-methyl-5-(trifluoromethyl)pyrazol-1-yl | X³ | G-1 | (1R)-N-methyl-1-phenylpropylamino |
| 3-chloro-5-(trifluoromethyl)pyrazol-1-yl | X³ | G-1 | (1R)-N-methyl-1-phenylpropylamino |
| 2,5-dichlorophenyl | X³ | G-1 | (1R)-N-methyl-1,2,3,4-tetrahydro-1-naphthalenylamino |
| 2-chloro-5-(trifluoromethyl)phenyl | X³ | G-1 | (1R)-N-methyl-1,2,3,4-tetrahydro-1-naphthalenylamino |
| 2,5-dimethylphenyl | X³ | G-1 | (1R)-N-methyl-1,2,3,4-tetrahydro-1-naphthalenylamino |
| 2-methyl-5-(trifluoromethyl)phenyl | X³ | G-1 | (1R)-N-methyl-1,2,3,4-tetrahydro-1-naphthalenylamino |
| 3,5-dimethylpyrazol-1-yl | X³ | G-1 | (1R)-N-methyl-1,2,3,4-tetrahydro-1-naphthalenylamino |
| 5-methyl-3-(trifluoromethyl)pyrazol-1-yl | X³ | G-1 | (1R)-N-methyl-1,2,3,4-tetrahydro-1-naphthalenylamino |
| 3,5-dichloropyrazol-1-yl | X³ | G-1 | (1R)-N-methyl-1,2,3,4-tetrahydro-1-naphthalenylamino |
| 5-chloro-3-(trifluoromethyl)pyrazol-1-yl | X³ | G-1 | (1R)-N-methyl-1,2,3,4-tetrahydro-1-naphthalenylamino |
| 3,5-dibromopyrazol-1-yl | X³ | G-1 | (1R)-N-methyl-1,2,3,4-tetrahydro-1-naphthalenylamino |
| 5-bromo-3-(trifluoromethyl)pyrazol-1-yl | X³ | G-1 | (1R)-N-methyl-1,2,3,4-tetrahydro-1-naphthalenylamino |
| 3,5-diethylpyrazol-1-yl | X³ | G-1 | (1R)-N-methyl-1,2,3,4-tetrahydro-1-naphthalenylamino |
| 5-ethyl-3-(trifluoromethyl)pyrazol-1-yl | X³ | G-1 | (1R)-N-methyl-1,2,3,4-tetrahydro-1-naphthalenylamino |
| 3,5-bis-(trifluoromethyl)pyrazol-1-yl | X³ | G-1 | (1R)-N-methyl-1,2,3,4-tetrahydro-1-naphthalenylamino |
| 3-methyl-5-(trifluoromethyl)pyrazol-1-yl | X³ | G-1 | (1R)-N-methyl-1,2,3,4-tetrahydro-1-naphthalenylamino |
| 3-chloro-5-(trifluoromethyl)pyrazol-1-yl | X³ | G-1 | (1R)-N-methyl-1,2,3,4-tetrahydro-1-naphthalenylamino |
| 2,5-dichlorophenyl | X³ | G-1 | (1R)-N-methyl-1-indanylamino |
| 2-chloro-5-(trifluoromethyl)phenyl | X³ | G-1 | (1R)-N-methyl-1-indanylamino |
| 2,5-dimethylphenyl | X³ | G-1 | (1R)-N-methyl-1-indanylamino |
| 2-methyl-5-(trifluoromethyl)phenyl | X³ | G-1 | (1R)-N-methyl-1-indanylamino |
| 3,5-dimethylpyrazol-1-yl | X³ | G-1 | (1R)-N-methyl-1-indanylamino |

TABLE 5-continued

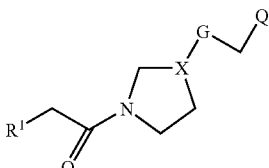

| R¹ | X* | G** | Q |
|---|---|---|---|
| 5-methyl-3-(trifluoromethyl)pyrazol-1-yl | X³ | G-1 | (1R)-N-methyl-1-indanylamino |
| 3,5-dichloropyrazol-1-yl | X³ | G-1 | (1R)-N-methyl-1-indanylamino |
| 5-chloro-3-(trifluoromethyl)pyrazol-1-yl | X³ | G-1 | (1R)-N-methyl-1-indanylamino |
| 3,5-dibromopyrazol-1-yl | X³ | G-1 | (1R)-N-methyl-1-indanylamino |
| 5-bromo-3-(trifluoromethyl)pyrazol-1-yl | X³ | G-1 | (1R)-N-methyl-1-indanylamino |
| 3,5-diethylpyrazol-1-yl | X³ | G-1 | (1R)-N-methyl-1-indanylamino |
| 5-ethyl-3-(trifluoromethyl)pyrazol-1-yl | X³ | G-1 | (1R)-N-methyl-1-indanylamino |
| 3,5-bis-(trifluoromethyl)pyrazol-1-yl | X³ | G-1 | (1R)-N-methyl-1-indanylamino |
| 3-methyl-5-(trifluoromethyl)pyrazol-1-yl | X³ | G-1 | (1R)-N-methyl-1-indanylamino |
| 3-chloro-5-(trifluoromethyl)pyrazol-1-yl | X³ | G-1 | (1R)-N-methyl-1-indanylamino |
| 2,5-dichlorophenyl | X³ | G-2 | (1R)-N-methyl-1-phenylpropylamino |
| 2-chloro-5-(trifluoromethyl)phenyl | X³ | G-2 | (1R)-N-methyl-1-phenylpropylamino |
| 2,5-dimethylphenyl | X³ | G-2 | (1R)-N-methyl-1-phenylpropylamino |
| 2-methyl-5-(trifluoromethyl)phenyl | X³ | G-2 | (1R)-N-methyl-1-phenylpropylamino |
| 3,5-dimethylpyrazol-1-yl | X³ | G-2 | (1R)-N-methyl-1-phenylpropylamino |
| 5-methyl-3-(trifluoromethyl)pyrazol-1-yl | X³ | G-2 | (1R)-N-methyl-1-phenylpropylamino |
| 3,5-dichloropyrazol-1-yl | X³ | G-2 | (1R)-N-methyl-1-phenylpropylamino |
| 5-chloro-3-(trifluoromethyl)pyrazol-1-yl | X³ | G-2 | (1R)-N-methyl-1-phenylpropylamino |
| 3,5-dibromopyrazol-1-yl | X³ | G-2 | (1R)-N-methyl-1-phenylpropylamino |
| 5-bromo-3-(trifluoromethyl)pyrazol-1-yl | X³ | G-2 | (1R)-N-methyl-1-phenylpropylamino |
| 3,5-diethylpyrazol-1-yl | X³ | G-2 | (1R)-N-methyl-1-phenylpropylamino |
| 5-ethyl-3-(trifluoromethyl)pyrazol-1-yl | X³ | G-2 | (1R)-N-methyl-1-phenylpropylamino |
| 3,5-bis-(trifluoromethyl)pyrazol-1-yl | X³ | G-2 | (1R)-N-methyl-1-phenylpropylamino |
| 3-methyl-5-(trifluoromethyl)pyrazol-1-yl | X³ | G-2 | (1R)-N-methyl-1-phenylpropylamino |
| 3-chloro-5-(trifluoromethyl)pyrazol-1-yl | X³ | G-2 | (1R)-N-methyl-1-phenylpropylamino |
| 2,5-dichlorophenyl | X³ | G-2 | (1R)-N-methyl-1,2,3,4-tetrahydro-1-naphthalenylamino |
| 2-chloro-5-(trifluoromethyl)phenyl | X³ | G-2 | (1R)-N-methyl-1,2,3,4-tetrahydro-1-naphthalenylamino |
| 2,5-dimethylphenyl | X³ | G-2 | (1R)-N-methyl-1,2,3,4-tetrahydro-1-naphthalenylamino |
| 2-methyl-5-(trifluoromethyl)phenyl | X³ | G-2 | (1R)-N-methyl-1,2,3,4-tetrahydro-1-naphthalenylamino |
| 3,5-dimethylpyrazol-1-yl | X³ | G-2 | (1R)-N-methyl-1,2,3,4-tetrahydro-1-naphthalenylamino |
| 5-methyl-3-(trifluoromethyl)pyrazol-1-yl | X³ | G-2 | (1R)-N-methyl-1,2,3,4-tetrahydro-1-naphthalenylamino |
| 3,5-dichloropyrazol-1-yl | X³ | G-2 | (1R)-N-methyl-1,2,3,4-tetrahydro-1-naphthalenylamino |
| 5-chloro-3-(trifluoromethyl)pyrazol-1-yl | X³ | G-2 | (1R)-N-methyl-1,2,3,4-tetrahydro-1-naphthalenylamino |
| 3,5-dibromopyrazol-1-yl | X³ | G-2 | (1R)-N-methyl-1,2,3,4-tetrahydro-1-naphthalenylamino |
| 5-bromo-3-(trifluoromethyl)pyrazol-1-yl | X³ | G-2 | (1R)-N-methyl-1,2,3,4-tetrahydro-1-naphthalenylamino |
| 3,5-diethylpyrazol-1-yl | X³ | G-2 | (1R)-N-methyl-1,2,3,4-tetrahydro-1-naphthalenylamino |
| 5-ethyl-3-(trifluoromethyl)pyrazol-1-yl | X³ | G-2 | (1R)-N-methyl-1,2,3,4-tetrahydro-1-naphthalenylamino |
| 3,5-bis-(trifluoromethyl)pyrazol-1-yl | X³ | G-2 | (1R)-N-methyl-1,2,3,4-tetrahydro-1-naphthalenylamino |
| 3-methyl-5-(trifluoromethyl)pyrazol-1-yl | X³ | G-2 | (1R)-N-methyl-1,2,3,4-tetrahydro-1-naphthalenylamino |
| 3-chloro-5-(trifluoromethyl)pyrazol-1-yl | X³ | G-2 | (1R)-N-methyl-1,2,3,4-tetrahydro-1-naphthalenylamino |
| 2,5-dichlorophenyl | X³ | G-2 | (1R)-N-methyl-1-indanylamino |
| 2-chloro-5-(trifluoromethyl)phenyl | X³ | G-2 | (1R)-N-methyl-1-indanylamino |
| 2,5-dimethylphenyl | X³ | G-2 | (1R)-N-methyl-1-indanylamino |
| 2-methyl-5-(trifluoromethyl)phenyl | X³ | G-2 | (1R)-N-methyl-1-indanylamino |
| 3,5-dimethylpyrazol-1-yl | X³ | G-2 | (1R)-N-methyl-1-indanylamino |
| 5-methyl-3-(trifluoromethyl)pyrazol-1-yl | X³ | G-2 | (1R)-N-methyl-1-indanylamino |
| 3,5-dichloropyrazol-1-yl | X³ | G-2 | (1R)-N-methyl-1-indanylamino |
| 5-chloro-3-(trifluoromethyl)pyrazol-1-yl | X³ | G-2 | (1R)-N-methyl-1-indanylamino |
| 3,5-dibromopyrazol-1-yl | X³ | G-2 | (1R)-N-methyl-1-indanylamino |
| 5-bromo-3-(trifluoromethyl)pyrazol-1-yl | X³ | G-2 | (1R)-N-methyl-1-indanylamino |
| 3,5-diethylpyrazol-1-yl | X³ | G-2 | (1R)-N-methyl-1-indanylamino |
| 5-ethyl-3-(trifluoromethyl)pyrazol-1-yl | X³ | G-2 | (1R)-N-methyl-1-indanylamino |
| 3,5-bis-(trifluoromethyl)pyrazol-1-yl | X³ | G-2 | (1R)-N-methyl-1-indanylamino |
| 3-methyl-5-(trifluoromethyl)pyrazol-1-yl | X³ | G-2 | (1R)-N-methyl-1-indanylamino |

TABLE 5-continued

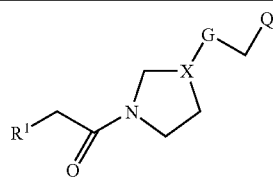

| R¹ | X* | G** | Q |
|---|---|---|---|
| 3-chloro-5-(trifluoromethyl)pyrazol-1-yl | X³ | G-2 | (1R)-N-methyl-1-indanylamino |
| 5-methyl-3-(trifluoromethyl)pyrazol-1-yl | X⁴ | G-1 | (1R)-N-methyl-1,2,3,4-tetrahydro-1-naphthalenylamino |
| 5-methyl-3-(trifluoromethyl)pyrazol-1-yl | X⁵ | G-1 | (1R)-N-methyl-1,2,3,4-tetrahydro-1-naphthalenylamino |
| 5-methyl-3-(trifluoromethyl)pyrazol-1-yl | X⁶ | G-1 | (1R)-N-methyl-1,2,3,4-tetrahydro-1-naphthalenylamino |
| 5-methyl-3-(trifluoromethyl)pyrazol-1-yl | X⁷ | G-1 | (1R)-N-methyl-1,2,3,4-tetrahydro-1-naphthalenylamino |
| 5-methyl-3-(trifluoromethyl)pyrazol-1-yl | X⁸ | G-1 | (1R)-N-methyl-1,2,3,4-tetrahydro-1-naphthalenylamino |
| 5-methyl-3-(trifluoromethyl)pyrazol-1-yl | X⁴ | G-2 | (1R)-N-methyl-1,2,3,4-tetrahydro-1-naphthalenylamino |
| 5-methyl-3-(trifluoromethyl)pyrazol-1-yl | X⁵ | G-2 | (1R)-N-methyl-1,2,3,4-tetrahydro-1-naphthalenylamino |
| 5-methyl-3-(trifluoromethyl)pyrazol-1-yl | X⁶ | G-2 | (1R)-N-methyl-1,2,3,4-tetrahydro-1-naphthalenylamino |
| 5-methyl-3-(trifluoromethyl)pyrazol-1-yl | X⁷ | G-2 | (1R)-N-methyl-1,2,3,4-tetrahydro-1-naphthalenylamino |
| 5-methyl-3-(trifluoromethyl)pyrazol-1-yl | X⁸ | G-2 | (1R)-N-methyl-1,2,3,4-tetrahydro-1-naphthalenylamino |

Notes:
*n is 0.
**$R^{3a}$ is H.

Formulation/Utility

A compound of this invention will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto vegetable seeds as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof, amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents,* annual American and International Editions published by McCutcheon's Division, The Manufacturing Confectioner Publishing Co.; Sisely and Wood, *Encyclopedia of Surface Active Agents,* Chemical Publ. Co., Inc., New York, 1964; and A. S. Davidson and B. Milwidsky, *Synthetic Detergents,* Seventh Edition, John Wiley and Sons, New York, 1987.

Compositions of this invention may also contain formulation auxiliaries and additives, known to those skilled in the art as formulation aids. Such formulation auxiliaries and additives may control: pH (buffers), foaming during processing (antifoams such polyorganosiloxanes (e.g., Rhodorsil® 416)), sedimentation of active ingredients (suspending agents), viscosity (thixotropic thickeners), in-container microbial growth (antimicrobials), product freezing (antifreezes), color (dyes/pigment dispersions (e.g., Prolzed® Colorant Red)), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials,* annual International and North American editions published by McCutcheon's Division, The Manufacturing Confectioner Publishing Co.; and PCT Publication WO 03/024222.

Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and, usually, grinding as in a hammer mill or fluid-energy mill. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Table A.

Example A

| High Strength Concentrate | |
|---|---|
| Compound 1 | 98.5% |
| silica aerogel | 0.5% |
| synthetic amorphous fine silica | 1.0%. |

Example B

| Wettable Powder | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

| Granule | |
|---|---|
| Compound 4 | 10.0% |
| attapulgite granules (low volatile matter, 0.71/0.30 mm; U.S.S. No. 25-50 sieves) | 90.0%. |

Example D

| Aqueous Suspension | |
|---|---|
| Compound 3 | 25.0% |
| hydrated attapulgite | 3.0% |
| crude calcium ligninsulfonate | 10.0% |
| sodium dihydrogen phosphate | 0.5% |
| water | 61.5%. |

Example E

| Extruded Pellet | |
|---|---|
| Compound 6 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example F

| Microemulsion | |
|---|---|
| Compound 4 | 1.0% |
| triacetine | 30.0% |
| $C_8$-$C_{10}$ alkylpolyglycoside | 30.0% |
| glyceryl monooleate | 19.0% |
| water | 20.0%. |

Example G

| Emulsifiable Concentrate | |
|---|---|
| Compound 1 | 10.0% |
| $C_8$-$C_{10}$ fatty acid methyl ester | 70.0% |
| polyoxyethylene sorbitol hexoleate | 20.0%. |

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici repentis*, *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita*, *Puccinia striiformis*, *Puccinia hordei*, *Puccinia graminis* and *Puccinia arachidis*), *Hemileia vastatrix* and *Phakopsora pachyrhizi*; other pathogens including *Rhizoctonia* spp. (such as *Rhizoctonia solani*); *Fusarium* diseases such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; and other genera and species closely related to these pathogens. In addition to their fungicidal activity, the compositions or combinations also have activity against bacteria such as *Erwinia amylovora*, *Xanthomonas campestris*, *Pseudomonas syringae*, and other related species. Of note is control provided of disease caused by the Ascomycete and Oomycete classes. Of particular note is control provided of disease caused by the Oomycete class.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, acetamiprid, amidoflumet (S-1955), avermectin, azadirachtin, azinphos-methyl, bifenthrin, bifenazate, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, enestroburin (SYP-Z071), esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, rynaxypyr, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar-5-methyl, aldimorph, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, Bordeaux mixture (tribasic copper sulfate), boscalid, bromuconazole, bupirimate, captafol, captan, carbendazim, carboxin, carpropamid, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, folpet, fosetyl-aluminum, fuberidazole, furalaxyl, furametpyr, guazatine, hexaconazole, hymexazol, imazalil, imibenconazole, iminoctadine albesilate, iminoctadine triacetate, iodocarb, ipconazole, iprobenfos, iprodione, iprovalicarb, isoprothiolane, isotianil, kasugamycin, kresoxim-methyl, mancozeb, mandipropamid, maneb, mepanipyrim, mepronil, meptyldinocap, metalaxyl, metalaxyl-M, metconazole, methasulfocarb, metiram, metominostrobin, metrafenone, myclobutanil, naftifine, neo-asozin (ferric methanearsonate), nuarimol, octhilinone, ofurace, orysastrobin, oxadixyl, oxolinic acid, oxpoconazole, oxycarboxin, oxytetracycline, pefurazoate, penconazole, pencycuron, penthiopyrad, phosphorous acid and salts, phthalide, picoxystrobin, piperalin, polyoxin, probenazole, prochloraz, procymidone, propamocarb, propamocarb-hydrochloride, propiconazole, propineb, proquinazid, prothiocarb, prothioconazole, pyrazophos, pyraclostrobin, pyribencarb, pyributicarb, pyrifenox, pyrimethanil, pyrrolnitrin, pyroquilon, quinomethionate, quinoxyfen, quintozene, silthiofam, simeconazole, spiroxamine, streptomycin, sulfur, tebuconazole, tecloftalam, tecnazene, terbinafine, tetraconazole, thiabendazole, thifluzamide, thiophanate, thiophanate-methyl, thiram, tiadinil, tolclofos-methyl, tolyfluanid, triadimefon, triadimenol, triazoxide, tricyclazole, tridemorph, trifloxystrobin, triflumizole, triforine, triticonazole, uniconazole, validamycin, valiphenal, vinclozolin, zineb, ziram, zoxamide, N-[2-(1,3-dimethylbutyl)phenyl]-5-fluoro-1,3-dimethyl-1H-pyrazol-4-carboxamide, N-[2-(1S,2R)-[1,1'-bicyclopropyl]-2-ylphenyl]-3-(difluoromethyl)-1-methyl-1H-pyrazole-4-carboxamide, α-[methoxyimino]-N-methyl-2-[[[1-[3-(trifluoromethyl)-phenyl]-ethoxy]imino]methyl]benzeneacetamide, 2-[[[3-(2,6-dichlorophenyl)-1-methyl-2-propen-1-ylidene]amino]oxy]methyl]-α-(methoxyimino)-N-methylbenzeneacetamide, N-[2-[4-[[3-(4-chlorophenyl)-2-propyn-1-yl]oxy]-3-methoxy phenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-[[2-fluoro-5-(trifluoromethyl)phenyl]thio]-2-[3-(2-methoxyphenyl)-2-thiazolidinylidene]acetonitrile, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]-methyl]propyl]carbamate, 5-chloro-6-(2,4,6-trifluorophenyl)-7-(4-methylpiperidin-1-yl)[1,2,4]triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3 difluorophenyl]methylene]benzeneacetamide, N'-[4-[4-chloro-3-(trifluoromethyl)phenoxy]-2,5-dimethylphenyl]-N-ethyl-N-methylmethanimidamide, and 1-[(2-propenylthio)carbonyl]-2-(1-methylethyl)-4-(2-methylphenyl)-5-amino-1H-pyrazol-3-one; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai, Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:100 and about 3000:1. Of note are weight ratios between about 1:30 and about 300:1 (for example ratios between about 1:1 and about 30:1). It will be evident that including these additional components may expand the spectrum of diseases controlled beyond the spectrum controlled by the compound of Formula 1 alone.

In one mixture embodiment, granules of a solid composition comprising a compound of Formula 1 is mixed with granules of a solid composition comprising another agricultural protectant. These granule mixtures can be in accordance with the general granule mixture disclosure of PCT Patent Publication WO 94/24861 or more preferably the homogenous granule mixture teaching of U.S. Pat. No. 6,022,552.

Of note are combinations (e.g., in the form of compositions) of a compound of Formula 1 with at least one other fungicide. Of particular note are such combinations where the other fungicide has different site of action from the compound of Formula 1. In certain instances, combinations with other fungicides having a similar spectrum of control but a different site of action will be particularly advantageous for resistance management. Of particular note are compositions which in addition to compound of Formula 1 include at least one compound selected from the group consisting of (1) alkylenebis (dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Pyrimidinone fungicides (group (4)) include compounds of Formula A1

A1

[Chemical structure of Formula A1 showing a pyrimidinone ring with substituents $R^{11}$, $R^{12}$, $R^{13}$, $R^{14}$, and M]

wherein M forms a fused phenyl, thiophene or pyridine ring; $R^{11}$ is $C_1$-$C_6$ alkyl; $R^{12}$ is $C_1$-$C_6$ alkyl or $C_1$-$C_6$ alkoxy; $R^{13}$ is halogen; and $R^{14}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo-3-propyl-2-propyloxy-4(3H)-quinazolinone, 6,8-diiodo-3-propyl-2-propyloxy-4(3H)-quinazolinone, 6-iodo-3-propyl-2-propyloxy-4(3H)-quinazolinone (proquinazid), 6-chloro-2-propoxy-3-propylthieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propylthieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of note are these methods where plant diseases caused by Oomycete fungal plant pathogens are controlled.

The following TESTS demonstrate the control efficacy of compounds of this invention on specific pathogens. The pathogen control protection afforded by the compounds is not limited, however, to these species. See Index Table A for compound descriptions. "Cmpd" is an abbreviation for Compound. (R) or (S) denotes the absolute chirality of the asymmetric carbon center. The abbreviation "Ex." stands for "Example" and is followed by a number indicating in which example the compound is prepared. Index Table A lists the molecular weight of the highest isotopic abundance parent ion (M+1) formed by addition of H+ (molecular weight of 1) to the molecule, observed by mass spectrometry using atmospheric pressure chemical ionization (AP+).

INDEX TABLE A

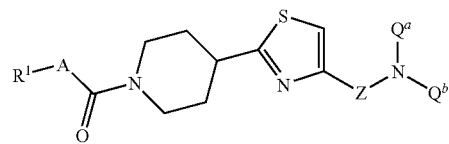

| Cmpd | $R^1$ | A | Z | $Q^a$ | $Q^b$ | AP+ (M + 1) |
|---|---|---|---|---|---|---|
| 1 (Ex. 1) | 3-trifluoromethyl-5-methylpyrazol-1-yl | $CH_2$ | $CH_2$ | $CH_3$ | (1R)-1,2,3,4-tetrahydro-1-naphthalenyl | 532 |
| 2 | 3-trifluoromethyl-5-methylpyrazol-1-yl | $CH_2$ | $CH_2$ | H | (1R)-1,2,3,4-tetrahydro-1-naphthalenyl | 518 |

INDEX TABLE A-continued

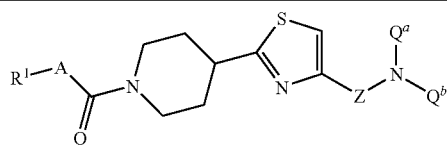

| Cmpd | R¹ | A | Z | Q$^a$ | Q$^b$ | AP⁺ (M + 1) |
|---|---|---|---|---|---|---|
| 3 | 3-trifluoromethyl-5-methylpyrazol-1-yl | CH$_2$ | CH$_2$ | C(=O)CH$_3$ | (1R)-1,2,3,4-tetrahydro-1-naphthalenyl | 560 |
| 4 | 3-trifluoromethyl-5-methylpyrazol-1-yl | CH$_2$ | CH$_2$ | CHO | (1R)-1,2,3,4-tetrahydro-1-naphthalenyl | 546 |
| 5 | 3-trifluoromethyl-5-methylpyrazol-1-yl | CH$_2$CH$_2$ | C=O | CH$_3$ | (1R)-1,2,3,4-tetrahydro-1-naphthalenyl | 560 |
| 6 (Ex. 2) | 3-trifluoromethyl-5-methylpyrazol-1-yl | CHCO$_2$Et | C=O | CH$_3$ | 1,2,3,4-tetrahydro-1-naphthalenyl | 618 |

Biological Examples of the Invention

General protocol for preparing test suspensions for Tests A-C: The test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in tests A-C. Spraying a 200 ppm test suspension to the point of run-off on the test plants was the equivalent of a rate of 500 g/ha.

Test A

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings, which were then moved to a growth chamber at 20° C. for 5 days, after which time the grape seedlings were placed back into a saturated atmosphere at 20° C. for 24 h. Upon removal, visual disease ratings were made.

Test B

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test C

Tomato seedlings were inoculated with a spore suspension of *Phytophthora infestans* (the causal agent of tomato late blight) and incubated in a saturated atmosphere at 20° C. for 17 h. After a short drying period, the test suspension was sprayed to the point of run-off on the tomato seedlings, which were then moved to a growth chamber at 20° C. for 4 days, after which time visual disease ratings were made.

In addition to Tests A-C, the compounds were also sprayed on tomato plants inoculated with *Botrytis cinerea* 24 h after treatment and three separate sets of wheat plants inoculated with *Erysiphe graminis* f. sp. *tritici*, *Puccinia recondita* or *Septoria nodorum* 24 h after treatment. Test compounds did not show noticeable activity against these additional pathogens under the test conditions at the application rates tested.

Results for Tests A-C are given in Table A. In the table, a rating of 100 indicates 100% disease control and a rating of 0 indicates no disease control (relative to the controls). A dash (-) indicates no test results.

TABLE A

| Cmpd No | Test A | Test B | Test C |
|---|---|---|---|
| 1 | 72 | 100 | 99 |
| 2 | 28 | 100 | 93 |
| 3 | 55 | 85 | 53 |
| 4 | 0 | 87 | 26 |
| 5* | 17 | 57 | 0 |
| 6* | 72 | 17 | 0 |

*indicates compound tested at 40 ppm.

What is claimed is:

1. A compound selected from Formula 1, an N-oxide and salt thereof,

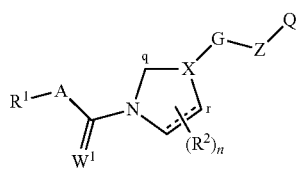

wherein

R¹ is an optionally substituted phenyl or 5- or 6-membered heteroaromatic ring;

A is NR$^{18}$ or C$_1$-C$_3$ alkylene optionally substituted with 1-3 substituents independently selected from R$^{17}$;

W¹ is O or S;

X is a radical selected from

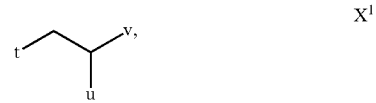

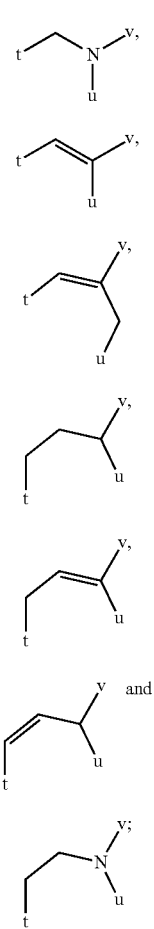

wherein the bond of X which is identified with "t" is connected to the carbon atom identified with "q" of Formula 1, the bond which is identified with "u" is connected to the carbon atom identified with "r" of Formula 1, and the bond which is identified with "v" is connected to G;

each $R^2$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy;

n is 0, 1 or 2; or two $R^2$ are taken together as $C_1$-$C_3$ alkylene or $C_2$-$C_3$ alkenylene to form a bridged bicyclic ring system; or two $R^2$ attached to adjacent ring carbon atoms joined by a double bond are taken together as —CH=CH—CH=CH— optionally substituted with 1-3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

G is an optionally substituted 5-membered heteroaromatic ring or 5-membered saturated or partially saturated heterocyclic ring;

Z is C=$W^2$ or $C_1$-$C_3$ alkylene optionally substituted with 1-3 substituents independently selected from $R^{19}$;

$W^2$ is O or S;

Q is —N$Q^aQ^b$;

$Q^a$ is H, —CHO, $C_1$-$C_3$ alkyl, $C_2$-$C_3$ alkenyl, $C_2$-$C_3$ alkynyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_3$ haloalkyl, $C_2$-$C_3$ haloalkenyl, cyano, hydroxy, $C_1$-$C_3$ alkoxy, $C_2$-$C_3$ alkoxyalkyl, $C_1$-$C_3$ hydroxyalkyl, $C_2$-$C_3$ alkylcarbonyl, $C_2$-$C_3$ alkoxycarbonyl, $C_2$-$C_3$ alkylaminocarbonyl or $C_3$-$C_5$ dialkylaminocarbonyl;

$Q^b$ is an optionally substituted 8- to 11-membered saturated or partially saturated bicyclic ring system or an optionally substituted 10- to 15-membered partially saturated tricyclic ring system, each ring system optionally containing 1 to 3 heteroatoms selected from up to 1 O, up to 1 S and up to 3 N, and optionally including 1-3 ring members selected from the group consisting of C(=O), C(=S), S(O), or S(O)$_2$; or $Q^b$ is C$R^5R^6R^{15}$; or $Q^a$ and $Q^b$ are taken together with the nitrogen atom to which they are bonded to form an optionally substituted 5- to 7-membered saturated or partially saturated heterocyclic ring;

$R^5$ is H, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, cyano, nitro, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

$R^6$ is an optionally substituted phenyl, benzyl, naphthalenyl, $C_3$-$C_6$ cycloalkyl, $C_3$-$C_6$ cycloalkenyl or 5- or 6-membered heteroaromatic ring; and $R^{15}$ is H, $C_1$-$C_4$ alkyl, $C_2$-$C_4$ alkenyl, $C_2$-$C_4$ alkynyl, $C_3$-$C_4$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_4$ haloalkyl, $C_2$-$C_4$ haloalkenyl, $C_2$-$C_4$ haloalkynyl, $C_3$-$C_4$ halocycloalkyl or $C_2$-$C_4$ alkoxyalkyl; or $Q^a$ and $R^5$ are taken together with the atoms connecting them to form an optionally substituted 5- to 7-membered ring containing as ring members 2 to 7 carbon atoms and optionally 1 to 3 heteroatoms selected from up to 1 O, up to 1 S and up to 2 N; or $Q^a$ and $R^6$ are taken together with the atoms connecting them to form an optionally substituted 5- to 7-membered ring containing as ring members 2 to 7 carbon atoms and optionally 1 to 3 heteroatoms selected from up to 1 O, up to 1 S and up to 2 N; or $R^5$ and $R^{15}$ are taken together with the carbon atom to which they are bonded to form an optionally substituted 5- to 7-membered ring containing as ring members 2 to 7 carbon atoms and, optionally 1 to 3 heteroatoms selected from up to 1 O, up to 1 S and up to 1 N; or $R^5$ and $R^6$ are taken together with the carbon atom to which they are bonded to form an optionally substituted 5- to 7-membered ring containing as ring members 2 to 7 carbon atoms and, optionally 1 to 3 heteroatoms selected from up to 1 O, up to 1 S and up to 1 N;

$R^{17}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

$R^{18}$ is H, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkoxyalkoxy, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl; and $R^{19}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl;

provided that:

(a) when X is $X^2$, $X^3$, $X^4$, $X^6$ or $X^8$, then G is not linked to X via a heteroatom of the G ring; and (b) when Z is C=$W^2$, then A is other than NH or $CH_2$.

2. A compound of claim 1 wherein $R^1$ is a phenyl or 5- or 6-membered heteroaromatic ring, optionally substituted with 1 to 2 substituents independently selected from $R^4$;

each $R^4$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;

each $R^3$ is independently $C_1$-$C_3$ alkyl, $C_1$-$C_3$ haloalkyl or halogen;

$R^{11}$ is $C_1$-$C_3$ alkyl;

Q is a radical selected from

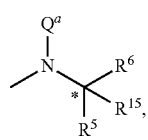

Q-1

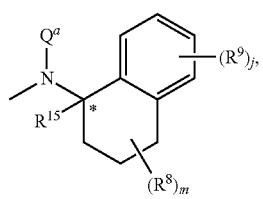

Q-2

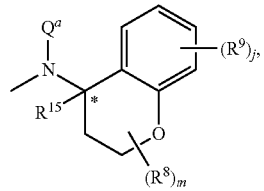

Q-3

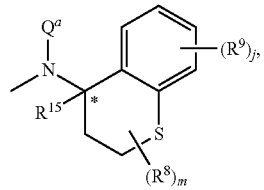

Q-4

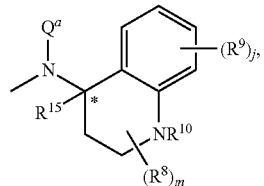

Q-5

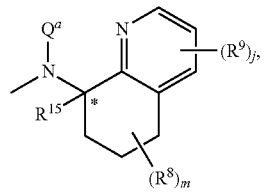

Q-6

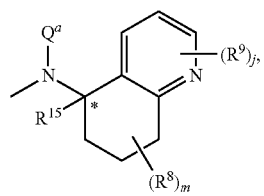

Q-7

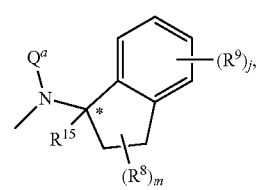

Q-8

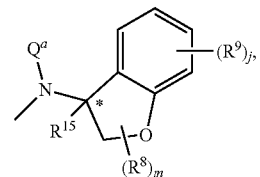

Q-9

Q-10

-continued
Q-11
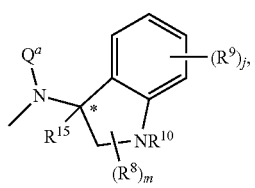
Q-12
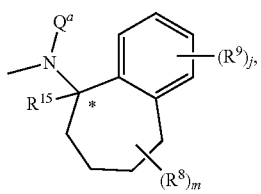
Q-13
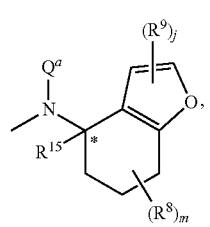
Q-14
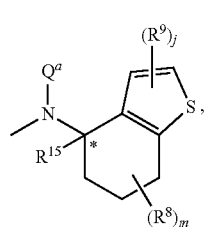
Q-15
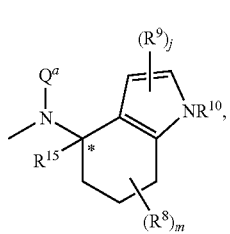
Q-16
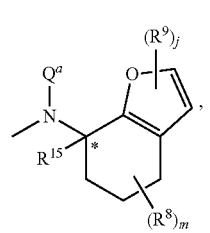
Q-17
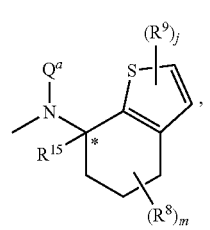
-continued
Q-18
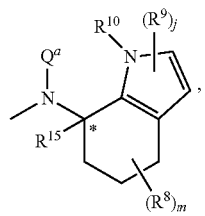
Q-19
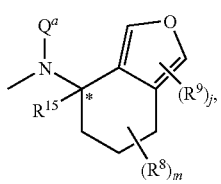
Q-20
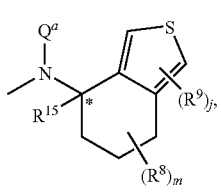
Q-21
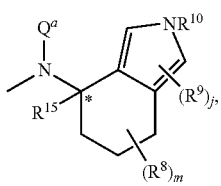
Q-22
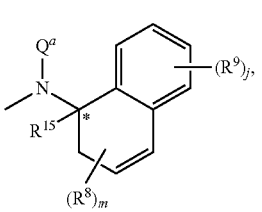
Q-23
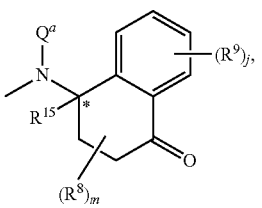
Q-24
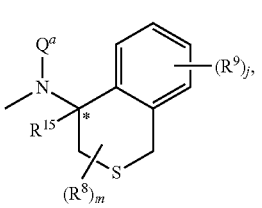
Q-25

Q-26 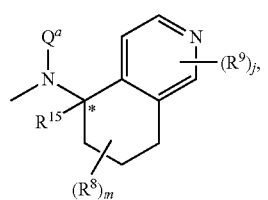
Q-27 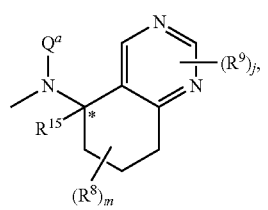
Q-28 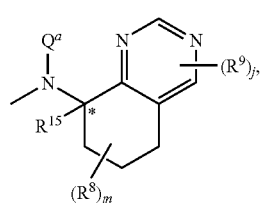
Q-29 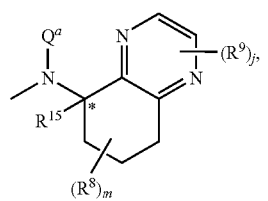
Q-30 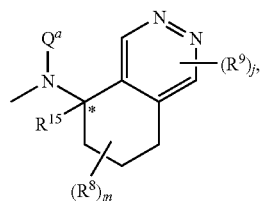
Q-31 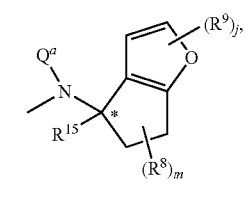
Q-32 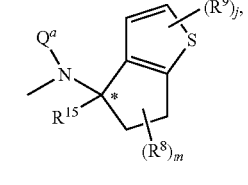
Q-33 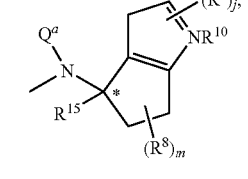
Q-34 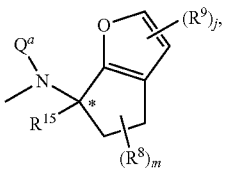
Q-35 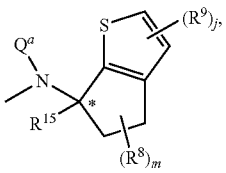
Q-36 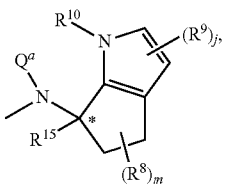
Q-37 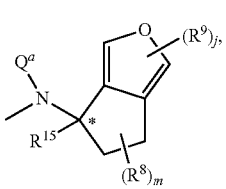
Q-38 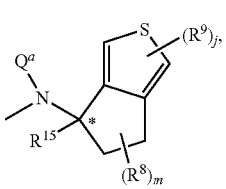
Q-39 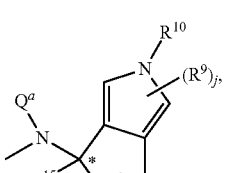
Q-40 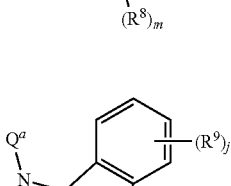
Q-41 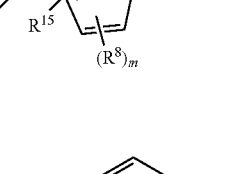

-continued
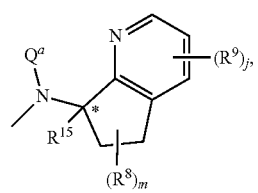 Q-42
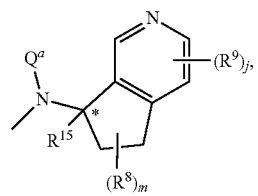 Q-43
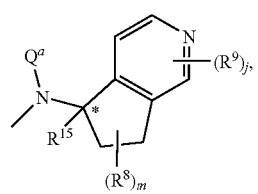 Q-44
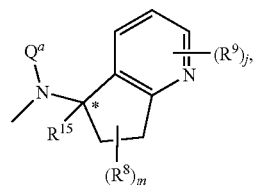 Q-45
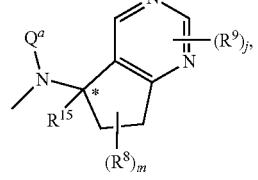 Q-46
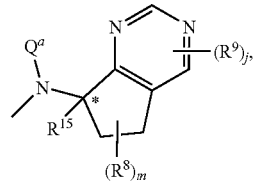 Q-47
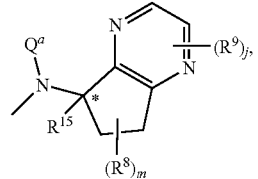 Q-48
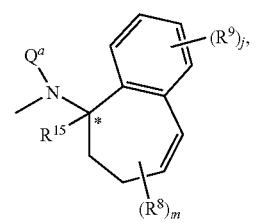 Q-49
-continued
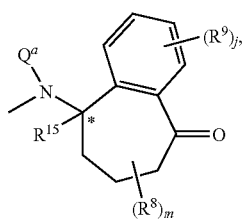 Q-50
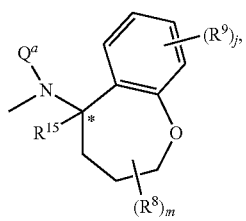 Q-51
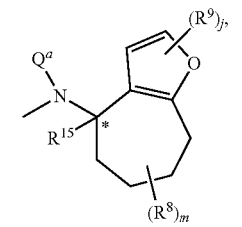 Q-52
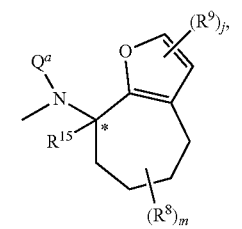 Q-53
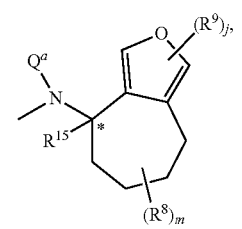 Q-54
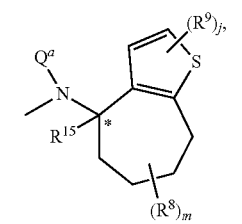 Q-55
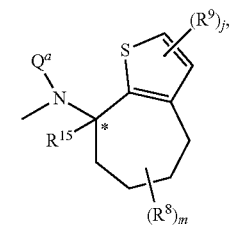 Q-56

-continued
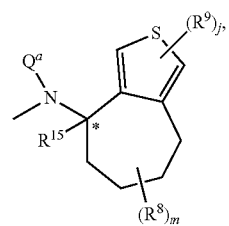 Q-57
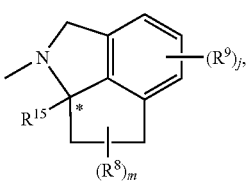 Q-58
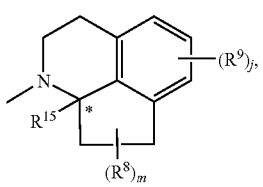 Q-59
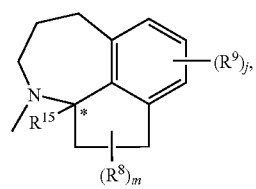 Q-60
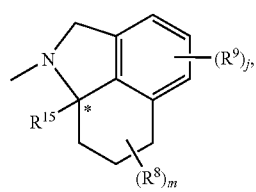 Q-61
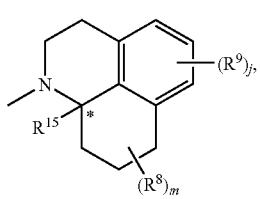 Q-62
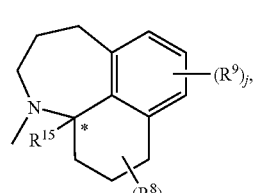 Q-63
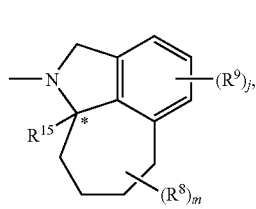 Q-64
-continued
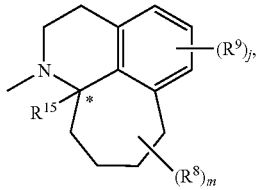 Q-65
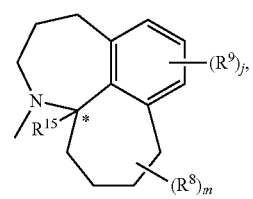 Q-66
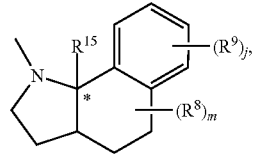 Q-67
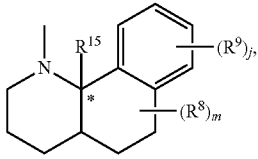 Q-68
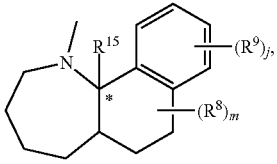 Q-69
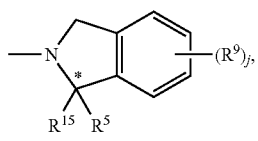 Q-70
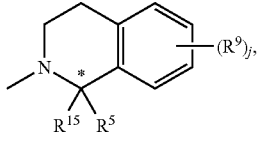 Q-71
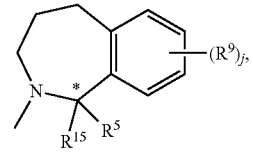 Q-72
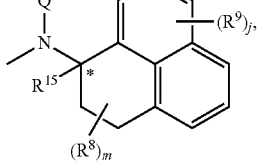 Q-73

Q-74 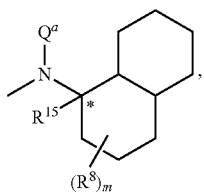

Q-75 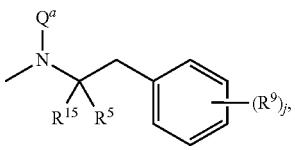

Q-76 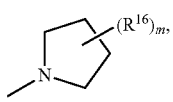

Q-77 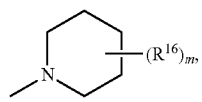

Q-78 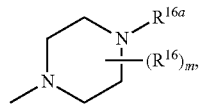

Q-79 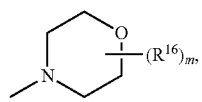

Q-80 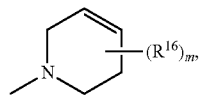

Q-81 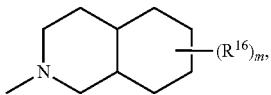

Q-82 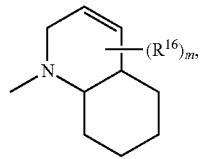

Q-83 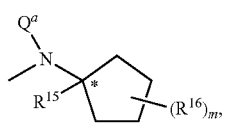

Q-84 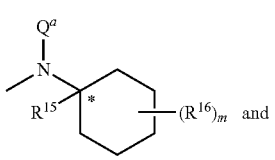 and

Q-85 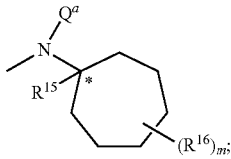

wherein carbon atom identified with the asterisk (*) contains a stereocenter; and for Q-2 through Q-75, each $R^8$ is independently attached to the carbon atoms of the nonaromatic carbocyclic ring or heterocyclic ring of the Q group, and each $R^9$ is independently attached to the carbon atoms of phenyl or heteroaromatic ring of the Q group;

each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_6$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_4$ alkoxycarbonyl, $C_2$-$C_4$ alkylcarbonyloxy, $C_2$-$C_4$ alkylcarbonylthio, $C_2$-$C_4$ alkylaminocarbonyl, $C_2$-$C_4$ alkylaminocarbonyloxy, $C_3$-$C_6$ dialkylaminocarbonyl or $C_3$-$C_6$ trialkylsilyl;

each $R^9$ is independently $C_1$-$C_6$ alkyl, $C_2$-$C_6$ alkenyl, $C_3$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

$R^{10}$ is H or $C_1$-$C_3$ alkyl;

m is 0, 1 or 2;

j is 0, 1 or 2;

each $R^{16}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or a phenyl or benzyl ring, optionally substituted with up to 3 substituents selected from $R^{13}$; or two $R^{16}$ attached to adjacent ring carbon atoms are taken together as —$(CH_2)_3$— or —$(CH_2)_4$— optionally substituted with 1-3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

$R^{16a}$ is H, $C_1$-$C_6$ alkyl, $C_3$-$C_6$ alkenyl, $C_3$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_3$-$C_6$ haloalkenyl, $C_3$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylsulfonyl, $C_1$-$C_4$ haloalkylsulfonyl, amino, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylaminocarbonyl or $C_3$-$C_8$ dialkylaminocarbonyl; or a phenyl or benzyl ring, optionally substituted with up to 3 substituents selected from $R^{13}$;

each $R^{13}$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl;

$R^6$ is a phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members;

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and $R^{12}$ is H or $C_1$-$C_3$ alkyl.

3. A compound of claim 2 wherein $R^1$ is one of U-1 through U-50;

k is 0, 1 or 2;

G is one of G-1 through G-55;

$R^{3a}$ is H, $C_1$-$C_3$ alkyl, $C_1$-$C_3$ haloalkyl or halogen;

$R^{11a}$ is H or $C_1$-$C_3$ alkyl;

$R^6$ is one of H-1 through H-46; and p is 0, 1 or 2;

provided that when U is U-4, U-11 through U-15, U-24 through U-26, U-31 and U-35, and an $R^4$ radical is attached to a nitrogen atom of the ring, said $R^4$ radical is $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, $C_3$-$C_6$ halocycloalkyl or $C_2$-$C_4$ alkoxyalkyl.

4. A compound of claim 3 wherein each $R^2$ is independently $C_1$-$C_2$ alkyl, $C_1$-$C_2$ haloalkyl, $C_1$-$C_2$ alkoxy, halogen, cyano or hydroxy;

each $R^4$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy;

X is a radical selected from $X^1$, $X^2$ and $X^3$;

$Q^a$ is H or $CH_3$;

$R^5$ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano or $C_2$-$C_4$ alkoxyalkyl;

each $R^7$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy;

each $R^8$ is independently H, $C_1$-$C_4$ alkyl, $C_2$-$C_4$ alkenyl, $C_3$-$C_4$ alkynyl, $C_3$-$C_6$ cycloalkyl, $C_1$-$C_4$ haloalkyl, $C_2$-$C_4$ haloalkenyl, $C_2$-$C_4$ haloalkynyl, $C_3$-$C_6$ halocycloalkyl, halogen, hydroxy, amino, cyano, nitro, $C_1$-$C_4$ alkoxy or $C_2$-$C_4$ alkylcarbonyloxy;

each $R^9$ is independently $C_1$-$C_3$ alkyl, cyclopropyl, $C_1$-$C_3$ haloalkyl, halocyclopropyl, halogen, hydroxy, $C_2$-$C_3$ alkylcarbonyloxy, $C_1$-$C_2$ alkoxy or $C_1$-$C_2$ haloalkoxy;

$R^{10}$ is H or methyl;

each $R^{16}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy; or a phenyl or benzyl ring, optionally substituted with up to 3 substituents selected from $R^{13}$;

$R^{16a}$ is H, $C_1$-$C_3$ alkyl, allyl, propargyl, cyclopropyl or $C_1$-$C_3$ haloalkyl; or a phenyl or benzyl ring, optionally substituted with up to 3 substituents selected from $R^{13}$;

each $R^{13}$ is independently $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, halogen, cyano, nitro, $C_1$-$C_2$ alkoxy or $C_1$-$C_2$ haloalkoxy;

$R^{15}$ is H or $CH_3$;

A is $NR^{18}$ or methylene optionally substituted with $R^{17}$;

$R^{17}$ is H, halogen, cyano, —CHO, $C_1$-$C_2$ alkyl, $C_2$-$C_3$ alkoxyalkyl, $C_2$-$C_3$ alkylcarbonyl or $C_2$-$C_3$ alkoxycarbonyl;

$R^{18}$ is H, cyano, hydroxy, —CHO, $C_1$-$C_2$ alkyl, $C_2$-$C_3$ alkoxyalkyl, $C_2$-$C_3$ alkylcarbonyl or $C_2$-$C_3$ alkoxycarbonyl;

Z is $C=W^2$ or methylene optionally substituted with $R^{19}$; and $R^{19}$ is H, halogen, cyano, $C_1$-$C_2$ alkyl or $C_1$-$C_2$ haloalkyl.

5. A compound of claim 4 wherein $R^1$ is one of U-1 through U-3, U-13, U-20, U-22, U-23, U-37 through U-39 or U-50; and each $R^4$ is independently halogen, $C_1$-$C_3$ alkyl, $C_1$-$C_3$ haloalkyl, $C_1$-$C_2$ alkoxy or $C_1$-$C_2$ haloalkoxy.

6. A compound of claim 4 wherein

G is G-1, G-2, G-7, G-8, G-14, G-15, G-23, G-24, G-26, G-27, G-36 through G-38, G-49 or G-50;

$R^{3a}$ is H, $CH_3$, Cl or Br;

$R^{17}$ is H, $C_1$-$C_2$ alkyl, $C_2$-$C_3$ alkylcarbonyl or $C_2$-$C_3$ alkoxycarbonyl;

$R^{18}$ is H, —CHO, $C_1$-$C_2$ alkyl, $C_2$-$C_3$ alkylcarbonyl or $C_2$-$C_3$ alkoxycarbonyl; and $R^{19}$ is H, $C_1$-$C_2$ alkyl or $C_1$-$C_2$ haloalkyl.

7. A compound of claim 6 wherein

G is unsubstituted.

8. A compound of claim 4 wherein

Q is Q-1, Q-2, Q-3, Q-4, Q-8, Q-9, Q-10, Q-12, Q-14, Q-22, Q-23, Q-24, Q-40, Q-41, Q-59, Q-62, Q-74 or Q-84;

$R^5$ is $C_1$-$C_4$ alkyl, $C_2$-$C_4$ alkenyl, $C_2$-$C_4$ alkynyl, $C_3$-$C_4$ cycloalkyl, $C_1$-$C_4$ haloalkyl, $C_2$-$C_4$ haloalkenyl, $C_2$-$C_4$ haloalkynyl, $C_3$-$C_4$ halocycloalkyl, cyano or $C_2$-$C_4$ alkoxyalkyl;

$R^6$ is H-1, H-20, H-32, H-45 or H-46;

each $R^7$ is independently halogen, $C_1$-$C_3$ alkyl, $C_1$-$C_3$ haloalkyl, $C_1$-$C_2$ alkoxy or $C_1$-$C_2$ haloalkoxy;

each $R^8$ is independently $C_1$-$C_2$ alkyl, $C_1$-$C_2$ haloalkyl, $C_1$-$C_2$ alkoxy, $C_1$-$C_2$ haloalkoxy, $C_2$-$C_4$ alkylcarbonyloxy or hydroxy; and each $R^9$ is independently halogen, hydroxy, $OCH_3$ or $CH_3$.

9. A compound of claim 8 wherein
Q is Q-1, Q-2, Q-8, Q-14, Q-23, Q-41, Q-59 or Q-62;
$Q^a$ is $CH_3$;
$R^5$ is $C_1$-$C_4$ alkyl, $C_1$-$C_4$ haloalkyl, $C_2$-$C_4$ alkenyl, $C_2$-$C_4$ haloalkenyl or cyano;
$R^6$ is H-1 or H-45;
$R^{12}$ is H or $CH_3$;
each $R^7$ is independently F, Cl, Br, $OCH_3$ or methyl;
$R^8$ is $CH_3$, $OCH_3$ or hydroxy;
$R^{10}$ is H or $CH_3$; and
$R^{15}$ is H.

10. A compound of claim 4 wherein
$W^1$ and $W^2$ are independently 0;
$Q^a$ is $CH_3$;
$R^{3a}$ is H;
m, j, n and p are all independently 0 or 1;
each $R^7$ is independently F, Cl, Br, $OCH_3$ or methyl;
each $R^8$ is independently $C_1$-$C_2$ alkyl, $C_1$-$C_2$ alkoxy or hydroxy; and
each $R^9$ is independently F, Cl, Br, hydroxy, $OCH_3$ or $CH_3$.

11. A compound of claim 10 wherein
$R^1$ is U-1 or U-50;
each $R^4$ is independently halogen, $C_1$-$C_3$ alkyl, $C_1$-$C_3$ haloalkyl or $C_1$-$C_2$ alkoxy;
k is 1 or 2;
G is G-1, G-2, G-15, G-26, G-27, G-36, G-37 or G-38;
Q is Q-1, Q-2, Q-8, Q-23 or Q-41;
$R^5$ is $C_1$-$C_4$ alkyl, $C_2$-$C_4$ alkenyl or cyano; and
$R^6$ is H-45;
provided that when k is 1, $R^4$ is connected to the 3- or 5-position of U-1 and to the 2- or 3-position of U-50; and when k is 2, an independently selected $R^4$ is connected to each of the 3- and 5-positions of U-1 and to each of the 2- and 5-positions of U-50.

12. A compound of claim 11 wherein
X is $X^1$; and
G is G-1.

13. A compound of claim 11 wherein
X is $X^1$; and
G is G-2.

14. A compound of claim 11 wherein
X is $X^1$; and
G is G-15.

15. A compound of claim 11 wherein
X is $X^1$; and
G is G-26.

16. A compound of claim 11 wherein
X is $X^1$; and
G is G-36.

17. A compound of claim 11 wherein
X is $X^2$; and
G is G-1.

18. A compound of claim 11 wherein
X is $X^2$; and
G is G-2.

19. The compound of claim 1 selected from the group consisting of:
1-[4-[4-[[methyl[(1R)-1,2,3,4-tetrahydro-1-naphthalenyl]amino]methyl]-2-thiazolyl]-1-piperidinyl]-2-[5-methyl-3-(trifluoromethyl)-1H-pyrazol-1-yl]ethanone,
2-[5-methyl-3-(trifluoromethyl)-1H-pyrazol-1-yl]-1-[4-[4-[[[(1R)-1,2,3,4-tetrahydro-1-naphthalenyl]amino]methyl]-2-thiazolyl]-1-piperidinyl]ethanone,
N-[[2-[1-[2-[5-methyl-3-(trifluoromethyl)-1H-pyrazol-1-yl]acetyl]-4-piperidinyl]-4-thiazolyl]methyl]-N-[(1R)-1,2,3,4-tatrahydro-1-naphthalenyl]acetamide,
N-[[2-[1-[2-[5-methyl-3-(trifluoromethyl)-1H-pyrazol-1-yl]acetyl]-4-piperidinyl]-4-thiazolyl]methyl]-N-[(1R)-1,2,3,4-tatrahydro-1-naphthalenyl]formamide,
N-methyl-2-[1-[3-[5-methyl-3-(trifluoromethyl)-1H-pyrazol-1-yl]-1-oxopropyl]-4-piperidinyl]-N-[(1R)-1,2,3,4-tetrahydro-1-naphthalenyl]-4-thiazolecarboxamide, and
ethyl 4-[4-[[methyl(1,2,3,4-tetrahydro-1-naphthalenyl)amino]carbonyl]-2-thiazolyl]-α-[5-methyl-3-(trifluoromethyl)-1H-pyrazol-1-yl]-β-oxo-1-piperidinepropanoate.

20. A method for controlling plant diseases caused by Oomycete fungal plant pathogens comprising applying to the plant or portion thereof, or to the plant seed or seedling, a fungicidally effective amount of a compound having a formula corresponding to of Formula 1 of claim 1.

21. A fungicidal composition comprising (1) a compound having a formula corresponding to of Formula 1 of claim 1; and (2) at least one other fungicide.

22. A fungicidal composition comprising (1) a fungicidally effective amount of a compound having a formula corresponding to of Formula 1 of claim 1; and (2) at least one additional component selected from the group consisting of surfactants, solid diluents and liquid diluents.

* * * * *

UNITED STATES PATENT AND TRADEMARK OFFICE
CERTIFICATE OF CORRECTION

PATENT NO. : 8,420,673 B2  
APPLICATION NO. : 12/521156  
DATED : April 16, 2013  
INVENTOR(S) : Pasteris et al.

Page 1 of 1

It is certified that error appears in the above-identified patent and that said Letters Patent is hereby corrected as shown below:

In the Claims

Column 126, line 10, Claim 1, "C(=O), C(=S), S(O), or S(O)$_2$; or" should read --C(=O), C(=S), S(O), and S(O)$_2$; or--.

Column 141, line 24, Claim 9, "$W^1$ and $W^2$ are independently 0;" should read --$W^1$ and $W^2$ are independently O;--.

Signed and Sealed this  
Third Day of September, 2013

Teresa Stanek Rea  
*Acting Director of the United States Patent and Trademark Office*